(12) United States Patent
Bernitz et al.

(10) Patent No.: US 8,551,710 B2
(45) Date of Patent: *Oct. 8, 2013

(54) METHODS FOR LOCALIZED IN SITU DETECTION OF MRNA

(75) Inventors: Mats Nilsson Bernitz, Bromma (SE); Chatarina Larsson, Uppsala (SE); Ida Grundberg, Uppsala (SE)

(73) Assignee: Leica Biosystems Newcastle Ltd., NewCastle Upon Tyne, (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/542,378

(22) Filed: Jul. 5, 2012

(65) Prior Publication Data

US 2013/0004953 A1 Jan. 3, 2013

Related U.S. Application Data

(63) Continuation of application No. 13/397,503, filed on Feb. 15, 2012.

(60) Provisional application No. 61/473,662, filed on Apr. 8, 2011, provisional application No. 61/442,921, filed on Feb. 15, 2011.

(51) Int. Cl.
  *C12Q 1/68* (2006.01)
  *C07H 21/04* (2006.01)

(52) U.S. Cl.
  USPC .................. 435/6.12; 536/24.31; 536/24.33

(58) Field of Classification Search
  None
  See application file for complete search history.

(56) References Cited

U.S. PATENT DOCUMENTS

| | | | |
|---|---|---|---|
| 5,354,668 A | 10/1994 | Auerbach | 435/91 |
| 5,591,582 A | 1/1997 | Bos et al. | 435/6 |
| 5,866,337 A | 2/1999 | Schon | 435/6 |
| 5,871,921 A | 2/1999 | Landegren et al. | 435/6 |
| 5,912,124 A | 6/1999 | Kumar | 435/6 |
| 6,143,495 A | 11/2000 | Lizardi et al. | 435/6 |
| 6,235,472 B1 | 5/2001 | Landegren et al. | 435/6 |
| 6,344,329 B1 | 2/2002 | Lizardi | 435/6 |
| 6,558,928 B1 | 5/2003 | Landegren | 435/91 |
| 6,610,481 B2 | 8/2003 | Koch | 435/6 |
| 6,632,609 B2 | 10/2003 | Lizardi | 435/6 |
| RE38,442 E | 2/2004 | Zhang et al. | 435/5 |
| 7,074,564 B2 | 7/2006 | Landegren | 435/6 |
| 7,294,468 B2 | 11/2007 | Bell et al. | 435/6 |
| 7,320,860 B2 | 1/2008 | Landegren et al. | 435/6 |

(Continued)

OTHER PUBLICATIONS

Larsson et al. Supplementary Information [online] Jul. 30, 2010 [retrieved on Oct. 18] retrieved from http://www.nature.com/nmeth/journal/v7/n5/suppinfo/nmeth.1448_S1.html (20 pages).*

(Continued)

*Primary Examiner* — Samuel Woolwine
(74) *Attorney, Agent, or Firm* — Fulbright & Jaworski LLP

(57) ABSTRACT

The present invention relates to the detection of RNA in a sample of cells. More particularly, the present invention relates to the localized detection of RNA in situ. The method relies on the conversion of RNA to complementary DNA prior to the targeting of the cDNA with a padlock probe(s). The hybridization of the padlock probe(s) relies on the nucleotide sequence of the cDNA which is derived from the corresponding nucleotide sequence of the target RNA. Rolling circle amplification of the subsequently circularized padlock probe produces a rolling circle product which may be detected. Advantageously, this allows the RNA to be detected in situ.

25 Claims, 9 Drawing Sheets

(56) References Cited

U.S. PATENT DOCUMENTS

| | | | |
|---|---|---|---|
| 7,351,528 B2 | 4/2008 | Landegren | 435/6 |
| 7,618,776 B2 | 11/2009 | Lizardi | 435/6 |
| 7,745,128 B2 | 6/2010 | Guo et al. | 435/6 |
| 2003/0143577 A1* | 7/2003 | Hogrefe et al. | 435/6 |

OTHER PUBLICATIONS

Larsson, C. "Single-molecule Detection in situ." Acta Universitatis Upsaliensis. Digital Comprehensive Summaries of Uppsala Dissertations from the Faculty of Medicine 431 (2009).*

Martinez et al. Non-radioactive localization of nucleic acids by direct in situ PCR and in situ RT-PCR in paraffin-embedded sections. The Journal of Histochemistry and Cytochemistry 43(8):739-747 (1995).*

Massarelli et al. KRAS mutation is an important predictor of resistance to therapy with epidermal growth factor receptor tyrosine kinase inhibitos in non-small cell lung cancer. Clinical Cancer Research 13:2890-2896 (2007).*

Ahlford et al., "A microfluidic platform for personalized cancer diagnostics by padlock probes ligation and circle-to-circle amplification," 15$^{th}$ International Conference on Miniaturized Systems for Chemistry and Life Sciences, pp. 61-63, 2011.

Johnstrup et al., "A microRNA detection system based on padlock probes and rolling circle amplification," RNA, 12:1747-1752, 2006.

Lagunavicius et al., "Novel application of Phi29 DNA polymerase: RNA detection and analysis in vitro and in situ by target RNA-primed RCA," RNA, 15:765-771, 2009.

Larsson et al., "In situ genotyping individual DNA molecules by target-primed rolling-circle amplification of padlock probes," Nature Methods, 1(3):227-232, 2004.

Larsson et al., "In situ detection and genotyping of individual mRNA molecules," Nature Methods, 7(5):395-397, 2010.

Lizardi et al., "Mutation detection and single-molecule counting using isothermal rolling-circle amplification," Nature Genetics, 19:225-232, 1998.

Merkiene et al., "Direct detection of RNA in vitro and in situ by target-primed RCA: The impact of E. coli RNase III on the detection efficiency of RNA sequences distanced far from the 3'-end," RNA, 16:1508-1515, 2010.

Mitra et al., "In situ localized amplification and contact replication of many individual DNA molecules," Nucleic Acid Research, 27(24):e34, 1999.

Nilsson et al., "Padlock Probes: Circularizing Oligonucleotides for Localized DNA Detection," Science, 265:2085-2088, 1994.

Nilsson et al., "Application of Padlock and Selector Probes in Molecular Medicine," Molecular Diagnostics, pp. 117-132, 2010.

Nilsson et al., "Enhanced detection and distinction of RNA by enzymatic probe ligation," Nature Biotechnology, 18:791-793, 2000.

Owczarzy et al., "Predicting Stability of DNA Duplexes in Solutions Containing Magnesium and Monovalent Cations," Biochemistry, 47:5336-5353, 2008.

Pena et al., "miRNA in situ hybridization in mammalian tissues fixed with formaldehyde and EDC," Nature Methods, 6(2):139-141, 2009.

Stougaard et al., "In situ detection of non-polyadenylated RNA molecules using Turtle Probes and target primed rolling circle PRINS," BMC Biotechnology, 7:69, 2007.

Wetmur et al., "DNA Probes: Applications of the Principles of Nucleic Acid Hybridization," Critical Review in Biochemistry and Molecular Biology, 26(3/4):227-259, 1991.

Baner et al., "More keys to padlock probes: mechanisms for high-throughput nucleic acid analysis", Current Opinion in Biotechnology, vol. 12, pp. 11-15, Feb. 1, 2001.

Baner et al., "Signal amplification of padlock probes by rolling circle replication", Nucleic Acids Research, vol. 26, No. 22, pp. 5037-5078, Nov. 15, 1998.

Chang et al., "Detection of N-, H-, and KRAS codons 12, 13, and 61 mutations with universal RAS primer multiplex PCR and N-, H-, and KRAS-specific primer extension", Clinical Biochemistry, vol. 43, No. 3, pp. 296-301, Feb. 1, 2010.

Henriksson, "Application of Padlock Probe Based Nucleic Acid Analysis in Situ", Digital Comprehensive Summaries of Uppsala Dissertations from the Faculty of Medicine 575, p. 15, Dec. 1, 2010.

International Search Report and Written Opinion issued in PCT Application No. PCT/IB2012/000995, dated Oct. 22, 2012.

Jishan Li et al., "Typing of Multiple Single-Nucleotide Polymorphisms by a Microsphere-Based Rolling Circle Amplification Assay", Analytical Chemistry, vol. 79, No. 23, pp. 9030-9038, Dec. 1, 2007.

Lee et al., "A Robust Approach to Identifying Tissue-Specific Gene Expression Regulatory Variants Using Personalized Human Induced Pluripotent Stem Cells", Plos Genetics, vol. 5, No. 11, p. e100718, Nov. 13, 2009.

Shi et al., "Multiplex detection of CpG methylation using microarray combining with target-selection-padlock probe", Clinica Chimica Acta., vol. 411, No. 17-18, pp. 1187-1194, Sep. 6, 2010.

Vaughn et al., "Frequency of KRAS, BRAF, and NRAS mutations in colorectal cancer", Genes, Chromosomes and Cancer, vol. 50, No. 5, pp. 307-312, Feb. 8, 2011.

* cited by examiner

FIGs. 2a-d

Example of padlock probe (70 nt long) targeting BRAF wild-type:
5'- GAAATCTCGATGGAGNNNNNNNN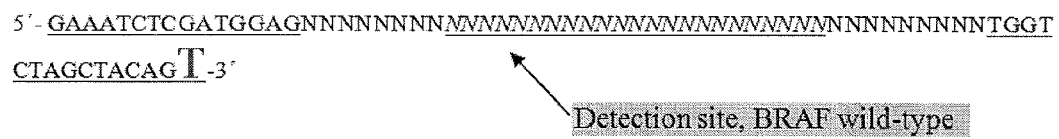NNNNNNNNNTGGT
CTAGCTACAGT-3'
Detection site, BRAF wild-type
Example of padlock probe (70 nt long) targeting BRAF mutant:
5'- GAAATCTCGATGGAGNNNNNNNN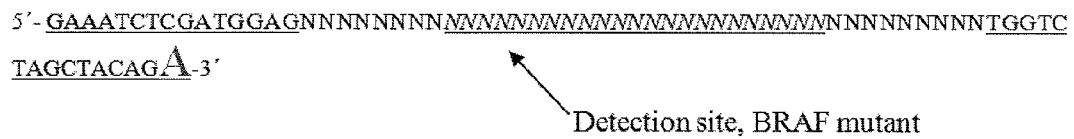NNNNNNNNNTGGTC
TAGCTACAGA-3'
Detection site, BRAF mutant
FIG. 9

METHODS FOR LOCALIZED IN SITU DETECTION OF MRNA

This application is a continuation of co-pending U.S. patent application Ser. No. 13/397,503 filed Feb. 15, 2012, which claims priority to U.S. Provisional Application Ser. No. 61/473,662, filed Apr. 8, 2011, and U.S. Provisional Application Ser. No. 61/442,921, filed Feb. 15, 2011, both of which are incorporated by reference in their entirety. This application is related to the PCT application No. PCT/IB2012/000995 entitled "Method for Localized In Situ Detection of mRNA" by Mats Nilsson Bernitz, Chatarina Larsson, and Ida Grundberg filed on Feb. 15, 2012, which is incorporated by reference in its entirety.

BACKGROUND

In some embodiments, the present invention relates to the detection of RNA, especially mRNA, in a sample of cells. More particularly, the present invention relates in particular embodiments to the localized detection of RNA, particularly mRNA, in situ. In certain aspects, the method relies on the conversion of RNA to complementary DNA (cDNA) prior to the targeting of the cDNA with a padlock probe(s). The hybridization of the padlock probe(s) relies on the nucleotide sequence of the cDNA which is derived from the corresponding nucleotide sequence of the target RNA. Rolling circle amplification (RCA) of the subsequently circularized padlock probe produces a rolling circle product (RCP) which allows detection of the RNA. Advantageously, the RCP may be localized to the RNA allowing the RNA to be detected in situ. Also, provided are kits for performing such methods.

It is generally desirable to be able sensitively, specifically, qualitatively and/or quantitatively to detect RNA, and in particular mRNA, in a sample, including for example in fixed or fresh cells or tissues. It may be particularly desirable to detect an mRNA in a single cell. For example, in population-based assays that analyze the content of many cells, molecules in rare cells may escape detection. Furthermore, such assays provide no information concerning which of the molecules detected originate from which cells. Expression in single cells can vary substantially from the mean expression detected in a heterogeneous cell population. It is also desirable that single-cell studies may be performed with single-molecule sensitivity which allows the fluctuation and sequence variation in expressed transcripts to be studied. Fluorescence in situ hybridization (FISH) has previously been used to detect single mRNA molecules in situ. Although permitting determination of transcript copy numbers in individual cells, this technique cannot resolve highly similar sequences, so it cannot be used to study, for example, allelic inactivation or splice variation and cannot distinguish among gene family members.

The only option available for assigning transcript variants to a single cell in a given tissue involves polymerase chain reaction (PCR) of laser-capture microdissected material, which is time consuming and error prone, and thus not suitable for diagnostics.

As an alternative to PCR- and hybridization-based methods, padlock probes (Nilsson et al., 1994) have for many years been used to analyze nucleic acids. These highly selective probes are converted into circular molecules by target-dependent ligation upon hybridization to the target sequence. Circularized padlock probes can be amplified by RCA in situ (Lizardi et al., 1998), and thus can be used to provide information about the localization of target molecules, including, where DNA targets are concerned, at the single-cell level. Such a protocol is described in Larrson et al., 2004), in which the target DNA molecule is used to prime the RCA reaction, causing the RCP to be anchored to the target molecule, thereby preserving its localization and improving the in situ detection.

While RNA molecules can also serve as templates for the ligation of padlock probes (Nilsson et al., 2000), RNA detection with padlock probes in situ has so far proven more difficult than DNA detection and is subject to limitations (Lagunavicius et al., 2009). For example, the high selectivity reported for padlock probes with in situ DNA detection and genotyping has not been reproduced with detection of RNA targets in situ. This is possibly due to problems with ligation of DNA molecules on an RNA template, since it is known that both the efficiency and the specificity of the ligation reaction are lower compared to ligation on a DNA template (Nilsson et al., 2000; Nilsson et al. 2001). It has recently been demonstrated that RNA molecules may be detected in situ with padlock probes and target-primed RCA (Lagunavicius et al., 2009; Stougaard et al., 2007). However, thus far, detection through target-primed RCA has for the most part been restricted to sequences in the 3'-end of non-polyadenylated RNA or sequences adjacent to the poly(A)-tail of mRNA. Since target-priming of the RCA reaction is dependent on a nearby free 3'-end that can be converted into an RCA primer, it is thought that this limitation results from the formation of RNA secondary structures which impede the polymerase action (3' exonucleolysis) required to convert the RNA into a reaction primer. The detection efficiency of direct mRNA detection with padlock probes has been estimated to be as low as 1% (Nilsson et al., 2001). For the detection of non-polyadenylated RNA molecules, it has been noted that ligation of the probes using an internal hairpin structure as template resulted in higher detection efficiency than using the RNA molecule itself as ligation template (Stougaard et al., 2007). This indicates that better ligation conditions are required to be able to efficiently detect and genotype RNA directly with padlock probes in situ.

None of the methods for in situ detection of RNA presented thus far provide the possibility to detect sequence variation at the single nucleotide level and in particular to genotype transcripts. In the present invention, by converting an RNA target molecule into cDNA, the reduction in padlock probe ligation efficiency and specificity is avoided and the excellent genotyping properties provided by padlock probes are preserved. In addition, it has been found that unlike many previously described methods, embodiments are not restricted to detection of sequences positioned at specific sites in the RNA molecules.

SUMMARY OF THE INVENTION

Methods and compositions advantageously allow for detection of RNA, and particularly, the detection of single nucleotide variations in RNA. For example, a detection resolution may be achieved that allows the study of differences in the relative expression of two allelic transcripts directly in tissue. Such studies have recently been recognized as important in the context of large-scale analyses of allele-specific expression, since it has been shown that many genes undergo this type of transcriptional regulation and that the allelic expression can differ among tissues. Furthermore, it has been shown that most human genes undergo alternative splicing, which could now be studied at the single-cell level using the methods described herein. No other in situ method exists today that can perform multiplex detection of expressed single nucleotide sequence variants in RNA. It is believed that the present method can meet this need, and that the ability it provides to visualize transcriptional variation directly in cells and tissues will be of value in both research and diagnostics, providing new insights about the human transcriptome.

According to one method of the present invention, transcript detection in situ is accomplished by first converting the at least one mRNA into localized cDNA molecules that are detected with padlock probes and target-primed RCA (FIG. 1). Whilst of particular applicability to mRNA, the method may be used for the detection of any RNA molecule present in a cell, including but not limited to viral RNA, tRNA, rRNA, small nuclear RNA (snRNA), small nucleolar RNA (snoRNA), microRNA (miRNA), small interfering RNA (siRNA), piwi-interacting RNA (piRNA), antisense RNA and non-coding RNA. The RNA is converted into cDNA, typically in a reverse transcriptase reaction comprising a reverse transcriptase enzyme and one or more reverse transcriptase primers. A ribonuclease is employed to digest the RNA in the resultant RNA:DNA duplex thus making the cDNA strand available for hybridization to a padlock probe(s). Hybridization of the padlock probe(s) to the cDNA allows circularization of the probe by direct or indirect ligation of the ends of the probe(s). The circularized padlock probe is then subjected to RCA and a RCP is detected by any appropriate means available in the art. The method may, in specific embodiments, also be used for localizing more than one target RNA, e.g. 2, 3, 4, 5, 6 or more target RNAs. These target RNAs may be derived from the same gene, or from different genes, or be derived from the same genomic sequence, or from different genomic sequences.

In one embodiment, the invention provides a method for in situ detection of at least one target RNA in a sample of one or more cells, comprising: generating a cDNA complementary to an RNA in the sample; adding a ribonuclease to said sample to digest the RNA hybridized to said cDNA; contacting said sample with one or more padlock probes wherein said padlock probe(s) comprise terminal regions complementary to immediately adjacent regions on said cDNA and hybridizing said padlock probe to the cDNA at said complementary terminal regions; ligating the ends of said padlock probe(s); subjecting said circularized padlock probe(s) to rolling circle amplification (RCA); and detecting the rolling circle amplification product(s).

In a further embodiment, the present invention provides a method for determining the presence and location of a genetic sequence in a cell in a biological sample comprising: (a) hybridizing a DNA complement having the genetic sequence to RNA; (b) digesting RNA hybridized to the DNA complement; (c) hybridizing a first padlock probe to at least a portion of the DNA complement, wherein the padlock probe comprises the genetic sequence on one of two terminal ends that are complementary to different but immediately adjacent regions of the DNA complement; (d) ligating the two terminal ends of the padlock probe; (e) replicating the circularized probe to yield a nucleic acid molecule comprising multiple copies of the replicated probe; and (f) detecting presence or absence of the genetic sequence in the cell using a probe that hybridizes to the nucleic acid molecule. In certain aspects, the method further comprises generating the DNA complement that is hybridized to the RNA.

In another embodiment, the present invention provides a method for identifying a cell in a tissue sample that has a specific nucleic acid sequence comprising: (a) incubating the cell with a DNA complement that includes the specific nucleic acid sequence to generate an RNA-DNA hybrid; (b) incubating the RNA target molecule with a ribonuclease under conditions to digest at least part of the RNA-DNA hybrid; (c) incubating the DNA complement with a padlock probe under conditions to hybridize the padlock probe to the DNA complement comprising the specific nucleic acid sequence, wherein the padlock probe comprises two terminal ends that are complementary to different but immediately adjacent regions of the DNA complement; (d) incubating the DNA complement and padlock probe with a ligase under conditions to join terminal ends of the padlock probe; (e) incubating the ligated padlock probe with a polymerase and nucleotides under conditions to prime replication of the padlock probe with the DNA complement and generate a nucleic acid with multiple copies of the replicated padlock probe; and (f) incubating the nucleic acid with multiple copies of the replicated padlock probe with one or more complementary oligonucleotides to detect the presence or absence of the specific sequence.

In one embodiment, the present invention provides a method for identifying a cell in a cell sample that has a specific nucleic acid sequence comprising: (a) incubating the cell sample with a ribonuclease-resistant primer that is immobilized to the sample and reverse transcriptase under conditions to generate a DNA complement of an RNA, wherein the DNA complement comprises the specific nucleic acid sequence; (b) incubating the cell sample with a ribonuclease under conditions to digest at least part of the RNA; (c) incubating the DNA complement with a padlock probe under conditions to hybridize the padlock probe to the DNA complement comprising the specific nucleic acid sequence, wherein the padlock probe comprises two terminal ends that are complementary to different but immediately adjacent regions of the DNA complement; (d) incubating the DNA complement and padlock probe with a ligase under conditions to join terminal ends of the padlock probe; (e) incubating the ligated padlock probe with a polymerase and nucleotides under conditions to prime replication of the padlock probe with the DNA complement and generate a nucleic acid with multiple copies of the replicated padlock probe; and (f) incubating the nucleic acid with multiple copies of the replicated padlock probe with one or more nucleic acid probes to detect the presence or absence of the specific sequence.

In another embodiment, the present invention provides a method for in situ localization of a nucleic acid sequence in a cell in a biological sample on a slide comprising: (a) incubating an immobilized biological sample on solid support with reverse transcriptase and a ribonuclease-resistant primer under conditions to generate a nucleic acid molecule that contains the nucleic acid sequence and that hybridizes to a complementary RNA molecule in the cell to form an RNA-DNA hybrid; (b) adding a ribonuclease and incubating the ribonuclease under conditions to digest RNA in the RNA-DNA hybrid; (c) incubating the digested RNA-DNA hybrid under conditions to hybridize a complementing padlock probe to the DNA portion of the digested RNA-DNA hybrid, wherein the padlock probe comprises the nucleic acid sequence and has two terminal ends that are complementary to different but immediately adjacent regions of the DNA; (d) incubating the padlock probe hybridized to the DNA portion of the RNA-DNA hybrid with a ligase under conditions to ligate the terminal ends of the padlock probe; (e) incubating the ligated padlock probe with a polymerase and nucleotides under conditions to create a primer from the DNA that is used to replicate the padlock probe and generate a nucleic acid with multiple copies of the replicated padlock probe; and (f) incubating the nucleic acid with one or more complementing nucleic acid probes to detect the presence or absence of the specific sequence.

In specific embodiments of the methods for identifying a cell in a tissue sample, the methods for identifying a cell in a cell sample, or the methods for in situ localization of a nucleic acid sequence in a cell in a biological sample of the invention, e.g. as mentioned above, the sample is a formalin-fixed paraffin-embedded tissue section.

In another embodiment, the present invention provides a method for localized in situ detection of at least one RNA in a sample of cells, said method comprising: (a) contacting said sample with a reverse transcriptase and a reverse transcriptase primer to generate cDNA from RNA in the sample; (b) adding a ribonuclease to said sample to digest the RNA hybridized to said cDNA; (c) contacting said sample with one or more padlock probes wherein said padlock probe(s) comprise terminal regions complementary to said cDNA and hybridizing said padlock probe(s) to the cDNA at said complementary terminal regions; (d) circularizing said padlock probe(s) by ligating, directly or indirectly, the ends of said padlock probe(s); (e) subjecting said circularized padlock probe(s) to rolling circle amplification (RCA) using a DNA polymerase having 3'-5' exonuclease activity wherein, if necessary, said exonuclease activity digests the cDNA to generate a free 3' end which acts as a primer for said RCA; and (f) detecting the rolling circle amplification product(s).

The methods thus involve detecting the rolling circle amplification product (RCP) as a means of detecting the target RNA. The RCP is generated as a consequence of padlock probe recognition of a cDNA complementary to the target RNA (i.e. padlock probe binding to the cDNA complement of the target RNA by hybridization to complementary sequences in the cDNA) and ligation of the padlock probe to generate a circular template for the RCA reaction. The RCP may thus be viewed as a surrogate marker for the cDNA, which is detected to detect the RNA.

As discussed above, the method may be used for the detection of any RNA molecule type or RNA sequence present in a cell. In some embodiments, the method is used for the detection of mRNA. The cDNA complementary to the RNA in the sample may be generated by contacting said sample with an RNA-dependent DNA polymerase and a primer. The RNA dependent DNA polymerase may be, for example, a reverse transcriptase, such as an MMLV reverse transcriptase or an AMV reverse transcriptase.

In certain aspects of the invention, the primer used for first strand cDNA synthesis is ribonuclease resistant. A primer which is "ribonuclease resistant" means that it exhibits some (i.e, a measurable or detectable) degree of increased resistance to ribonuclease action (in particular to the action of an RNase H) over a naked, unmodified primer of the same sequence. Thus the primer is at least partially protected from digestion by the ribonuclease, or more particularly when the primer is hybridized to its RNA template, the primer/template hybrid is at least partially protected from ribonuclease digestion. In some embodiments at least 50% survives the ribonuclease treatment, while in further embodiments at least 60, 70, 80 or 90%, or even 100% survives the ribonuclease treatment. A primer may, for example, comprise 2'O-Me RNA, methylphosphonates or 2' Fluor RNA bases, locked nucleic acid residues, or peptide nucleic acid residues, which make the primer resistant to digestion by ribonucleases.

In one embodiment, the primer comprises 2, 3, 4, 5, 6, 7, 8, 9 or more locked nucleic acids separated by 1 or more natural or synthetic nucleotides in the primer sequence. In certain embodiments, the primer comprises between 4 to 9 locked nucleic acids, with each locked nucleic acid being separated for the other locked nucleic acids by 1 or more natural or synthetic nucleotides in the primer sequence.

The term "reverse transcriptase primer" or "RT primer" as used herein (also known as a cDNA primer) refers to an oligonucleotide capable of acting as a point of initiation of cDNA synthesis by an RT under suitable conditions. Thus, a reverse transcription reaction is primed by an RT primer. The appropriate length of an RT primer typically ranges from 6 to 50 nucleotides or from 15 to 35 nucleotides. Short primer molecules generally require cooler temperatures to form sufficiently stable hybrid complexes with the mRNA template, but may still be used. Shortening the primer from 30 to 25 nucleotides did not affect its function. A primer need not reflect the exact sequence of the template nucleic acid, but must be sufficiently complementary to hybridize with the template. The design of suitable primers for cDNA synthesis is well known in the art.

Typically, an RT primer is designed to bind to the region of interest in the RNA, for example a region within a particular RNA it is desired to detect, or a region within which sequence variations may occur (for example, allelic or splice variants, polymorphisms or mutations, etc., e.g. SNPs, etc.). Thus, in seeking to detect the presence or absence of particular mutations, etc. (e.g. in a genotyping context), the RT primer may be designed to bind in or around the region within which such mutations occur (e.g. near to such a region, for example within 100, 70, 50, 30, 20, 15, 10 or 5 nucleotides of such a region). Such mutations or sequence variations may be associated with disease (e.g. cancer) or disease risk or predisposition, or may with response to a therapeutic treatment, etc.

RT primers can incorporate additional features which allow for the immobilization of the primer to or within a cell in the sample but do not alter the basic property of the primer, that of acting as a point of initiation of cDNA synthesis. Thus it is contemplated that the primer may be provided with a functional moiety or means for immobilization of the primer to a cell or cellular component. This may for example be a moiety capable of binding to or reacting with a cell or cellular component and, as described above, such a cellular component may include RNA. Thus, the functional moiety may include a moiety(ies) which allow the primer to remain hybridized to the primer binding site within the template RNA, namely a moiety(ies) which render the primer resistant to ribonuclease digestion.

The primer may be modified to incorporate one or more reactive groups, e.g. chemical coupling agents, capable of covalent attachment to cells or cellular components. This may be achieved by providing the primer with chemical groups or modified nucleotide residues which carry chemical groups such as a thiol, hydroxy or amino group, a phosphate group via EDC (1-Ethyl-3-(3-dimethylaminopropyl)carbodiimide hydrochloride), NHS (N-hydroxysuccinimide)-esters, etc. which are reactive with cellular components such as proteins, etc. Such chemical coupling groups and means of introducing them into nucleic acid molecules are well known in the art. Potential reactive functionalities thus include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides.

Alternatively or in addition, the primer may be provided with an affinity binding group capable of binding to a cell or cellular component or other sample component. Such an affinity binding group may be any such binding group known in the art which has specific binding activity for a corresponding binding partner in or on a cell, tissue, sample component, etc. Thus, representative binding groups include antibodies and their fragments and derivatives (e.g. single chain antibodies, etc.), other binding proteins, which may be natural or synthetic, and their fragments and derivatives, e.g. lectins, receptors, etc., binding partners obtained or identified by screening technology such as peptide or phage display, etc., aptamers and such like, or indeed small molecule binding partners for proteins e.g. for receptors and other proteins on or within cells. Such immobilization systems may work best in relation to cellular components which are abundant e.g. actin filaments.

The target RNA or the synthesized cDNA may be attached to a synthetic component in the sample, e.g. a synthetic gel matrix, instead of the native cellular matrix to preserve the localization of the detection signals. The cells or tissue may be immersed in a gel solution that upon polymerization will give rise to a gel matrix to which the cDNA or target can be attached. For example, if an Acrydite modification is included at the 5' end of the cDNA primer, the cDNA can be covalently attached to a polyacrylamide matrix (Mitra and Church, 1999).

Alternatively or in addition to the aforementioned modifications to the RT primer, the modification described above may be used in which the 5' phosphate of the primer may be linked to amines present on proteins in the cellular matrix via EDC-mediated conjugation, thus helping to maintain the localization of the RNA relative to other cellular components. Such a technique has previously been described in relation to microRNAs and their detection via in situ hybridization (Pena et al., 2009).

To ensure good ribonuclease resistance it may in certain instances be advantageous to use several modified residues in the RT primer, such as 2, 3, 4, 5 or 6 modified residues in a row for example. In some embodiments, modified residues may be incorporated into the RT primer every second, or every third, residue. In additional embodiments, the RT primer may comprise, comprise at least, or comprise at most 1, 2, 3, 4, 5, 6, 7, 8, 9, 10, 11, 12 or more modified residues (or any range derivable therein). In the literature various modifications of nucleic acids that impart ribonuclease resistance have been described and any modification that prevents, or partially prevents, digestion of the RT primer or the RNA to which it is hybridized is encompassed in this method.

In one embodiment the modifications (e.g. modified residues) are placed at the 5' end of the primer (in the 5' region of the primer) and the 3' end is left unmodified. For example, in some embodiments, at least or at most 1, 2, 3, 4, 5 or 6 residues from the 3' end (or any range of derivable therein) are unmodified.

A preferred modification to confer ribonuclease resistance is the incorporation of LNA residues into the RT primer. Thus the RT primer may include at least 1 LNA residue and in certain embodiments include at least or at most 2, 3, 4, 5, 6, 7, 8 or 9 LNA residues (or any range derivable therein). As well conferring ribonuclease resistance, LNA monomers have enhanced hybridization affinity for complementary RNA, and thus may be used to enhance hybridization efficiency.

In a representative embodiment of the invention, the RT primer comprises LNA residues every second, or every third, residue. LNA is a bicyclic nucleotide analogue wherein a ribonucleoside is linked between the 2'-oxygen and the 4'-carbon atoms by a methylene unit. Primers comprising LNA exhibit good thermal stabilities towards complementary RNA, which permits good mismatch discrimination. Furthermore, LNA offers the possibility to adjust $T_m$ values of primers and probes in multiplex assays.

The cDNA that is generated may be from 10 nucleotides to 1000 nucleotides in length, and in certain embodiments may range from 10 to 500 nucleotides in length including from 50 to 500 nucleotides in length, e.g., from 90 to 400 nucleotides in length, such as from 90 to 200 nucleotides in length, from 90 to 100 nucleotides in length, and so on. In certain representative embodiments, the cDNA may range in length from 10 to 100 nucleotides in length, from 30 to 90 nucleotides in length, from 14 to 70 nucleotides in length, from 50 to 80 nucleotides in length, and any length of integers between the stated ranges.

The cDNA may be made up of deoxyribonucleotides and/or synthetic nucleotide residues that are capable of participating in Watson-Crick-type or analogous base pair interactions. Thus the nucleotides used for incorporation in the reverse transcriptase step for synthesis of the cDNA may include any nucleotide analogue or derivative that is capable of participating in the reverse transcriptase reaction (i.e., capable of being incorporated by the reverse transcriptase).

Ribonucleases, also known as RNases, are a class of enzymes that catalyze the hydrolysis of RNA. A ribonuclease for use according to the method of the present invention will be able to degrade RNA in an RNA:DNA duplex. The RNases H are a family of ribonucleases that cleave the 3'-O-P-bond of RNA in a DNA:RNA duplex to produce 3'-hydroxyl and 5'-phosphate terminated products. Since RNase H specifically degrades the RNA in RNA:DNA hybrids and will not degrade DNA or unhybridized RNA it is commonly used to destroy the RNA template after first-strand cDNA synthesis by reverse transcription. RNase H thus represents a preferred class of enzymes for use. Members of the RNase H family can be found in nearly all organisms, from archaea and prokaryota to eukaryota. Again, suitable ribonuclease, particularly RNase H, enzymes are well-known and widely available.

Upon the hybridization of the terminal regions of a padlock probe to a complementary cDNA sequence, the padlock probe is "circularized" by ligation. The ciruculariztion of the padlock probe(s) may be carried out by ligating, directly or indirectly, the ends of said padlock probe(s). Procedures, reagents and conditions for this are well known and described in the art and may be selected according to choice. Suitable ligases include e.g., Tth DNA ligase, Taq DNA ligase, *Thermococcus* sp. (strain 9° N) DNA ligase (9°N™ DNA ligase, New England Biolabs), Ampligase™ (Epicentre Biotechnologies) and T4 DNA ligase. In specific embodiments, the in the ciruculariztion of the padlock probe(s) step, the terminal regions of the padlock probe may hybridize to non-contiguous regions of the cDNA such that there is a gap between said terminal regions. In further specific embodiments of this method, the gap may be a gap of 1 to 60 nucleotides, such as a gap of 1 to 40 nucleotides or a gap of 3 to 40 nucleotides. In specific embodiments, the gap may be a gap of 1, 2, 3, 4, 5, 6, 7, 8, 9, 10, 11, 12, 13, 14, 15, 16, 17, 18, 19, 20, 21, 22, 23, 24, 25, 27, 30, 32, 35, 37, 40, 42, 45, 47, 50, 52, 55, 57 or 60 nucleotides, of any integer of nucleotides in between the indicated values. In further embodiments, the gap may be larger than 60 nucleotides. In further embodiments, the gap may have a size of more than 60 nucleotides. In further embodiments, the gap between said terminal regions may be filled by a gap oligonucleotide or by extending the 3' end of the padlock probe. The gap oligonucleotide may accordingly have a size of 1 to 60 nucleotides, e.g. a size of 1, 2, 3, 4, 5, 6, 7, 8, 9, 10, 11, 12, 13, 14, 15, 16, 17, 18, 19, 20, 21, 22, 23, 24, 25, 27, 30, 32, 35, 37, 40, 42, 45, 47, 50, 52, 55, 57 or 60 nucleotides, or any integer of nucleotides in between the indicated values. In further embodiments, the size of the gap oligonucleotide may be more than 60 nucleotides.

Rolling circle amplification or "RCA" of the circularized padlock probe results in the synthesis of a concatemeric amplification product containing numerous tandem repeats of the probe nucleotide sequence. RCA reactions and the conditions therefor are widely described in the literature and any such conditions, etc. may be used, as appropriate. The ligation reaction may be carried out at the same time (i.e. simultaneously) as the RCA reaction of step, i.e. in the same step. In some embodiments, the RCA reaction is primed by the 3' end of the cDNA strand to which the padlock probe has hybridized. In other embodiments, instead of priming the RCA reaction with the 3' end of the cDNA, a primer is hybridized to the padlock probe and primes the RCA reaction. In certain aspects, this primer hybridizes to a region of the padlock probe other than the 5' and 3' terminal regions of the padlock probe.

Where the RCA reaction is primed by the 3' end of the cDNA strand to which the padlock probe has hybridized, any unpaired 3' nucleotides in the cDNA are removed in order to generate the primer for RCA. This may be achieved by using a polymerase having 3'-5' exonuclease activity. Such target-primed RCA procedures are known and described in the art as are appropriate polymerase enzymes for such use. Thus, for example, a DNA polymerase such phi29 (φ29) polymerase, Klenow fragment, *Bacillus stearothermophilus* DNA polymerase (BST), T4 DNA polymerase, T7 DNA polymerase, or DNA polymerase I may be used. The skilled person may readily determine other suitable polymerases which might be used, including, for example, DNA polymerases that have been engineered or mutated to have desirable characteristics. In the RCA reaction, the polymerase thus extends the 3' end of the cDNA using the circularized padlock probe as template. As a result of RCA, concatemeric amplification products containing numerous tandem repeats of the probe nucleotide sequence are produced and may be detected as indicative of the presence and/or nature of a RNA in the sample. Alternatively, a separate enzyme having 3'-5' exonuclease activity may be added to the reaction to generate the free 3' end, in which case a DNA polymerase lacking 3'-5' exonuclease activity could then be used for RCA. In some cases, depending on the proximity of the hybridized padlock probe to the 3' end of the target cDNA, it may not be necessary to digest the cDNA to generate a free 3' end at the appropriate position for it to act as a primer for RCA.

The terms "padlock probe" and "probe" and their plural forms are synonymous and are used interchangeably throughout this specification. The use of a single padlock probe occurs in the case of a "simplex" (as opposed to "multiplex") embodiment of the method of the invention, i.e. when a single RNA or a single variant in a RNA are to be detected. It will be understood that the term "single" as used in relation to a padlock probe, or the RNA, means single in the sense of a "single species," i.e. a plurality of RNA molecules of the same type may be present in the sample for detection, and a plurality of identical padlock probes specific for that RNA may be used, but such pluralities relate only to a unique sequence of RNA or padlock probe. In multiplex embodiments, two or more different target RNAs are to be detected in a sample of cells. In such embodiments, the sample of cells is contacted with a plurality of padlock probes for each target RNA, such that the number of probes contacted with the sample may be two or more, e.g., three or more, four or more, etc. Optionally, up to 10, 15 or 20 probes may be used. Such methods find particular use in high-throughput applications. For example, the method may employ or may employ at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or any range derivable therein, padlock probes in a single reaction.

For example, in one embodiment, the method comprises contacting the sample with at least a first and a second padlock probe, wherein the first padlock probe comprises terminal regions complementary to immediately adjacent regions on said cDNA, and wherein the second padlock probe comprises terminal regions that differ from the terminal regions of the first padlock probe only by a single nucleotide at the 5' or 3' terminus of the second padlock probe. In this manner, the two padlock probes can be used to detect a single nucleotide differences in an RNA sequence. For example, the first padlock probe may be configured to hybridize to a cDNA complementary to a wild-type mRNA sequence, and the second padlock probe is configured to hybridize to a cDNA complementary to a single nucleotide variant of the mRNA sequence. In addition to detecting nucleic acid substitutions, the padlock probes may be configured to detect insertions or deletions in a nucleic acid sequence.

The padlock probe may be of any suitable length to act as an RCA template. For example, the padlock probe may have an overall length (including two arms and a backpiece) of between 50 and 150 nucleotides, of between 60 to 120 nucleotides, or of between 70 to 100 nucleotides. Thus, the padlock probe may have, for instance, a length of, of at least, or of at most 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides, or any range derivable therein. The arms of the padlock probes may have any suitable length, e.g. each may have a length of 12, 13, 14, 15, 16, 17, 18, 19, 20, 21, 22, e.g. 13, 24, 25, 26, 27, 28, 29, 30, 32, 35, 36, 37, 38, 39 or 40 nucleotides, or any range derivable therein. The length of the two arms of the padlock probes may, in certain embodiments, be identical or essentially identical, e.g. showing a length difference of 1-2 nucleotides. In further embodiments, the length of the two arms may differ one from the other by more than 2 nucleotides, e.g. one arm having a length of 15 nucleotides, whereas the other having a length of 20 nucleotides. The length difference in some embodiments may not surpass 5 to 7 nucleotides. In addition to the end regions, which are complementary to the cDNA, the probe may contain features or sequences or portions useful in RCA or in the detection or further amplification of the RCA product. Such sequences may include binding sites for an RCA primer, hybridization probes, and/or amplification or sequencing primers. Thus, a padlock probe may be viewed as having a "back piece" which links the 3' and 5' target-complementary regions. By including within this back piece or linking region a particular sequence, to which when amplified by RCA of the circularized probe, a detection probe or primer may bind in the RCP, the padlock probe may be seen as having, or more particularly as providing, a detection site for detection of the RCP. Accordingly, the padlock probe may contain an arbitrary "tag" or "barcode" sequence which may be used diagnostically to identify the cDNA, and by extension the corresponding mRNA, to which a given RCA product relates, in the context of a multiplex assay. Such a sequence is simply a stretch of nucleotides comprising a sequence designed to be present only in the padlock probe which is "specific for" (i.e. capable of hybridizing only to) a particular cDNA. Thus, for example in the context of padlock probes for genotyping, the tag sequence (or detection site) may be different for the padlock probes designed to detect the wild-type sequence and the mutant(s)/sequence variant(s) thereof.

In certain aspects of the invention, the padlock probes comprise a "tag" or "detection probe binding region." The detection probe binding region may be used to incorporate detection probe binding regions into the rolling circle amplification products for subsequent hybridization to labeled detection probes. Different padlock probes may have different detection probe binding regions such that differentially labeled detection probes may be used in the detection of the rolling circle amplification products. For example, a first padlock probe may comprise a first detection probe binding region, and a second padlock probe may comprise a second detection probe binding region. The sample may then be contacted with a first labeled detection probe comprising a sequence identical to the first detection probe binding region of the first padlock probe, and a second labeled detection probe comprising a sequence identical to the second detection probe binding region of the first padlock probe, such that the first and second labeled detection probes hybridize to the rolling circle amplification products, if any, generated by the first and second padlock probes.

The term "detection" is used broadly herein to include any means of determining, or measuring (e.g. quantitatively determining), the presence of at least one RNA (i.e. if, or to what extent, it is present, or not) in the sample. "Localized" detection means that the signal giving rise to the detection of the RNA is localized to the RNA. The RNA may therefore be detected in or at its location in the sample. In other words the spatial position (or localization) of the RNA within the sample may be determined (or "detected"). This means that the RNA may be localized to, or within, the cell in which it is expressed or to a position within the cell or tissue sample. Thus "localized detection" may include determining, measuring, assessing or assaying the presence or amount and location, or absence, of RNA in any way. Quantitative and qualitative determinations, measurements or assessments are included, including semi-quantitative. Such determinations, measurements or assessments may be relative, for example when two or more different RNAs in a sample are being detected.

As used herein, the term "in situ" refers to the detection of at least one RNA in its native context, i.e. in the cell, bodily fluid, or tissue in which it normally occurs. Thus, this may refer to the natural or native localization of an RNA. In other words, the RNA may be detected where, or as, it occurs in its native environment or situation. Thus, the RNA is not moved from its normal location, i.e. it is not isolated or purified in any way, or transferred to another location or medium, etc. Typically, this term refers to the RNA as it occurs within a cell or within a cell, organ, bodily fluid, or tissue sample, e.g. its native localization within the cell or tissue and/or within its normal or native cellular environment.

A variety of labels are known for labeling nucleic acids and may be used in the detection of rolling circle amplification products. Non-limiting examples of such labels include fluorescent labels, chromogenic labels, radioactive labels, luminescent labels, magnetic labels, and electron-density labels. Labels may be incorporated directly into the amplification product, such as with modified or labeled dNTPs during amplification. Alternatively, the amplification products may be labeled indirectly, such as by hybridization to labeled probes. In multiplex reactions, it is contemplated that a different label may be used for each different amplification product that may be present in the reaction.

The method of detection will depend on the type of label used. In certain embodiments, the detection is by imaging or direct visualization of fluorescent or chromogenic labels. Accordingly, the present method allows for the detection of the amplification products in situ at the location of the target RNA. This sensitivity permits, for example, genotyping at the single-cell level.

The "sample" may be any sample of cells in which an RNA molecule may occur, to the extent that such a sample is amenable to in situ detection. Typically, the sample may be any biological, clinical or environmental sample in which the RNA may occur, and particularly a sample in which the RNA is present at a fixed, detectable or visualizable position in the sample. The sample will thus be any sample which reflects the normal or native (in situ) localization of the RNA, i.e. any sample in which it normally or natively occurs. The sample may, for example, be derived from a tissue or organ of the body, or from a bodily fluid. Such a sample will advantageously be or comprise a cell or group of cells such as a tissue. The sample may, for example, be a colon, lung, pancreas, prostate, skin, thyroid, liver, ovary, endometrium, kidney, brain, testis, lymphatic fluid, blood, plasma, urinary bladder, or breast sample, or comprise colon, lung, pancreas, prostate, skin, thyroid, liver, ovary, endometrium, kidney, brain, testis, lymphatic fluid, blood, urinary bladder, or breast cells, groups of cells or tissue portions.

Particularly preferred are samples such as cultured or harvested or biopsied cell or tissue samples, e.g., as mentioned above, in which the RNA may be detected to reveal the qualitative nature of the RNA, i.e. that it is present, or the nucleotide sequence of the mRNA or the presence and/or identity of one or more nucleotides in the mRNA, and localization relative to other features of the cell. The sample of cells may be freshly prepared or may be prior-treated in any convenient way such as by fixation or freezing. Accordingly, fresh, frozen or fixed cells or tissues may be used, e.g. FFPE tissue (Formalin Fixed Paraffin Embedded). Thus, tissue sections, treated or untreated, may be used. Alternatively a touch imprint sample of a tissue may be used. In this procedure a single layer of cells is printed onto a surface (e.g. a slide) and the morphology is similar to normal tissue sections. The touch imprint are obtained using fresh tissue sample. Other cytological preparations may be used, e.g. cells immobilized or grown on slides, or cell prepared for flow cytometry. In specific embodiments, the sample of cells or tissues may be prepared, e.g. freshly prepared, or may be prior-treated in any convenient way.

The sample may comprise any cell type that contains RNA including all types of mammalian and non-mammalian animal cells, plant cells, algae including blue-green algae, fungi, bacteria, protozoa, etc. Representative samples thus include clinical samples, e.g. whole blood and blood-derived products, blood cells, tissues, biopsies, as well as other samples such as cell cultures and cell suspensions, etc. In certain aspects of the invention, the sample contains, or is suspected of containing, cancer cells, such as colorectal cancer or lung cancer cells, pancreas cancer, prostate cancer, skin cancer, thyroid cancer, liver cancer, ovary cancer, endometrium cancer, kidney cancer, cancer of the brain, testis cancer, acute non lymphocytic leukemia, myelodysplasia, urinary bladder cancer, head and neck cancer or breast cancer cells. For example, the sample may be a colon, lung, pancreas, prostate, skin, thyroid, liver, ovary, endometrium, kidney, brain, testis, lymphatic fluid, blood, plasma, urinary bladder, or breast sample suspected to be cancerous, or suspected to comprise an mRNA found in a cancer or cancerous cell, or cancerous cell group or tissue.

In some embodiments, a sample is obtained from a patient who previously was known to have cancer, which was treated or went into remission. In some cases, the patient may have a recurrent cancer. In other embodiments, the patient may have a metastasis or be suspected of having a metastasis or be at risk for metastasis. A patient at risk for cancer or metastasis may be at risk because of familial history or at determination of other genetic predispositions. In other embodiments, the patient may have been determined or may be determined to have cells exhibiting the pathology of cancer or precancer cells.

Cancer "recurrence," in pathology nomenclature, refers to cancer re-growth at the site of the primary tumor. For many cancers, such recurrence results from incomplete surgical removal or from micrometastatic lesions in neighboring blood or lymphatic vessels outside of the surgical field. Conversely, "metastasis" refers to a cancer growth distant from the site of the primary tumor. Metastasis of a cancer is believed to result from vascular and/or lymphatic permeation and spread of tumor cells from the site of the primary tumor prior to surgical removal. The prevailing clinical nomenclature used for cancer statistics is somewhat confusing in that patients who experience a second episode of a treated cancer are referred to as having undergone a "recurrence", whereas these lesions are usually temporally remote metastases at sites distant from the primary cancer. This clinical terminology will be used herein, i.e., the term "recurrence" denotes these late-arising metastatic lesions, unless specific pathologic nomenclature is needed to separate the two forms of clinical recurrence.

In certain embodiments, the sample contains pre-cancerous or premalignant cells, including but not limited to metaplasias, dysplasias, and/or hyperplasias. It may also be used to identify undesirable but benign cells, such as squamous metaplasia, dysplasia, benign prostate hyperplasia cells, and/or hyperplastic lesions.

In additional embodiments, methods and compositions are implemented with respect to a specific type of lung cancer. They may be implemented with patients diagnosed, at risk for, or exhibiting symptoms of a specific type of lung cancer. In some embodiments, the specific type of lung cancer is non-small cell lung cancer (NSCLC) as distinguished from small cell lung cancer (SCLC). In other embodiments, the NSCLC is squamous cell carcinoma (or epidermoid carcinoma), adenocarcinoma, bronchioalveolar carcinoma, or large-cell undifferentiated carcinoma.

In certain embodiments, methods and compositions are implemented with respect to a specific type of colon cancer. They may be implemented with patients diagnosed, at risk for, or exhibiting symptoms of a specific type of colon cancer. In some embodiments, the specific type of colon cancer is an adenocarcinoma, leiomyosarcoma, colorectal lymphoma, melanoma, neuroendocrine tumors (aggressive or indolent). In the case of adenocarcinomas, the cancer may be further subtyped into mucinous or signet ring cell.

The terms "target, "target sequence", "target region", and "target nucleic acid," etc. are used synonymously herein and refer to the nucleic acid, or to a region or sequence thereof, which is to be detected or to which a reagent used in the method binds, for example the RNA to be detected, or the cDNA, or more particularly the regions thereof, to which the padlock probe is hybridized. Thus a target sequence may be within a cDNA, in which case it is to be understood that the cDNA nucleotide sequence is derived from and is complementary to the target RNA nucleotide sequence. The target may, in certain embodiments, be a single RNA molecule. In other embodiments, the target may be at least one RNA molecule, e.g. a group of 2, 3, 4, 5, 6 or more RNA molecules. These RNA molecules may differ in molecule type, and/or may differ in sequence.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989; Wetmur, 1991; Owczarzy et al., 2008, which are incorporated herein by reference). Thus the design of appropriate primers and probes, and the conditions under which they hybridize to their respective targets is well within the routine skill of the person skilled in the art.

Mutations in KRAS are common in several types of cancer. In certain embodiments, the present invention provides a method for detecting the presence or absence of KRAS mutations in situ. In particular embodiments, the method uses padlock probe(s) configured to hybridize to cDNA(s) corresponding to one or more mutant KRAS mRNA sequences selected from the group consisting of 12AGT, 12CGT, 12TGT, 12GAT, 12GCT, 12GTT, and 13GAC (wherein the wild-type sequence is 12GGT and 13GGC) and mutants of KRAS codon 61, mutants of KRAS codon 146, and mutants of the 3' untranslated region of KRAS. In certain embodiments, the method uses padlock probe(s) configured to hybridize to cDNA(s) corresponding to the wild-type KRAS sequence. In further embodiments, the method uses padlock probe(s) configured to hybridize to cDNA(s) corresponding to one or more mutant KRAS mRNA sequences selected from the group consisting of 12AGT, 12CGT, 12TGT, 12GAT, 12GCT, 12GTT, and 13GAC (wherein the wild-type sequence is 12GGT and 13GGC) and mutants of KRAS codon 61, mutants of KRAS codon 146, and mutants of the 3' untranslated region of KRAS; and to one or more wild-type KRAS mRNA sequences selected from the group consisting of 12GGT and 13GGC, wild-type sequences of KRAS codon 61, KRAS codon 146, and of the 3' untranslated region of KRAS.

In another embodiment, the present invention provides a method for detecting the presence or absence of mutations in mRNA that codes for HER2, cMyc, TERT, APC, Braf, PTEN, PI3K, and/or EGFR. In particular embodiments, the method uses padlock probe(s) configured to hybridize to cDNA(s) corresponding to one or more mutant HER2, cMyc, TERT, Braf, APC, PTEN and/or PI3K mRNA sequences. In further embodiments, the method uses padlock probe(s) configured to hybridize to cDNA(s) corresponding to one or more wild-type HER2, cMyc, TERT, Braf, APC, PTEN and/or PI3K mRNA sequences. In further embodiments, padlock probe(s) are configured to hybridize to cDNA(s) corresponding to one or more mutant Braf, PTEN and/or PI3K mRNA sequences, and to one or more wild-type Braf, APC, PTEN and/or PI3K mRNA sequences. The present invention accordingly provides methods for detecting the presence or absence of a rolling circle amplification product corresponding to one or more of mutant and wild-type Braf APC, PTEN and/or PI3K mRNA sequences.

In yet another group of embodiments, the padlock probe(s) are configured to hybridize to cDNA(s) corresponding to one or more mutant KRAS mRNA sequences and to one or more mutant Braf mRNA sequences; or to one or more mutant KRAS mRNA sequences and to one or more mutant APC mRNA sequences; or to one or more mutant KRAS mRNA sequences and to one or more mutant PTEN mRNA sequences; or to one or more mutant KRAS mRNA sequences and to one or more mutant PI3K mRNA sequences. The present invention accordingly provides methods for detecting the presence or absence of a rolling circle amplification product corresponding to mutant KRAS and mutant Braf mRNA sequences; or corresponding to mutant KRAS and mutant APC mRNA sequences; or corresponding to mutant KRAS and mutant PTEN mRNA sequences; or corresponding to mutant KRAS and mutant PI3K mRNA sequences.

In further embodiments, the padlock probe(s) are configured to hybridize to cDNA(s) corresponding to wild-type KRAS and wild-type Braf mRNA sequences; or corresponding to wild-type KRAS and wild-type APC mRNA sequences; or corresponding to wild-type KRAS and wild-type PTEN mRNA sequences; or corresponding to wild-type KRAS and wild-type PI3K mRNA sequences. The present invention accordingly provides methods for detecting the presence or absence of a rolling circle amplification product corresponding to wild-type KRAS and Braf mRNA sequences; or corresponding to wild-type KRAS and APC mRNA sequences; or corresponding to wild-type KRAS and PTEN mRNA sequences; or corresponding to wild-type KRAS and PI3K mRNA sequences.

In a further group of embodiments, the padlock probe(s) are configured to hybridize to cDNA(s) (i) corresponding to one or more mutant KRAS mRNA sequences and to one or more mutant Braf mRNA sequences; or corresponding to one or more mutant KRAS mRNA sequences and to one or more mutant APC mRNA sequences; or corresponding to one or more mutant KRAS mRNA sequences and to one or more mutant PTEN mRNA sequences; or corresponding to one or more mutant KRAS mRNA sequences and to one or more mutant PI3K mRNA sequences; and (ii) corresponding to wild-type KRAS and Braf mRNA sequences; or corresponding to wild-type KRAS and APC mRNA sequences; or corresponding to wild-type KRAS and PTEN mRNA sequences; or corresponding to wild-type KRAS and PI3K mRNA sequences. The present invention accordingly provides methods for detecting the presence or absence of a rolling circle amplification product corresponding to one or more mutant and wild-type KRAS and Braf mRNA sequences; or corresponding to one or more mutant and wild-type KRAS and APC mRNA sequences; or corresponding to one or more mutant and wild-type KRAS and PTEN mRNA sequences; or corresponding to one or more mutant and wild-type KRAS and PI3K mRNA sequences.

In one embodiment, the present invention provides a collection of padlock probes specific for mutations to the KRAS gene, comprising:

| | |
|---|---|
| Y1-X1-Z1-A | (a) |
| Y1-X1-Z1-T | (b) |
| Y1-X1-Z1-C | (c) |
| Y2-X1-Z2-A | (d) |
| Y2-X1-Z2-T | (e) |
| Y2-X1-Z2-C, | (f) | and

| | |
|---|---|
| Y3-X1-Z3-A; | (g) | where:
X1 is from 5-50 nucleotides;
Y1+Z1=20 to 40 nucleotides;
Y2+Z2=20 to 40 nucleotides;
Y3+Z3=20 to 40 nucleotides;
Y1 is GTGGCGTAGGCAAGA (SEQ ID NO:1), GTGGCGTAGGCAAG (SEQ ID NO:2), GTGGCGTAGGCAA (SEQ ID NO:3), GTGGCGTAGGCA (SEQ ID NO:4), GTGGCGTAGGC (SEQ ID NO:5), GTGGCGTAGG (SEQ ID NO:6), GTGGCGTAG, GTGGCGTA, GTGGCGT, GTGGCG, GTGGC, GTGG, GTG, GT, G;
Y2 is TGGCGTAGGCAAGAG (SEQ ID NO:7), TGGCGTAGGCAAGA (SEQ ID NO:8), TGGCGTAGGCAAG (SEQ ID NO:9), TGGCGTAGGCAA (SEQ ID NO:10), TGGCGTAGGCA (SEQ ID NO:11), TGGCGTAGGC (SEQ ID NO:12), TGGCGTAGG, TGGCGTAG, TGGCGTA, TGGCGT, TGGCG, TGGC, TGG, TG, T;
Y3 is TGGCGTAGGCAAGAGTGC (SEQ ID NO:13), TGGCGTAGGCAAGAGTG (SEQ ID NO:14), TGGCGTAGGCAAGAGT (SEQ ID NO:15), TGGCGTAGGCAAGAG (SEQ ID NO:7), TGGCGTAGGCAAGA (SEQ ID NO:8), TGGCGTAGGCAAG (SEQ ID NO:9), TGGCGTAGGCAA (SEQ ID NO:10), TGGCGTAGGCA (SEQ ID NO:11), TGGCGTAGGC (SEQ ID NO:12), TGGCGTAGG, TGGCGTAG, TGGCGTA, TGGCGT, TGGCG, TGGC, TGG, TG, T;
Z1 is TGGTAGTTGGAGCT (SEQ ID NO:27), GGTAGTTGGAGCT (SEQ ID NO:28), GTAGTTGGAGCT (SEQ ID NO:29), TAGTTGGAGCT (SEQ ID NO:30), AGTTGGAGCT (SEQ ID NO:31), GTTGGAGCT, TTGGAGCT, TGGAGCT, GGAGCT, GAGCT, AGCT, GCT, CT, T, or a bond;
Z2 is GGTAGTTGGAGCTG (SEQ ID NO:16), GTAGTTGGAGCTG (SEQ ID NO:17), TAGTTGGAGCTG (SEQ ID NO:18), AGTTGGAGCTG (SEQ ID NO:19), GTTGGAGCTG (SEQ ID NO:20), TTGGAGCTG, TGGAGCTG, GGAGCTG, GAGCTG, AGCTG, GCTG, CTG, TG, G or a bond; and
Z3 is AGTTGGAGCTGGGTG (SEQ ID NO:21), GTTGGAGCTGGGTG (SEQ ID NO:22), TTGGAGCTGGGTG (SEQ ID NO:23), TGGAGCTGGGTG (SEQ ID NO:24), GGAGCTGGGTG (SEQ ID NO:25), GAGCTGGGTG (SEQ ID NO:26), AGCTGGGTG, GCTGGGTG, CTGGGTG, TGGGTG, GGGTG, GGTG, GTG, TG, G or a bond.

In some embodiments, the collection of KRAS probes, further comprises:

| | |
|---|---|
| Y1-X2-Z1-G | (h) |
| Y2-X2-Z2-G | (i) |
| Y3-X2-Z3-G | (j) | where X2 is from 10-50 nucleotides and differs from X1.

In a specific embodiment, the collection of KRAS probes, further comprises:

| | |
|---|---|
| Y1-X2-Z1-G | (h) |
| Y2-X2-Z2-G | (i) |
| Y3-X2-Z3-G | (j) | where X2 is from 10-50 nucleotides and differs from X1.

In further embodiments, the present invention provides a collection of padlock probes specific for mutations to the Braf gene comprising:

Y1-X1-Z1-A (k)

where:
X1 is from 5-50 nucleotides;
Y1+Z1=20 to 40 nucleotides;
Y1 is GAAATCTCGATGGAG (SEQ ID NO:102), AAATCTCGATGGAG (SEQ ID NO:103), AATCTCGATGGAG (SEQ ID NO:104), ATCTCGATGGAG (SEQ ID NO:105), TCTCGATGGAG (SEQ ID NO:106), CTCGATGGAG (SEQ ID NO:107), TCGATGGAG, CGATGGAG, GATGGAG, ATGGAG, TGGAG, GGAG, GAG, AG, G; and
Z1 is TGGTCTAGCTACAG (SEQ ID NO:108), GGTCTAGCTACAG (SEQ ID NO:109), GTCTAGCTACAG (SEQ ID NO:110), TCTAGCTACAG (SEQ ID NO:111), CTAGCTACAG (SEQ ID NO:112), TAGCTACAG, AGCTACAG, GCTACAG, CTACAG, TACAG, ACAG, CAG, AG, G, or a bond.

In some embodiments, the collection of Braf probes further comprises:

Y1-X2-Z1-T (l)

where X2 is from 10-50 nucleotides.

In a specific embodiment, the collection of Braf probes further comprises:

Y1-X2-Z1-T (l)

where X2 is from 10-50 nucleotides and differs from X1.

In further embodiments, the present invention provides a collection of padlock probes specific for mutations to the APC gene, PTEN gene, PI3K gene, KRAS gene codon 61 or codon 146, or KRAS gene 3'UTR, comprising:

Y1-X1-Z1-W (m)

where:
X1 is from 5-50 nucleotides;
Y1+Z1=20 to 40 nucleotides;
wherein Y1 comprises 5-20 nucleotides 3' to a point mutation in the APC gene, PTEN gene, PI3K gene, KRAS gene codon 61 or codon 146, or KRAS gene 3'UTR;
wherein Z1 comprises 5-20 nucleotides in the 5' to a point mutation in the APC gene, PTEN gene, PI3K gene, KRAS gene codon 61 or codon 146, or KRAS gene 3'UTR; and
wherein W is a nucleotide complementary to a point mutation in the APC gene, PTEN gene, PI3K gene, KRAS gene codon 61 or codon 146, or KRAS gene 3'UTR.

In specific embodiments, the collection of probes specific for mutations to the APC gene, PTEN gene, PI3K gene, KRAS gene codon 61 or codon 146, or KRAS gene 3'UTR, further comprises:

Y1-X2-Z1-V (n)

where X2 is from 10-50 nucleotides; and
wherein V is a nucleotide complementary to a wildtype sequence at the site of a point mutation in the APC gene, PTEN gene, PI3K gene, KRAS gene codon 61 or codon 146, or KRAS gene 3'UTR.

In specific embodiments, the collection of probes specific for mutations to the APC gene, PTEN gene, PI3K gene, KRAS gene codon 61 or codon 146, or KRAS gene 3'UTR, further comprises:

Y1-X2-Z1-V (n)

where X2 is from 10-50 nucleotides and differs from X1; and
wherein V is a nucleotide complementary to a wildtype sequence at the site of a point mutation in the APC gene, PTEN gene, PI3K gene, KRAS gene codon 61 or codon 146, or KRAS gene 3'UTR.

In some embodiments, X1 is from 25-50 nucleotides. In certain embodiments, X1 comprises at least one labeled nucleotide. In some embodiments, each probe (a)-(g) has the same X1. In some embodiments, each probe selected from (a)-(g), (k) and (m) has the same X2.

In certain aspects of the invention, each of Y1+Z1, Y2+Z2 and Y3+Z3 is at least 25 nucleotides.

In certain aspects of the invention, each probe in the collection of probes has a GC content of at least 40%.

In some embodiments, the present invention provides a collection of padlock probes specific for mutations to the KRAS gene, specific for mutations to the Braf gene, specific for mutations to the APC gene, PTEN gene, PI3K gene, KRAS gene codon 61 or codon 146, or KRAS gene 3'UTR, and optionally collections of padlock probes specific for corresponding wild-type sequences, e.g. as defined above, the collection being capable of detecting a plurality of mutations in (i) the KRAS gene, (ii) the KRAS gene and the Braf gene, (iii) the KRAS gene and the APC gene, (iv) the KRAS gene and the PTEN gene, or (v) the KRAS gene and the PI3K gene, wherein the plurality of mutations constitute at least 40% of KRAS mutations associated with cancer.

In further embodiments, the present invention provides a collection of padlock probes specific for mutations to the KRAS gene, specific for mutations to the Braf gene, specific for mutations to the APC gene, PTEN gene, PI3K gene, KRAS gene codon 61 or codon 146, or KRAS gene 3'UTR, and optionally collections of padlock probes specific for corresponding wild-type sequences, e.g. as defined above, wherein the detection of mutations to (i) the KRAS gene, (ii) the KRAS gene and the Braf gene, (iii) the KRAS gene and the APC gene, (iv) the KRAS gene and the PTEN gene, or (v) the KRAS gene and the PI3K gene allows to determine the presence of cancer or a predisposition for cancer.

In a specific embodiment said cancer or predisposition for cancer is determined in at least or in at most 5%, 10%, 15%, 20%, 25%, 30%, 40%, 45%, 50%, 55%, 60%, 65%, 70%, 75%, 80%, 85%, 90% or 95% (or any range derivable therein) of patients bearing a KRAS-mutant associated with tumor development.

In further embodiments, the present invention provides the use of a collection of padlock probes specific for mutations to the KRAS gene, specific for mutations to the Braf gene, specific for mutations to the APC gene, PTEN gene, PI3K gene, KRAS gene codon 61 or codon 146, or KRAS gene 3'UTR, and optionally collections of padlock probes specific for corresponding wild-type sequences, e.g. as defined above, for the determination of the presence or absence of a KRAS-mutant tumor or for the determination of a predisposition for a KRAS-mutant tumor in a patient or group of patients.

In specific embodiments, the determination of the presence or absence of a KRAS-mutant tumor or for the determination of a predisposition for a KRAS-mutant tumor in a patient or group of patients allows to determine the presence of cancer in at least or in at most 5%, 10%, 15%, 20%, 25%, 30%, 40%, 45%, 50%, 55%, 60%, 65%, 70%, 75%, 80%, 85%, 90% or 95% (or any range derivable therein) of a patient group bearing a KRAS-mutant associated with tumor development.

A "patient bearing a KRAS-mutant associated with tumor development" or a "patient group bearing a KRAS-mutant associated with tumor development" refers to an individual or group of individuals, wherein each patient or group member comprises at least one mutation in the KRAS gene (or a corresponding mutant), that has been described in the scientific literature or is known to the skilled person as being associated with tumor development, e.g., associated with preforms of tumors or predispositions for tumors, associated with different tumor development stages, or associated with full grown tumors or cancer. In specific embodiments, these mutations or mutants comprise mutations as can be derived from the Sanger database as of Feb. 15, 2012 being associated with cancer or precancer (on the world wide web at sanger.ac.uk).

In specific embodiments, the patient group, i.e. each member of the patient group, may bear a KRAS-mutant associated with tumor development and an additional mutation in the Braf gene, and/or the APC gene, and/or PTEN gene, and/or the PI3K gene. These combinations of mutations may contribute to tumor development associated with KRAS mutations; or they may constitute mutational combinations associated with cancer or precancer forms, or predispositions for cancer. In further specific embodiments, the patient group, i.e., each member of the patient group, may bear a mutation in the Braf gene, and/or the APC gene, and/or PTEN gene, and/or the PI3K gene. These mutations are associated with cancer or precancer, or predispositions for cancer as can be derived from the Sanger database (on the world wide web at sanger.ac.uk). In further specific embodiments, the patient group, i.e. each member of the patient group, may bear a mutation in the EGFR gene, and/or the KRAS gene, and/or the Braf gene, and/or the APC gene, and/or PTEN gene, and/or the PI3K gene. These mutations are associated with cancer or precancer, or predisposition for cancer, as can be derived from the Sanger database (on the world wide web at sanger.ac.uk). Furthermore, examples of EGFR mutations that may be detected according to the present invention, or that may be employed in the context of compositions of the present invention are shown in Table 7.

In certain embodiments, said cancer is colorectal cancer, lung cancer, pancreas cancer, prostate cancer, skin cancer, thyroid cancer, liver cancer, ovary cancer, endometrium cancer, kidney cancer, cancer of the brain, testis cancer, acute non lymphocytic leukemia, myelodysplasia, urinary bladder cancer, head and neck cancer or breast cancer. In further embodiments, the predispositions to cancer are predispositions to colorectal cancer, lung cancer, pancreas cancer, prostate cancer, skin cancer, thyroid cancer, liver cancer, ovary cancer, endometrium cancer, kidney cancer, cancer of the brain, testis cancer, acute non lymphocytic leukemia, myelodysplasia, urinary bladder cancer, head and neck cancer or breast cancer.

In further embodiments the colorectal cancer is metastatic colorectal cancer, adenocarcinoma, leiomyosarcoma, colorectal lymphoma, melanoma or neuroendocrine tumor. In other embodiments, the lung cancer is a non-small cell lung cancer (NSCLC), or small cell lung cancer (SCLC).

In further embodiments, the present invention provides a collection of padlock probes specific for mutations to the KRAS gene, specific for mutations to the Braf gene, specific for mutations to the APC gene, PTEN gene, PI3K gene, KRAS gene codon 61 or codon 146, or KRAS gene 3'UTR, and optionally collections of padlock probes specific for corresponding wild-type sequences, e.g. as defined above, or uses thereof, e.g. as defined above, allowing to determine (i) the presence of colorectal cancer in at least 25 to 60% of a patient group bearing a KRAS-mutant associated with tumor development;

(ii) the presence of lung cancer in at least 25 to 60% of a patient group bearing a KRAS-mutant associated with tumor development;

(iii) the presence of pancreas cancer in at least 80 to 90% of a patient group bearing a KRAS-mutant associated with tumor development;

(iv) the presence of prostate cancer in at least 5 to 25% of a patient group bearing a KRAS-mutant associated with tumor development;

(v) the presence of skin cancer in at least 5 to 25% of a patient group bearing a KRAS-mutant associated with tumor development;

(vi) the presence of thyroid cancer in at least 5 to 60% of a patient group bearing a KRAS-mutant associated with tumor development;

(vii) the presence of liver cancer in at least 10 to 25% of a patient group bearing a KRAS-mutant associated with tumor development;

(viii) the presence of ovary cancer in at least 5 to 50% of a patient group bearing a KRAS-mutant associated with tumor development;

(ix) the presence of endometrium cancer in at least 10 to 40% of a patient group bearing a KRAS-mutant associated with tumor development;

(x) the presence of kidney cancer in at least 5 to 50% of a patient group bearing a KRAS-mutant associated with tumor development;

(xi) the presence of cancer of the brain in at least 5 to 15% of a patient group bearing a KRAS-mutant associated with tumor development;

(xii) the presence of testis cancer in at least 10 to 45% of a patient group bearing a KRAS-mutant associated with tumor development;

(xiii) the presence of acute non lymphocytic leukemia in at least 5 to 15% of a patient group bearing a KRAS-mutant associated with tumor development;

(xiv) the presence of urinary bladder cancer in at least 5% of a patient group bearing a KRAS-mutant associated with tumor development;

(xv) the presence of head and neck cancer in at least 5 to 10% of a patient group bearing a KRAS-mutant associated with tumor development; or (xvi) the presence of breast cancer in at least 5 to 10% of a patient group bearing a KRAS-mutant associated with tumor development.

In some embodiments, the above-mentioned collections of probes are provided in a kit along with one or more of the following:

(ii) an reverse transcriptase primer comprising one or more locked nucleic acid and capable of hybridizing to said target RNA;
(iii) a reverse transcriptase;
(iv) a ribonuclease;
(v) a ligase;
(vi) a polymerase having 3' exonuclease activity;
(vii) a detection probe capable of hybridizing to a complement of said padlock probe; or
(ix) nucleotides.

In further embodiments, the present invention provides a method for localized in situ detection of mRNA which codes for one or more mutations of the KRAS gene in a sample of cells on a slide surface, comprising:

(a) generating cDNA from mRNA in the sample, wherein the primer is provided with a functional moiety capable of binding to or reacting with a cell or cellular component or an affinity binding group capable of binding to a cell or cellular component;

(b) adding a ribonuclease to said sample to digest the mRNA hybridized to said cDNA;

(c) contacting said sample with one or more padlock probes specific for mutations to the KRAS gene, wherein each padlock probe comprises a sequence selected from the collection of padlock probes specific for mutations to the KRAS gene, specific for mutations to the Braf of gene, specific for mutations to the APC gene, PTEN gene, PI3K gene, KRAS gene codon 61 or codon 146, or KRAS gene 3'UTR, and optionally collections of padlock probes specific for corresponding wild-type sequences, e.g. as defined above.

In one embodiment, the present invention provides a method for localized in situ detection of mRNA which codes for one or more mutations of the KRAS gene in a sample of cells on a slide surface, comprising: (a) generating cDNA from mRNA in the sample, wherein the primer is provided with a functional moiety capable of binding to or reacting with a cell or cellular component or an affinity binding group capable of binding to a cell or cellular component; (b) adding a ribonuclease to said sample to digest the mRNA hybridized to said cDNA; (c) contacting said sample with one or more padlock probes specific for mutations to the KRAS gene, wherein each padlock probe comprises a sequence selected from the group consisting of:

Y1-X1-Z1-A (a)

Y1-X1-Z1-T (b)

Y1-X1-Z1-C (c)

Y2-X1-Z2-A (d)

Y2-X1-Z2-T (e)

Y2-X1-Z2-C, (f)

and

Y3-X1-Z3-A; (g)

where:
X1 is from 5-50 nucleotides;
Y1+Z1=20 to 40 nucleotides;
Y2+Z2=20 to 40 nucleotides;
Y3+Z3=20 to 40 nucleotides;
Y1 is GTGGCGTAGGCAAGA (SEQ ID NO:1), GTGGCGTAGGCAAG (SEQ ID NO:2), GTGGCGTAGGCAA (SEQ ID NO:3), GTGGCGTAGGCA (SEQ ID NO:4), GTGGCGTAGGC (SEQ ID NO:5), GTGGCGTAGG (SEQ ID NO:6), GTGGCGTAG, GTGGCGTA, GTGGCGT, GTGGCG, GTGGC, GTGG, GTG, GT, G;
Y2 is TGGCGTAGGCAAGAG (SEQ ID NO:7), TGGCGTAGGCAAGA (SEQ ID NO:8), TGGCGTAGGCAAG (SEQ ID NO:9), TGGCGTAGGCAA (SEQ ID NO:10), TGGCGTAGGCA (SEQ ID NO:11), TGGCGTAGGC (SEQ ID NO:12), TGGCGTAGG, TGGCGTAG, TGGCGTA, TGGCGT, TGGCG, TGGC, TGG, TG, T;
Y3 is TGGCGTAGGCAAGAGTGC (SEQ ID NO:13), TGGCGTAGGCAAGAGTG (SEQ ID NO:14), TGGCGTAGGCAAGAGT (SEQ ID NO:15), TGGCGTAGGCAAGAG (SEQ ID NO:7), TGGCGTAGGCAAGA (SEQ ID NO:8), TGGCGTAGGCAAG (SEQ ID NO:9), TGGCGTAGGCAA (SEQ ID NO:10), TGGCGTAGGCA (SEQ ID NO:11), TGGCGTAGGC (SEQ ID NO:12), TGGCGTAGG, TGGCGTAG, TGGCGTA, TGGCGT, TGGCG, TGGC, TGG, TG, T;
Z1 is TGGTAGTTGGAGCT (SEQ ID NO:27), GGTAGTTGGAGCT (SEQ ID NO:28), GTAGTTGGAGCT (SEQ ID NO:29), TAGTTGGAGCT (SEQ ID NO:30), AGTTGGAGCT (SEQ ID NO:31), GTTGGAGCT, TTGGAGCT, TGGAGCT, GGAGCT, GAGCT, AGCT, GCT, CT, T, or a bond;
Z2 is GGTAGTTGGAGCTG (SEQ ID NO:16), GTAGTTGGAGCTG (SEQ ID NO:17), TAGTTGGAGCTG (SEQ ID NO:18), AGTTGGAGCTG (SEQ ID NO:19), GTTGGAGCTG (SEQ ID NO:20), TTGGAGCTG, TGGAGCTG, GGAGCTG, GAGCTG, AGCTG, GCTG, CTG, TG, G or a bond; and
Z3 is AGTTGGAGCTGGGTG (SEQ ID NO:21), GTTGGAGCTGGGTG (SEQ ID NO:22), TTGGAGCTGGGTG (SEQ ID NO:23), TGGAGCTGGGTG (SEQ ID NO:24), GGAGCTGGGTG (SEQ ID NO:25), GAGCTGGGTG (SEQ ID NO:26), AGCTGGGTG, GCTGGGTG, CTGGGTG, TGGGTG, GGGTG, GGTG, GTG, TG, G or a bond;

(d) ligating, directly or indirectly, the ends of said padlock probe(s);
(e) subjecting said circularized padlock probe(s) to rolling circle amplification (RCA) using a DNA polymerase having 3'-5' exonuclease activity wherein if necessary said exonuclease activity digests the cDNA to generate a free 3' end which acts as a primer for said RCA; and
(f) detecting the rolling circle amplification product(s).

In some embodiments of the method, step (c) further comprises contacting said sample with padlock probes (h), (i) and (j), wherein each is specific for wild-type KRAS gene and have sequences:

Y1-X2-Z1-G (h)

Y2-X2-Z2-G, (i)

and

Y3-X2-Z3-G (j)

where X2 is from 10-50 nucleotides.

In specific embodiments of the method, step (c) further comprises contacting said sample with padlock probes (h), (i) and (j), wherein each is specific for wild-type KRAS gene and have sequences:

Y1-X2-Z1-G (h)

Y2-X2-Z2-G, (i)

and

Y3-X2-Z3-G (j)

where X2 is from 10-50 nucleotides and differs from X1.

In a further embodiment, the present invention provides a method for localized in situ detection of mRNA which codes for one or more mutations of the Braf gene in a sample of cells on a slide surface, comprising:
(a) generating cDNA from mRNA in the sample, wherein the primer is provided with a functional moiety capable of binding to or reacting with a cell or cellular component or an affinity binding group capable of binding to a cell or cellular component;
(b) adding a ribonuclease to said sample to digest the mRNA hybridized to said cDNA;
(c) contacting said sample with one or more padlock probes specific for mutations to the Braf gene, wherein each padlock probe comprises a sequence selected from the group consisting of:

Y1-X1-Z1-A (k)

where:
X1 is from 5-50 nucleotides;
Y1+Z1=20 to 40 nucleotides;
Y1 is GAAATCTCGATGGAG (SEQ ID NO:102), AAATCTCGATGGAG (SEQ ID NO:103), AATCTCGATGGAG (SEQ ID NO:104), ATCTCGATGGAG (SEQ ID NO:105), TCTCGATGGAG (SEQ ID NO:106), CTCGATGGAG (SEQ ID NO:107), TCGATGGAG, CGATGGAG, GATGGAG, ATGGAG, TGGAG, GGAG, GAG, AG, G; and
Z1 is TGGTCTAGCTACAG (SEQ ID NO:108), GGTCTAGCTACAG (SEQ ID NO:109), GTCTAGCTACAG (SEQ ID NO:110), TCTAGCTACAG (SEQ ID NO:111), CTAGCTACAG (SEQ ID NO:112), TAGCTACAG, AGCTACAG, GCTACAG, CTACAG, TACAG, ACAG, CAG, AG, G, or a bond;
(d) ligating, directly or indirectly, the ends of said padlock probe(s);
(e) subjecting said circularized padlock probe(s) to rolling circle amplification (RCA) using a DNA polymerase having 3'-5' exonuclease activity wherein if necessary said exonuclease activity digests the cDNA to generate a free 3' end which acts as a primer for said RCA; and
(f) detecting the rolling circle amplification product(s).

In some embodiments of the method, step (c) further comprises contacting said sample with padlock probes (l), wherein each is specific for wild-type Braf gene and have sequences:

$$Y1\text{-}X2\text{-}Z1\text{-}T \qquad (l)$$

where X2 is from 10-50 nucleotides.

In specific embodiments of the method, step (c) further comprises contacting said sample with padlock probes (l), wherein each is specific for wild-type Braf gene and have sequences:

$$Y1\text{-}X2\text{-}Z1\text{-}T \qquad (l)$$

where X2 is from 10-50 nucleotides and differs from X1.

In a further embodiment, the present invention provides a method for localized in situ detection of mRNA which codes for one or more mutations of the APC gene, PTEN gene, PI3K gene, KRAS gene codon 61 or codon 146, or KRAS gene 3'UTR in a sample of cells on a slide surface, comprising:
(a) generating cDNA from mRNA in the sample, wherein the primer is provided with a functional moiety capable of binding to or reacting with a cell or cellular component or an affinity binding group capable of binding to a cell or cellular component;
(b) adding a ribonuclease to said sample to digest the mRNA hybridized to said cDNA;
(c) contacting said sample with one or more padlock probes specific for mutations to the APC gene, PTEN gene, PI3K gene, KRAS gene codon 61 or codon 146, or KRAS gene 3'UTR, wherein each padlock probe comprises a sequence selected from the group consisting of:

$$Y1\text{-}X1\text{-}Z1\text{-}W \qquad (m)$$

where:
X1 is from 5-50 nucleotides;
Y1+Z1=20 to 40 nucleotides;
wherein Y1 comprises 5-20 nucleotides 3' to a point mutation in the APC gene, PTEN gene, PI3K gene, KRAS gene codon 61 or codon 146, or KRAS gene 3'UTR;
wherein Z1 comprises 5-20 nucleotides in the 5' to a point mutation in the APC gene, PTEN gene, PI3K gene, KRAS gene codon 61 or codon 146, or KRAS gene 3'UTR; and
wherein W is a nucleotide complementary to a point mutation in the APC gene, PTEN gene, PI3K gene, KRAS gene codon 61 or codon 146, or KRAS gene 3'UTR.

In some embodiments of the method step (c) further comprises contacting said sample with padlock probes (n), wherein each is specific for wild-type APC gene, PTEN gene, PI3K gene, KRAS gene codon 61 or codon 146, or KRAS gene 3'UTR and have sequences:

$$Y1\text{-}X2\text{-}Z1\text{-}V \qquad (n)$$

where X2 is from 10-50 nucleotides; and
wherein V is a nucleotide complementary to a wildtype sequence at the site of a point mutation in the APC gene, PTEN gene, PI3K gene, KRAS gene codon 61 or codon 146, or KRAS gene 3'UTR.

In specific embodiments of the method step (c) further comprises contacting said sample with padlock probes (n), wherein each is specific for wild-type APC gene, PTEN gene, PI3K gene, KRAS gene codon 61 or codon 146, or KRAS gene 3'UTR and have sequences:

$$Y1\text{-}X2\text{-}Z1\text{-}V \qquad (n)$$

where X2 is from 10-50 nucleotides and differs from X1; and
wherein V is a nucleotide complementary to a wildtype sequence at the site of a point mutation in the APC gene, PTEN gene, PI3K gene, KRAS gene codon 61 or codon 146, or KRAS gene 3'UTR.

In some embodiments, X1 and X2 each comprise at least one labeled nucleotide. In certain aspects of the invention, the label is fluorophore or a chromophore. In certain embodiments, each probe selected from (a)-(g), (k) and (m) has the same X1. In certain embodiments, each probe selected from (h)-(j), (l) and (n) has the same X2.

In certain embodiments of the method, the primer comprises 2'O-Me RNA, methylphosphonates or 2' Fluor RNA bases, peptidyl nucleic acid residues, or locked nucleic acid residues. In some embodiments, the sample comprises a fixed tissue section, a fresh frozen tissue, touch imprint samples or a cytological preparation comprising one or more cells.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9: Example of padlock probes for a Braf mutant and wild-type sequence.

DETAILED DESCRIPTION OF THE INVENTION

Figure 1:
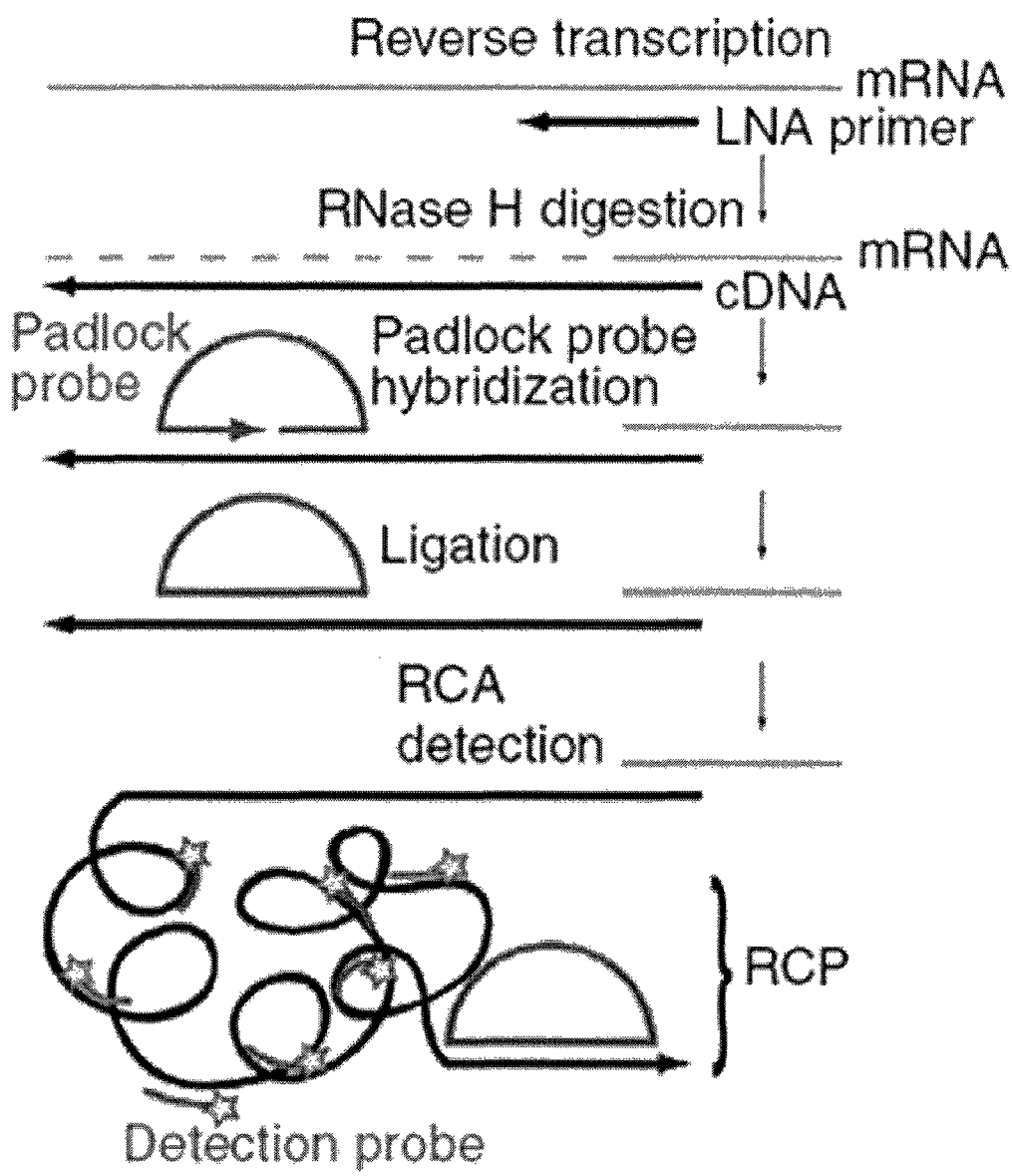
FIG. 1: Schematic representation of the detection of individual transcripts in situ with padlock probes and target-primed RCA. cDNA is created using locked nucleic acid (LNA)-modified primers and is probed after degradation of mRNA by RNase H. RCPs are identified through hybridization of fluorescent detection probes.
Figure 2:
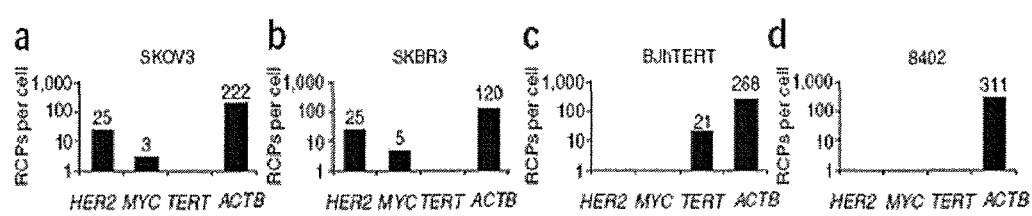
FIG. 2: Multiplex in situ detection of cancer-related transcripts in cancer and primary human cell lines. Quantification of RCPs in the different cell lines is shown in the bar graph: (a) human ovarian carcinoma cells (SKOV3); (b) human breast carcinoma cells (SKBR3); (c) TERT immortalized human fibroblast cells (BJhTERT); and (d) primary human fibroblast culture GM08402.

A. Localized Synthesis of cDNA from RNA Targets In Situ

As discussed above, the present invention relates to the detection of RNA, especially mRNA, in cells. The method involves the conversion of RNA to complementary DNA (cDNA) prior to the targeting of the cDNA with a padlock probe(s). The cDNA is synthesized in situ at the location of the template RNA. The reverse transcriptase (RT) primer may be modified so as to be capable of immobilization, and in particular immobilization to the cell. Thus it is contemplated that the primer may be provided with a functional moiety, or functional means (i.e. a "functionality"), which allows or enables the primer to be immobilized to a component in the sample, e.g. a cell or cellular component. This may be for example a functional moiety capable of binding to or reacting with a cell or a sample or cellular component. The use of such a primer, which becomes immobilized to the sample (e.g. to or in a cell), has the result that the cDNA product (which is generated by extension of the RT primer and is therefore contiguous with it) also becomes immobilized to the sample (e.g. to or in a cell).

Since the RCA, which is performed to generate the RCP which is ultimately detected, is carried out using the cDNA as primer (i.e. is a target-primed RCA) the RCP is contiguous with the cDNA and thus the RCP is also anchored or attached to the sample (e.g. cell). Thus, the use of such a primer ensures or allows that the RCP remains localized to the site of the RNA in the sample (e.g. in the cell). In other words localization of the RCP to the original site of the target RNA is preserved. In this way, localization of the signal reporting the target RNA is preserved and thus it can be seen that this favors and facilitates localized in situ detection.

Various such modifications of the RT primer are described herein and include, for example, the provision of reactive groups or moieties in the RT primer, e.g. chemical coupling agents such as a thiol group, NHS-esters, etc., which are capable of covalent attachment to the cells or cellular or other sample components, e.g. to proteins or other biomolecules in the cell, or to components in the sample e.g. matrix components in the sample. Alternatively or in addition, the primer may be provided with an affinity binding group capable of binding to a cell or cellular or sample component.

Although cells or cellular components provide a convenient point of attachment, or site of immobilization of the RT primer, this aspect of the invention is not restricted to immobilization on or within cells, and the RT primer may be immobilized to other components present in the sample, for example extracellular components. Indeed the components may be natural or synthetic and synthetic components may be added to the sample to supplement or to replace native cellular components. For example, a synthetic matrix may be provided to a cell or tissue sample to preserve signal localization in the method (namely to preserve localization of the RCP product which is detected). Indeed, rather than immobilizing the RT primer (as a means of immobilizing the cDNA), the synthesized cDNA itself or the target RNA may be immobilized in a synthetic matrix which is provided to the sample.

Thus for example, the target RNA or the synthesized cDNA may be attached to a synthetic gel matrix instead of the native cellular matrix to preserve the localization of the detection signals. This may be achieved by immersing the sample (e.g. the cells or tissue of the sample) in a gel solution which upon polymerization will give rise to a gel matrix to which the cDNA or target RNA can be attached. To achieve such attachment the RT primer may be provided with a reactive group or moiety which can react with the matrix material, for example at the 5' end thereof. This is described further below.

In a preferred modification, however, the primer is rendered resistant to the ribonuclease. Thus the primer may be modified to be ribonuclease-resistant. A ribonuclease is utilized to digest the RNA hybridized to the cDNA in an RNA:DNA duplex. As discussed below, in some embodiments the ribonuclease may be RNase H or a ribonuclease capable of digesting RNA in an RNA:DNA duplex. In a preferred embodiment of the invention, immobilization of the reverse transcriptase primer is achieved by virtue of it being ribonuclease resistant. In such a situation the ribonuclease cannot degrade the RNA which is hybridized to the RT primer. Thus the RT primer protects the primer binding site in the RNA from degradation. The RT primer accordingly remains bound to the RNA in the cell and in this way is immobilized in the cell. Modifications which may be made to the primer to render it ribonuclease-resistant are described below and include in particular the use of modified nucleotides, or nucleotide analogues for example nucleotides comprising 2'O-Me RNA, methylphosphonates, 2' fluor RNA bases, etc. which when incorporated into the primer, render the primer at least partially resistant to ribonuclease digestion. Alternatively or in addition, the primer may comprise locked nucleic acids (LNAs) or peptide nucleic acids (PNAs). Thus, in an embodiment of the invention, it is envisaged that the 5' end of the cDNA remains bound to the target RNA molecule via a ribonuclease resistant reverse transcriptase primer.

A "reverse transcription reaction" is a reaction in which RNA is converted to cDNA using the enzyme "reverse transcriptase" ("RT"), which results in the production of a single-stranded cDNA molecule whose nucleotide sequence is complementary to that of the RNA template. However, reverse transcription results in a cDNA that includes thymine in all instances where uracil would have occurred in an RNA complement. The reverse transcription reaction is typically referred to as the "first strand reaction" as the single-stranded cDNA may subsequently be converted into a double-stranded DNA copy of the original RNA by the action of a DNA polymerase (i.e. the second strand reaction). However, in the present method, a single cDNA strand is formed to act as a target for a sequence-specific padlock probe. The reverse transcription reaction is catalyzed by an enzyme that functions as an RNA-dependent DNA polymerase. Such enzymes are commonly referred to as reverse transcriptases. Reverse transcriptase enzymes are well known in the art and widely available. Any appropriate reverse transcriptase may be used and the choice of an appropriate enzyme is well within the skill of a person skilled in the art.

B. Padlock Probes

As mentioned above, the cDNA serves as a target for a padlock probe. Padlock probes are well known and widely used and are well-reported and described in the prior art. Thus the principles of padlock probing are well understood and the design and use of padlock probes is known and described in the art. Reference may be made for example to WO 99/49079. A padlock probe is essentially a linear circularizable oligonucleotide which has free 5' and 3' ends which are available for ligation, to result in the adoption of a circular conformation. It is understood that for circularization (ligation) to occur, the padlock probe has a free 5' phosphate group. To allow the juxtaposition of the ends of the padlock probe for ligation, the padlock probe is designed to have at its 5' and 3' ends regions of complementarity to its target sequence (in this case the synthesized cDNA molecule in the cell sample to be analyzed). These regions of complementarity thus allow specific binding of the padlock probe to its target sequence by virtue of hybridization to specific sequences in the target. Padlock probes may thus be designed to bind specifically to desired or particular targets. In the case of the method of the invention, the sequence of the cDNA target is defined by the sequence of the target RNA, i.e. the RNA molecule it is desired to detect. By hybridization to the cDNA target the ends of the padlock probe are brought into juxtaposition for ligation. As described in more detail below, the ligation may be direct or indirect. In other words, the ends of the padlock probe may be ligated directly to each other or they may be ligated to an intervening nucleic acid molecule/sequence of nucleotides. Thus the end regions of the padlock probe may be complementary to adjacent, or contiguous, regions in the cDNA product of step (a), or they may be complementary to non-adjacent (non-contiguous) regions of the cDNA (in which case, for ligation to occur, the "gap" between the two ends of the hybridized padlock probe is filled by an intervening molecule/sequence).

Upon addition to a sample, the ends of the padlock probe(s) hybridize to complementary regions in a cDNA molecule(s). Following hybridization, the padlock probe(s) may be circularized by direct or indirect ligation of the ends of the padlock probe(s) by a ligase enzyme. The circularized padlock probe is then subjected to RCA primed by the 3' end of the cDNA (i.e. the RCA is target-primed). A DNA polymerase with 3'-5' exonuclease activity is used. This permits the digestion of the cDNA strand in a 3'-5' direction to a point adjacent to the bound padlock probe. Alternatively, the cDNA may be of appropriate length and may act as the primer for the DNA polymerase-mediated amplification reaction without such digestion. In this way the 5' end of the RCP is advantageously continuous with the cDNA molecule. As a further alternative, instead of priming the RCA with the cDNA molecule, a separate primer that hybridizes to the padlock probe may be used in the reaction.

It will be understood by the skilled person that ribonuclease digestion of RNA, hybridization of padlock probes to the cDNA, ligation of the padlock probes, and RCA may be carried out sequentially or simultaneously. Thus, for example, the ribonuclease, the padlock probe(s), the ligase, and the DNA polymerase for RCA may be added to the sample sequentially or substantially at the same time. Furthermore, any combination of steps of the method can be carried out simultaneously and are contemplated within the scope of the invention such that the RCP produced by the method is capable of detection and is indicative of the presence, absence and/or nature of an RNA in a sample. For example, ribonuclease digestion of RNA and hybridization of the padlock probe may be carried out simultaneously, or in the same step, or ligation of the padlock probe and RCA may be carried out simultaneously, or in the same step.

The "complementary regions" of the padlock probe correspond to the 5' and 3' end regions of the probe which hybridize to the cDNA. The padlock probe is thus designed to bind to the cDNA in a target-specific manner. The padlock probe may be designed to detect the presence of a particular RNA, for example to determine if a particular gene is expressed. It may also be designed for genotyping applications, for example to detect the presence of particular sequence variants or mutants in a cell or tissue sample—padlock probes may be designed which are specific for particular known mutants of genes (e.g. known mutations in the KRAS gene, as described further below) or for the wild-type sequence and accordingly may be used to detect or determine the presence, or the distribution (within the context of a tissue sample) of particular mutations or sequence variants, etc.

Accordingly, based on principles which are known in the art, a padlock probe may be designed to bind to the cDNA at a site selected to detect the presence of a particular sequence or sequence variant in the corresponding RNA. The probes may be designed and used to verify or confirm the presence of particular mutations or sequence variations (e.g. targeted genotyping) or they may be used on a sample with unknown mutation/variant status, to detect whether or not a mutation/variant is present, and/or the specific nature of the mutation/variant (blinded genotyping). For example a mixture of padlock probes may be used, one designed to detect the wild-type, and one more others designed to detect specific mutations/variants. For such genotyping applications, padlock probes may be designed to have identical complementary regions, except for the last nucleotide at the 3' and/or 5' end, which differs according to the genotype the probe is designed to detect; the DNA ligase which is used for circularization of the padlock probe does not accept mismatches when joining the ends of the padlock probe and hence ligation will only occur when the probe hybridizes to a sequence which it "matches" at the said terminal nucleotide. In this way, single nucleotide differences may be discriminated.

In the hybridization reaction both ends of the padlock probe bind to the corresponding portion of, or region in, the cDNA such that they may become ligated, directly or indirectly, to each other resulting in circularization of the probe. Hybridization in this step does not require, but does include, 100% complementarity between said regions in the cDNA and the padlock probe. Thus "complementary", as used herein, means "functionally complementary", i.e. a level of complementarity sufficient to mediate a productive hybridization, which encompasses degrees of complementarity less than 100%. Thus, the region of complementarity between the cDNA and the region of the padlock probe may be at least 5 nucleotides in length, and is in some embodiments 10 or more nucleotides in length, e.g., 6, 7, 8, 9, 11, 12, 13, 14, 15, 16, 17, 18, 19, 20, 21, 22, 23, 24, 25, 26, 27, 28, 29, 30, 35, 40, 45, 50 or more nucleotides (and any range derivable therein). It may be up to 30, 40, 50, 60, 70, 80, 90 or 100 nucleotides in length (or any range derivable therein) in certain embodiments.

As noted above the ends of the padlock probe may be ligated directly or indirectly. "Direct ligation" of the ends of the padlock probe means that the ends of the probe hybridize immediately adjacently on the cDNA strand to form a substrate for a ligase enzyme resulting in their ligation to each other (intramolecular ligation). Alternatively, "indirect" means that the ends of the probe hybridize non-adjacently to the cDNA, i.e. separated by one or more intervening nucleotides. In such an embodiment said ends are not ligated directly to each other, but circularization of the probe instead occurs either via the intermediacy of one or more intervening (so-called "gap" or "gap-filling" (oligo)nucleotides) or by the extension of the 3' end of the probe to "fill" the "gap" corresponding to said intervening nucleotides (intermolecular ligation). Thus, in the former case, the gap of one or more nucleotides between the hybridized ends of the padlock probe may be "filled" by one or more "gap" (oligo)nucleotide(s) which are complementary to the intervening part of the cDNA. The gap may be a gap of 1 to 60 nucleotides or a gap of 1 to 40 nucleotides or a gap of 3 to 40 nucleotides. In specific embodiments, the gap may be a gap of 1, 2, 3, 4, 5, 6, 7, 8, 9, 10, 11, 12, 13, 14, 15, 16, 17, 18, 19, 20, 21, 22, 23, 24, 25, 27, 30, 32, 35, 37, 40, 42, 45, 47, 50, 52, 55, 57 or 60 nucleotides, of any integer (or range of integers) of nucleotides in between the indicated values. In further embodiments, the gap may have a size of more than 60 nucleotides. In further embodiments, the gap between said terminal regions may be filled by a gap oligonucleotide or by extending the 3' end of the padlock probe, e.g. a gap oligonucleotide as defined herein above. Circularization of the padlock probe thereby involves ligation of the ends of the probe to at least one gap (oligo)nucleotide, such that the gap (oligo)nucleotide becomes incorporated into the resulting circularized probe. Hence, in such an embodiment the template for the RCA contains the padlock probe and said gap (oligo)nucleotide. In such an embodiment, the intervening part of the cDNA may be of any length sufficient to allow a productive hybridization with the gap oligonucleotide, wherein by "productive hybridization", it is meant a hybridization capable of templating the indirect ligation (i.e. via the gap oligonucleotide) of the ends of the padlock probe. The padlock probe should be designed so that is does not contain any sequence which is complementary to the intervening part of the cDNA (i.e. the gap between the hybridized probe ends). The gap oligonucleotide may contain sequences useful for amplification or detection or sequencing, etc., of the eventual RCA product. Additionally or alternatively, the gap oligonucleotide may contain one or more tag or barcode sequences (discussed below). It will be seen that in a related embodiment more than one gap oligonucleotide might be used, which gap oligonucleotides hybridize to the intervening part of the cDNA in such a way that they, and the ends of the padlock probe, are ligated together end-to-end during the ligation step. In the latter case, the gap between the ends of the padlock probe hybridized to the cDNA may be filled by polymerase-mediated extension of the 3' end of the padlock probe. Suitable polymerases are known in the art. Once said 3' end has been extended as far as the 5' end of the padlock probe, the ends may be joined in a ligation reaction. Hybridization of the probe and/or the (oligo)nucleotide to the cDNA is advantageously dependent on the nucleotide sequence of the cDNA thus allowing for the sensitive, specific, qualitative and/or quantitative detection of one or more cDNA, and by extension the corresponding RNA nucleotide sequences.

C. Samples

The methods and compositions disclosed herein may be used to evaluate RNA in any sample of cells in which an RNA molecule may occur, so long as the sample is amenable to in situ detection. A representative sample may comprise a fixed tissue section, a fresh frozen tissue or a cytological preparation comprising one or more cells. The sample may be permeabilized to render the RNA accessible. Appropriate means to permeabilize cells are well known in the art and include for example the use of detergents, e.g. appropriately diluted Triton X-100 solution, e.g. 0.1% Triton X-100, or Tween, 0.1% Tween, or acid treatment e.g. with 0.1M HCl. Permeabilization of tissue samples may also comprise treatment of the sample with one or more enzymes, e.g. pepsin, proteinase K, trypsinogen, or pronase, etc. Also, microwave treatment of the sample may be carried out as described in the art.

The sample may also be treated to fix RNA contained in the cells to the sample, for example to fix it to the cell matrix. Such procedures are known and described in the art. For example, in the field of in situ hybridization, reagents are known for fixing mRNA to cells. In particular, 5' phosphate groups in the RNA may be linked to amines present on proteins in the cellular matrix via EDC-mediated conjugation (EDC: 1-ethyl-3-(3-dimethylaminopropyl)carbodiimide), thus helping to maintain the localization of the RNA relative to other cellular components. Such a technique has previously been described in relation to microRNAs and their detection via in situ hybridization (Pena et al., 2009).

D. Localized In Situ Detection

The next step of the method following the RCA step is to determine the presence of the extended product (i.e. the RCA product or RCP) in the reaction mixture in order to detect the target RNA in the sample. In other words, the sample is screened, etc. (i.e., assayed, assessed, evaluated, tested, etc.) for the presence of any resultant RCP in order to detect the presence of the target RNA in the sample being tested. The RCP produced by the methods described herein may, in the broadest sense, be detected using any convenient protocol. The particular detection protocol may vary depending on the sensitivity desired and the application in which the method is being practiced. In one embodiment, the RCP detection protocol may include an amplification component, in which the copy number of the RCA product (or part thereof) is increased, e.g., to enhance sensitivity of the particular assay, but this is not generally necessary. Thus the RCP may be directly detected without any amplification.

The localized detection may be viewed as comprising two steps, firstly the development of a detectable signal and secondly the read-out of the signal. With respect to the first step, the following detection methods could be contemplated. The signal may include, but is not limited to a fluorescent, chromogenic, radioactive, luminescent, magnetic, electron density or particle-based signal. Thus, a label directly or indirectly providing such a signal may be used. The signal could be obtained either by incorporating a labeled nucleotide during amplification to yield a labeled RCP, using a complementary labeled oligonucleotide that is capable of hybridization to the RCP (a "detection probe"), or to, in a sequence non-specific manner, label the produced nucleic acid. The label could be direct, (e.g. but not limited to: a fluorophore, chromogen, radioactive isotope, luminescent molecule, magnetic particle or Au-particle), or indirect (e.g. but not limited to an enzyme or branching oligonucleotide). The enzyme may produce the signal in a subsequent or simultaneous enzymatic step. For example horseradish peroxidase may be provided as a label which generates a signal upon contact with an appropriate substrate. Several methods are well described in the literature and are known to be used to render signals that are detectable by various means (which may be used in the second step), e.g. microscopy (bright-field, fluorescent, electron, scanning probe), flow cytometry (fluorescent, particle, magnetic) or a scanning device.

In a particular embodiment, detection is by means of labeled oligonucleotide probes ("detection probes") which have complementarity, and thereby hybridize, to the RCP. Such labeling may be by any means known in the art, such as fluorescent labeling including ratiolabeling, radiolabeling, labeling with a chromogenic or luminescent substrate or with an enzyme e.g. horseradish peroxidase, etc. Fluorescently-labeled probes are preferred. The signal produced by the labels may be detected by any suitable means, such as visually, including microscopically. As the RCPs are comprised of repeated "monomers" corresponding to the padlock probe (optionally with additional incorporated nucleotides or gap oligonucleotides, as discussed above), the sequences to which the oligonucleotide probes hybridize will be "repeated", i.e. assuming the RCA reaction proceeds beyond a single replication of the template, multiple sites for hybridization of the oligonucleotide probes will exist within each RCP. In this way, the signal intensity from the label on the oligonucleotide probes may be increased by prolonging the RCA reaction to produce a long RCA product containing many hybridization sites. Signal intensity and localization is further increased due to spontaneous coiling of the RCP. The resulting coils, containing multiple hybridized oligonucleotide probes, give a condensed signal which is readily discernible by, for example, microscopic visualization against a background of non-hybridized oligonucleotide probes. Hence, it may be possible qualitatively or quantitatively to detect the RNA(s) in a sample without performing a washing step to remove unhybridized oligonucleotide probes.

Multiplexed detection may be facilitated by using differently-labeled oligonucleotide probes for different RNAs, wherein the respective oligonucleotide probes are designed to have complementarity to "unique" sequences present only in the RCPs (corresponding to sequences present only in the padlock probes) for the respective RNAs. Such sequences may be barcode or tag sequences, as discussed above. In a particular embodiment, two or more differentially labeled detection oligonucleotides may be used to detect one or more RCPs, one labeled detection oligonucleotides reporting the wild-type variant of a gene and another labeled detection oligonucleotide(s) reporting one or more mutant variants of the gene. Different fluorophores may be used as the labels. Multiplexed detection can also be achieved by applying in situ sequencing technologies such as sequencing by ligation, sequencing by synthesis, or sequencing by hybridization.

The present method allows for single nucleotide resolution in the detection of RNA nucleotide sequences. The present method may thus be used for the detection of one or more point mutations in an RNA or indeed any single-nucleotide variant. Thus the method may find utility in the detection of allelic variants or alternative splicing, etc. The superior sensitivity and localization afforded by the method also means that it may be used to detect RNA in single cells. For example, multiplex detection of mRNA transcripts by the method of the invention may advantageously be used for expression profiling, including in a single cell.

As will be appreciated by the skilled person, the present method may be used in various diagnostic applications, in particular those that require single nucleotide sensitivity. For example, this method may be used to detect point mutations which are associated with disease, disease risk or predisposition, or with responsiveness to treatment, etc., e.g. activating mutations in oncogenes.

The method of the present invention may be adapted for automation, for example applying procedures as used in conventional automated FISH assays.

E. KRAS

As described in more detail herein, the method of the invention may be used to detect a point mutation in the mRNA sequence that codes for KRAS. KRAS is one of the most frequently activated oncogenes. As used herein, "KRAS" refers to v-Ki-ras2 Kirsten rat sarcoma viral oncogene homolog. KRAS is also known in the art as NS3, KRAS1, KRAS2, RASK2, KI-RAS, C-K-RAS, K-RAS2A, K-RAS2B, K-RAS4A and K-RAS4B. This gene, a Kirsten ras oncogene homolog from the mammalian ras gene family, encodes a protein that is a member of the small GTPase superfamily. A single amino acid substitution can be responsible for an activating mutation. The transforming protein that results can be implicated in various malignancies, including lung cancer, colon cancer, thyroid cancer and pancreatic cancer and is strongly associated with resistance to epidermal growth factor receptor (EGFR) inhibitor therapy. For example, in metastatic colorectal cancer the presence of mutations in the KRAS gene is routinely analyzed, and a positive mutation status indicates that the tumor will not respond to EGFR antibody therapy. In lung adenocarcinoma KRAS mutations are associated with smoking, poor prognosis and non-responsiveness to EGFR tyrosine kinase inhibitors (TKI) whereas KRAS wild-type tumors with EGFR mutations are linked to non-smoking, better prognosis and response to EGFR-TKI therapy.

A tumor may have one or more mutations in KRAS (e.g., an activating mutation), unwanted expression of KRAS (e.g., overexpression over wild type), KRAS deficiency, and/or amplification of KRAS gene (e.g., having more than two functional copies of KRAS gene). There are seven point mutations in codon 12 and 13 that together account for more than 95% of all KRAS mutations. Conventional KRAS analysis is based on DNA extracted from crude tumor tissue, and after PCR amplification of the hot spot region on exon 1 the sequence aberrations in codon 12 and 13 are characterized by direct dideoxy sequencing or by more sensitive targeted assays such as Pyrosequencing or allele-specific PCR. Thus, all different cell types present in a tumor sample—normal parenchymal cells, stromal cells, inflammatory cells, different pre-neoplastic and neoplastic sub-clones—contribute their wild-type and mutated KRAS alleles to these assays. In the routine diagnostic setting tumor cells can be enriched for by manual microdissection, but in order to annotate a mutation to a certain tumor sub compartment the required dissection is laborious. Still, single cell resolution is extremely difficult to achieve. This might not be a problem in colorectal cancer as activating KRAS mutations are considered to be early events in tumorigenesis and presumably homogenously distributed in the tumor. However, for other types of cancer, and for mutations in other oncogenes, very little is known about heterogeneity among cancer sub-clones and its impact on tumor biology and treatment response. Therefore, methods which offer genotyping directly on tissue sections are highly warranted. Hence there is a requirement for sensitive KRAS mutation analysis to determine the most suitable treatment for the patients.

As described herein the present method may be used in a genotyping assay that targets KRAS-mutations in codon 12 and 13 in situ on tissue samples by the use of multiple mutation specific padlock probes and rolling-circle amplification. Such an in situ technique offers single transcript analysis directly in tissues and thus circumvents traditional DNA extraction from heterogeneous tumor tissues. In addition, or alternatively, mutations in codon 61 and/or codon 146 of KRAS may be targeted (for specific information see also Loupakis et al., 2009, Br J Cancer, 101(4): 715-21, which is incorporated herein by reference in its entirety). Furthermore, mutations in the 3' UTR of KRAS transcripts may be targeted (for specific information see also Graziano et al., 2010, Pharmacogenomics J., doi 10.1038/tpj.2010.9, which is incorporated herein by reference in its entirety). These mutations may be detected in combination with a detection of codon 12, 13, 61 and/or 146 mutations, or they may be detected alone, or in combination with codon 12 mutations, or with codon 13 mutations, or with codon 61 mutations, or with codon 146 mutation, or with any subgrouping of codon 12, 13, 61 and 146 mutations. Methods may be carried out in fresh frozen or formalin-fixed, paraffin-embedded (FFPE) tissue, or in tissues in touch imprint samples. In some embodiments, tissue samples may be cancer tissue, e.g. colon or lung tissues.

In some embodiments, methods and compositions concern KRAS mutations, particularly those mutations that have been found in cancer cells. The term "KRAS mutation associated with cancer" or "KRAS mutant associated with tumor development" refers to a mutation in the KRAS gene or a corresponding mutant, that has been identified in the Sanger database as of Feb. 15, 2012 as associated with cancer or precancer (on the world wide web at sanger.ac.uk). In certain embodiments, the methods and compositions concern detecting a plurality of mutations. In some embodiments a plurality of mutations refers to at least or at most the following percentage of mutations in that gene associated with cancer: 5, 10, 15, 20, 25, 30, 35, 40, 45, 50, 55, 60, 65, 70, 75, 80, 85, 90, 95, 96, 97, 98, 99 or 100%, or any range derivable therein.

F. EGFR

The epidermal growth factor receptor (EGFR) is an important target in the treatment of some cancers. The combination of anti-EGFR antibodies with chemotherapy is thus commonly used in the treatment of these cancers. The KRAS protein is an important mediator in the signal transduction cascade regulated by the EGFR. Mutations in the KRAS gene are a very important factor in the selection of molecular biological treatment options targeted against EGFR. Studies have shown that if the mutation is present, anti-EGFR medications such as cetuximab (Erbitux) and panitumumab (Vectibix) are not sufficiently effective to warrant their use. Thus, as discussed herein, the present method may advantageously be used to detect the presence or absence of a point mutation in the mRNA which codes for KRAS, wherein the identification of KRAS wild-type mRNA indicates that the cancer may be treated with EGFR inhibitors.

In addition, the present method may be used to detect the presence or absence of a mutation in the mRNA which codes for the EGFR. Examples of EGFR mutations that may be detected according to the present invention are shown in Table 7.

G. Braf, APC, PTEN, PI3K

The method of the invention may be further used to detect one or more point mutations in the mRNA sequence that codes for Braf, APC, PTEN or PI3K. Suitable Braf mutations are known to the skilled person and are described in Rajagopalan et al., 2002, Nature, 418 (29), 934 and Monticone et al., 2008, Molecular Cancer, 7(92), which are incorporated herein by reference in their entirety. Particularly preferred is the detection of mutation V600E. The method of the invention further envisages the detection of one or more point mutations in KRAS and Braf. Braf and KRAS mutations are described as being mutually exclusive regarding the function of downstream pathway elements. Thus, by determining mutations in Braf and KRAS at the same time, it may be elucidate whether and pathway functions are compromised by genetic mutations.

Suitable APC mutations are known to the skilled person and are described, for example, in Vogelstein and Fearon, 1988, N Engl J Med, 319(9): 525-32, which is incorporated herein by reference in its entirety.

Suitable PTEN mutations are known to the skilled person and are described, for example, in Laurent-Puig et al, 2009, J Clon Oncol, 27(35), 5924-30 or Loupakis et al., 2009, J clin Oncol, 27(16), 2622-9, which are incorporated herein by reference in their entirety.

Suitable PI3K mutations are known to the skilled person and are described, for example, in Satore-Bianchi et al., 2009, Cancer Res., 69(5), 1851-7 or Prenen et al., 2009, Clin Cancer Res., 15(9), 3184-8, which are incorporated herein by reference in their entirety.

In some embodiments, methods and compositions concern Braf APC, PTEN or PI3K mutations. In further embodiments, methods and compositions concern KRAS mutations in combination with Braf mutations, and/or in combination with APC mutations, and/or in combination with PTEN mutations, and/or in combination with PI3K mutations, particularly those mutations that have been found in cancer cells. Such mutations may be derived from suitable literature sources, e.g. those mentioned above, or may be identified according to suitable databases, e.g. the Sanger database as of Feb. 15, 2012 (on the world wide web at sanger.ac.uk). In certain embodiments, the methods and compositions concern detecting a plurality of said mutations. In some embodiments a plurality of mutations refers to at least or at most the following percentage of mutations in that said gene or gene combination associated with cancer: 5, 10, 15, 20, 25, 30, 35, 40, 45, 50, 55, 60, 65, 70, 75, 80, 85, 90, 95, 96, 97, 98, 99 or 100%, or any range derivable therein.

H. Kits

The invention also provides kits for use in the method of the invention. The kit may comprise at least one (species of) padlock probe, as defined above, specific for a particular cDNA. Such a kit may also comprise RT primer(s), an RT enzyme, a ribonuclease, a DNA polymerase, a ligase and/or means of detection of RCA product.

The kit may optionally further comprise one or more gap oligonucleotides with complementarity to the portion of the target cDNA which lies between non-adjacently-hybridized padlock probe ends or may comprise reagents for otherwise filling any gap present when the ends of the padlock probe are hybridized to the cDNA, such as a polymerase, nucleotides and necessary co-factors. In some embodiments, the kit may further comprises a primer oligonucleotide for priming RCA of the padlock probe. In certain aspects, the primer hybridizes to the padlock probe at a location other than the region(s) of the padlock probe that is complementary to the target cDNA.

Alternatively or additionally, the kit may comprise a ligase for circularizing the padlock probe(s) (which may or may not be present in the kit) or a polymerase such as phi29 polymerase (and optionally necessary cofactors, as well and nucleotides) for effecting RCA. Reagents for detecting the RCA product may also be included in the kit. Such reagents may include a labeled oligonucleotide hybridization probe having complementarity to a portion of a padlock probe, or to a portion of a gap oligonucleotide, present in the kit.

The kit may be designed for use in multiplex embodiments of the method of the invention, and accordingly may comprise combinations of the components defined above for more than target RNA. If probes having binding specificity respectively for a plurality of cDNA species are present in the kit, the kit may additionally comprise components allowing multiple RNA detection in parallel to be distinguished. For example, the kit may contain padlock probes for different cDNA targets, wherein said cDNA targets have "unique" sequences for hybridization only to a particular species of probe. Such padlock probes may for example carry different tag or identifier sequences allowing the detection of different RNAs to be distinguished.

The kit may be designed for use in the detection of an mRNA coding for KRAS. In some embodiments, the kit may contain one or more padlock probes that target cDNA reverse transcribed from the wild-type KRAS mRNA and/or one or more padlock probes which target cDNA reverse transcribed from a KRAS mRNA molecule comprising a point-mutation.

In addition to the above components, the kit may further include instructions for practicing the method of the invention. These instructions may be present in the kit in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a remote site. Any convenient means may be present in the kit.

Thus, in a further aspect the present invention provides a kit for use in the localized in situ detection of a target RNA in a sample, said kit comprising one or more components selected from the list comprising:

(i) a padlock probe comprising 3' and 5' terminal regions having complementarity to cDNA transcribed from said target RNA (such regions can alternatively be defined as corresponding in sequence to regions of said target RNA, which regions as defined above may be adjacent or non-adjacent);

(ii) a reverse transcriptase primer capable of hybridizing to said target RNA (e.g. capable of hybridizing specifically to said RNA);

(iii) a reverse transcriptase;

(iv) a ribonuclease;

(v) a ligase;

(vi) a polymerase having 3' exonuclease activity;

(vii) a gap oligonucleotide capable of hybridizing to a portion of a cDNA transcribed from said target RNA;

(viii) a detection probe capable of hybridizing to a complement of a padlock probe of (i); or to a complement of a gap oligonucleotide of (vii);

(ix) nucleotides for incorporation e.g. dNTPs.

The detection probe of (viii) may be a labeled detection oligonucleotide capable of hybridizing to the amplification product (which will contain a complement of a padlock probe of (i) or a complement of a gap oligonucleotide of (vii)). For example the detection oligonucleotide may be fluorescently labeled or may be labeled with a horse radish-peroxidase.

In one embodiment the kit may contain the padlock probe of (i) and optionally one or more further components selected from any one of (ii) to (ix). Other combinations of kit components are also possible. For example the kit may contain the padlock probe of (i) and at least one of the reverse transcriptase primer of (ii), the reverse transcriptase of (iii) and the ribonuclease of (iv), optionally with one or more further components selected from any one of (ii) or (iii) or (iv) to (ix). Other representative kits of the invention may include the reverse transcriptase primer of (ii), and at least one of components (iii) to (ix), more particularly the primer of (ii) with at least one of components ((iii) to (vi), and optionally with one or more further components selected from any one of (i) or (vii) to (ix). Also included by way of representative example is a kit comprising at least two, or at least three, or all four, of components (iii) to (vi), optionally together with one or more further components selected from (i), (ii), or (vii) to (ix). All possible combinations of 2 or 3 components selected from (iii) to (iv) are covered. For example, such an embodiment may include (iii), (iv) and (v), or (iii), (v) and (vi), or (iii), (iv) and (vi) and so on.

I. Tables

TABLE 1

Oligonucleotide sequences

|  | Name | Sequence | SEQ NOS: |
|---|---|---|---|
| cDNA primers | p-βe1[a] | A + TC + AT + CC + AT + GG + TG + AGCTGGCGGCGG | 32 |
|  | P-βhum[a] | C + TG + AC + CC + AT + GC + CC + ACCATCACGCCC | 33 |
|  | P-βmus | C + TG + AC + CC + AT + TC + CC + ACCATCACACCC | 34 |
|  | P-βe6 | T + TA + GA + GA + GA + AG + TG + GGGTGGCTTTTA | 35 |
|  | P-cMyc[a] | G + CG + TC + CT + TG + CT + CG + GGTGTTGTAAGTTCCAG | 36 |
|  | P-HER2[a] | G + AG + CT + GG + GT + GC + CT + CGCACAATCCGCAGCCT | 37 |
|  | P-TERT[a] | A + GG + AC + AC + CT + GG + CG + GAAGGAGGGGCGGCGG | 38 |
|  | P-α1βmus[a] | A + CT + CG + TC + AT + AC + TC + CTGCTTGCTGATCCACA | 39 |
|  | P-γ1mus[a] | G + CC + TC + AG + GA + AA + TC + CTGGAAGTCTGC | 40 |
| Padlock probes (detection probe) | PLP-βGe1[b] (DP-1) | AGCCTCGCCTTTGCCTTCCTTTTACGACCTCAATGCTG CTGCTGTACTACTCTTCGCCCCGCGAGCACAG | 41 |
|  | PLP-βhum[a] (DP-4) | GCCGGCTTCGCGGGCGACGATTCCTCTATGATTACTG ACCTATGCGTCTATTTAGTGGAGCCTCTTCTTTACGGC GCCGGCATGTGCAAG | 42 |
|  | PLP-βmus[a] (DP-5) | GCCGGCTTCGCGGGCGACGATTCCTCTATGATTACTG ACCTAAGTCGGAAGTACTACTCTCTTCTTCTTTACGGC GCCGGCATGTGCAAA | 43 |
|  | PLP-βf3e6[a] (DP-1) | TACAGGAAGTCCCTTGCCATTTCCTCTATGATTACTGA CCTACCTCAATGCTGCTGCTGTACTACTCTTCCCAAAG ATGAGATGCGTTGT | 44 |
|  | PLP2-βmus[c] (DP-3) | CTGTCCACCTTCCAGAGAGTGTACCGACCTCAGTAAG TAGCCGTGACTATCGACTTCCAGCCTGGCCTCA | 45 |
|  | PLP-α1mus[c] (DP-2) | CTGTCCACCTTCCAGCCTTTCCTACGACCTCAATGCAC ATGTTTGGCTCCTCTTCTCCAGCCTGGCCTCG | 46 |
|  | PLP-γ1mus[a] (DP-1) | CCCCAGCCTGGTGGAAGCTAGCTACCTCAATGCTGCT GCTGTACTACTATGACTGCTGGAGATGAGAAAG | 47 |
|  | PLP-cMyc[c] (DP-4) | CGAAACTTTGCCCATAGCAGATTGGAACGTTTAAATG CGTCTATTTAGTGGAGCCGAGACAATCTTACATCGCA ACCCTTGCCGCATCCA | 48 |
|  | PLP-HER2[c] (DP-5) | TGCCAGCCTGTCCTTCCTGCATCGTCTTAATCACTAGT CGGAAGTACTACTCTCTTACGCTTACAACTAGCTCAC CTACCTGCCCACCAA | 49 |
|  | PLP-TERT[c] (DP-2) | GGTGTGCGTGCCCTGGGACGACTTTCTATGATTACTG ACCTACCTCAATGCACATGTTTGGCTCCTCTTCGCGCT GGTGGCCCAGTGCCT | 50 |
|  | PLP-KRAS-wtGGT[3] (DP-3) | GGCGTAGGCAAGAGTTCCTGTAGTAAAGTAGCCGTGA CTATCGACTGAATCTAAGGTAGTTGGAGCTGGT | 51 |
|  | PLP-KRAS-mutGAT[3] (DP-5) | GGCGTAGGCAAGAGTGTAAGTCATCAAGTCGGAAGT ACTACTCTCTGAATCTAAGGTAGTTGGAGCTGTT | 52 |
| Detection probes | DP-1Cy3[d] | Cy3-CCTCAATGCTGCTGCTGTACTAC | 53 |
|  | DP-1Cy3.5[a] | TexasRed-CCTCAATGCTGCTGCTGTACTAC | 53 |
|  | DP-2FITC[a] | FITC-CCTCAATGCACATGTTTGGCTCC | 54 |
|  | DP-2Cy5[9] | Cy5-CCTCAATGCACATGTTTGGCTCC | 54 |
|  | DP-3[d] | Cy3-AGTAGCCGTGACTATCGACT | 55 |
|  | DP-4[c] | Cy3-TGCGTCTATTTAGTGGAGCC | 56 |
|  | DP-5[d] | Cy5-AGTCGGAAGTACTACTCTCT | 57 |
| qPCR primers | ACTBfwd[b] | CTGGAACGGTGAAGGTGACA | 58 |
|  | ACTBrev[b] | CGGCCACATTGTGAACTTTG | 59 |

Oligonucleotides are given in 5'-3' order + symbol denotes the LNA bases
Oligonucleotides were purchased from Integrated DNA Technologies[3], DNA technology A/S[b], Biomers[c] and Eurogentec[d]

TABLE 2

Sequences of cDNA primers for LNA content investigation

| Primer | LNA content | Sequence | SEQ NOS: |
|---|---|---|---|
| P-unmod | No LNA | ATCATCCATGGTGAGCTGGCGGCGG | 32 |
| P-LNA1 or P-βe1 | 7 LNA, every 2nd | A + TC + AT + CC + AT + GG + TG + AGCTGGCGGCGG | 32 |

TABLE 2-continued

Sequences of cDNA primers for LNA content investigation

| Primer | LNA content | Sequence | SEQ NOS: |
|---|---|---|---|
| P-LNA2 | 7 LNA, every 2$^{nd}$ | A + TC + AT + CC + AT + GG + TG + AG CTGGCGGCGGGTGTG | 60 |
| P-LNA3 | 9 LNA, every 2$^{nd}$ | A + TC + AT + CC + AT + GG + TG + AG + CT + GGCGGCGGGTGTG | 60 |
| P-LNA4 | 5 LNA, every 2$^{nd}$ | A + TC + AT + CC + AT + GGTGAGCTGGCGGCGGGTGTG | 60 |
| P-LNA5 | 5 LNA, every 3$^{rd}$ | AT + CAT + CCA + TGG + TGA + GCTGGCGGCGGGTGTG | 60 |

Oligonucleotides are given in 5'-3' order. + symbol denotes the LNA bases.
All LNA containin Oligonucleotides were purchased from Integrated DNA Technology. The unmodified primer was purchased from Biomers.

TABLE 3

Sequences of cDNA primers for investigation of cDNA synthesis length

| Primer | Sequence | SEQ NOS: |
|---|---|---|
| P-93 nt or P-βe1 | A + TC + AT + CC + AT + GG + TG + AGCTGGCGGCGG | 32 |
| P-141 nt | G + GC + CT + TG + CA + CA + TG + CCGGAGCCGTTGTCGAC | 61 |
| P-231 nt or P-βhum | C + TG + AC + CC + AT + GC + CC + ACCATCACGCCC | 33 |
| P-261 nt | C + TG + GG + CC + TC + GT + CG + CCCACATAGGAATCCTT | 62 |
| P-501 nt | C + AC + AG + CC + TG + GA + TA + GCAACGTACATGGCTGG | 63 |

Oligonucleotides are given in 5'-3' order. + symbol denotes the LNA base
Oligonucleotides were purchased from Integrated DNA Technology.
The primer name indicates the maximum length o the produced cDNA for each respective cDNA primer.

TABLE 4

Oligonucleotide sequences for genotyping of KRAS mutations

| | Oligonucleotide sequences | SEQ ID NOs |
|---|---|---|
| Primers | Sequences (5'-3') | |
| P-KRAS-c12/13[b] | T + GT + AT + CG + TC + AA + GG + CACTCTT | 64 |
| P-KRAS-c12/13-II[a] | C + CT + CT + AT + TG + TT + GG + ATCATATTCGTC | 65 |
| P-KRAS-Q61H[b] | T + AT + TC + GT + CC + AC + AA + AATGATTCTGAA | 66 |
| P-EGFR-L858R[b] | T + CT + TT + CT + CT + TC + CG + CACCCAG | 67 |
| P-EGFR-S768I[b] | G + GC + GG + CA + CA + CGTGGGGTTG | 68 |
| P-EGFR-G719C/A[b] | C + CT + TA + TA + CA + CC + GT + GCCGAAC | 69 |
| P-TP53-S127F[b] | A + GT + TG + GC + AA + AA + CA + TCTTGTTGAGGG | 70 |
| P-TP53-P190S[b] | T + TC + CT + TC + CA + CT + CG + GATAAGATGCTG | 71 |
| P-ACTB[b] | G + TG + GA + CG + GG + CG + GC + GGATCGGCAAAG | 72 |
| P-ACTB-II[b] | A + TC + AT + CC + AT + GG + TG + AGCTGGCGGCGG | 73 |
| Padlock probes | Sequences (5'-3') | |
| PP-KRAS-wt1[a] (DP-1) | GTGGCGTAGGCAAGATCCTAGTAATCAGTAGCCGTGACTATCGAC TGGTTCAAAGTGGTAGTTGGAGCTG | 74 |
| PP-KRAS-G12S[a] (DP-2) | GTGGCGTAGGCAAGATTCTAGATCCCTCAATGCACATGTTTGGCTC CGGTTCAAGTGGTAGTTGGAGCTA | 75 |
| PP-KRAS-G12R[a] (DP-2) | GTGGCGTAGGCAAGATTCTAGATCCCTCAATGCACATGTTTGGCTC CGGTTCAAGTGGTAGTTGGAGCTC | 76 |
| PP-KRAS-G12C[a] (DP-2) | GTGGCGTAGGCAAGATTCTAGATCCCTCAATGCACATGTTTGGCTC CGGTTCAAGTGGTAGTTGGAGCTT | 77 |

TABLE 4-continued

Oligonucleotide sequences for genotyping of KRAS mutations

| | Oligonucleotide sequences | SEQ ID NOs |
|---|---|---|
| PP-KRAS-wt2[a] (DP-1) | TGGCGTAGGCAAGAGTCCTAGTAAT*CAGTAGCCGTGACTATCGAC* TGGTTCAAAGGGTAGTTGGAGCTGG | 78 |
| PP-KRAS-G12D[a] (DP-2) | TGGCGTAGGCAAGAGTTCTAGATCCCTCAATGCACATGTTTGGCTC CGGTTCAAGGGTAGTTGGAGCTGA | 79 |
| PP-KRAS-G12V[a] (DP-2) | TGGCGTAGGCAAGAGTTCTAGATCCCTCAATGCACATGTTTGGCTC CGGTTCAAGGGTAGTTGGAGCTGT | 80 |
| PP-KRAS-G12A[a] (DP-2) | TGGCGTAGGCAAGAGTTCTAGATCCCTCAATGCACATGTTTGGCTC CGGTTCAAGGGTAGTTGGAGCTGC | 81 |
| PP-KRAS-wt3[a] (DP-1) | CGTAGGCAAGAGTGCTCCTAGTAAT*CAGTAGCCGTGACTATCGAC* TGGTTCAAAGAGTTGGAGCTGGTGG | 82 |
| PP-KRAS-G13D[a] (DP-2) | CGTAGGCAAGAGTGCTTCTAGATCCCTCAATGCACATGTTTGGCTC CGGTTCAAGAGTTGGAGCTGGTGA | 83 |
| PP-KRAS-wt4[a] (DP-1) | GAGGAGTACAGTGCATCCTAGTAATCAGTAGCCGTGACTATCGAC TGGTTCAAAGGACACAGCAGGTCAA | 84 |
| PP-KRAS-Q61H[a] (DP-2) | GAGGAGTACAGTGCACGCTAGATCCCTCAATGCACATGTTTGGCT CCGGTTCAAGGACACAGCAGGTCAT | 85 |
| PP-EGFR-wt1[a] (DP-1) | GGCCAAACTGCTGGGTCCTAGTAATCAGTAGCCGTGACTATCGAC TGGTTCAAAGCACAGATTTTGGGCT | 86 |
| PP-EGFR-L858R[a] (DP-3) | GGCCAAACTGCTGGGTTCTAGATACCTCAATGCTGCTGCTGTACTA CGGTTCAAGCACAGATTTTGGGCG | 87 |
| PP-EGFR-wt2[a] (DP-1) | CGTGGACAACCCCCATCCTAGTAATCAGTAGCCGTGACTATCGAC TGGTTCAAAGCTACGTGATGGCCAG | 88 |
| PP-EGFR-S768I[a] (DP-3) | CGTGGACAACCCCCATTCTAGATACCTCAATGCTGCTGCTGTACTA CGGTTCAAGCTACGTGATGGCCAT | 89 |
| PP-EGFR-wt3[a] (DP-1) | GCTCCGGTGCGTTCGTCCTAGTAATCAGTAGCCGTGACTATCGACT GGTTCAAAGAGATCAAAGTGCTGG | 90 |
| PP-EGFR-G719C[a] (DP-2) | GCTCCGGTGCGTTCGTTCTAGATCCCTCAATGCACATGTTTGGCTC CGGTTCAAGAGATCAAAGTGCTGT | 91 |
| PP-EGFR-wt4[a] (DP-1) | CTCCGGTGCGTTCGTCCTAGTAATCAGTAGCCGTGACTATCGACT GGTTCAAAGGATCAAAGTGCTGGC | 92 |
| PP-EGFR-G719A[a] (DP-2) | CTCCGGTGCGTTCGGTTCTAGATCCCTCAATGCACATGTTTGGCTC CGGTTCAATGATCAAAGTGCTGGG | 93 |
| PP-TP53-wt1[a] (DP-3) | CCCTGCCCTCAACAATTCCTTTTACGACCTCAATGCTGCTGCTGTA CTACTCTTCGACTTGCACGTACTC | 94 |
| PP-TP53-S127F[a] (DP-4) | CCCTGCCCTCAACAACTAGTATCTGAGTCGGAAGTACTACTCTCTT GTGCCATAAGACTTGCACGTACTT | 95 |
| PP-TP53-wt2[a] (DP-3) | CTCCTCAGCATCTTATTCCTTTTACGACCTCAATGCTGCTGCTGTA CTACTCTTCGCGATGGTCTGGCCC | 96 |
| PP-TP53-P190S[a] (DP-4) | CTCCTCAGCATCTTACTAGTATCTGAGTCGGAAGTACTACTCTCTT GTGCCATAAGCGATGGTCTGGCCT | 97 |
| PP-ACTB[a] (DP-3) | AGCCTCGCCTTTGCCTTCCTTTTACGACCTCAATGCTGCTGCTGTA CTACTCTTCGCCCCGCGAGCACAG | 98 |
| PP-ACTB-II[a] (DP-2) | AGCCTCGCCTTTGCCTTCCTTTTACGACCTCAATGCACATGTTTGG CTCCTCTTCGCCCCGCGAGCACAG | 99 |

| Detection probes | Sequences (5'-3') | |
|---|---|---|
| DP-1[d] | AGTAGCCGTGACTATCGACT | 55 |
| DP-2[d] | CCTCAATGCACATGTTTGGCTCC | 54 |
| DP-3[c] | CCTCAATGCTGCTGCTGTACTAC | 53 |
| DP-4[a] | AGTCGGAAGTACTACTCTCT | 57 |

+ = LNA-modified base, underline = target complementary sequence, italic = detection probe complementary sequence
Oligonucleotides were purchased from Integrated DNA Technologies[a], Exiqon[b], Biomers[c] and Eurogentec[d].

TABLE 5

Summary of samples that were genotyped for KRAS mutations

Mutation analysis of fresh frozen, FFPE and tumor imprint samples

| Sample ID | Sample Type | Target | 1. Pyrosequencing | | 2. In situ padlock probe mutation detection | |
|---|---|---|---|---|---|---|
| | | | Mutants/Total | Mutations | Mutants/Total | Concordance |
| 1-5 | Fresh frozen colon | KRAS | 4/5 | 1xG12D, 1xG12C, 1xG13D, 1xG12A | 4/5 | 100% |
| 6-10 | Fresh frozen lung | KRAS | 4/5 | 1xG12D, 1xG12V, 1xG12C, 1xG12S | 4/5 | 100% |

TABLE 5-continued

Summary of samples that were genotyped for KRAS mutations

| | | | | | | |
|---|---|---|---|---|---|---|
| 11-24 | FFPE colon | KRAS | 14/14 | 2xG12D, 3xG12V, 2xG12C, 3xG13D, 2xG12S, 1xG12A | 14/14 | 100% |
| 25-26 | FFPE lung | KRAS | 2/2 | 2xQ61H | 2/2 | 100% |
| 27-35 | FFPE lung | EGFR | 8/9 | 8xL858R | 8/9 | 100% |
| 36 | FFPE lung | EGFR | 1/1 | 1xG719C, 1xS768I | 1/1 | 100% |
| 37 | FFPE lung | EGFR/TP53 | 1/1 | 1xG719A, 1xS127F | 1/1 | 100% |
| 38 | FFPE lung | KRAS/TP53 | 1/1 | 1xG12C, 1xP190S | 1/1 | 100% |

Mutation analysis of prospective FFPE and tumor imprint samples

| Sample ID | Sample Type | Target | 1. In situ padlock probe mutation detection Mutants/Total | 2. Pyrosequencing Mutants/Total | Mutations | Concordance |
|---|---|---|---|---|---|---|
| 39-46 | FFPE lung | KRAS | 3/8 | 3/8 | 2xG12C, 1xG12R | 100% |
| 47-54 | Colon tumor imprint | KRAS | 2/8 | 2/8 | 1xG12D, 1xG12R | 100% |
| 55-79 | FFPE colon (from TMA) | KRAS | 11/25 | 11/25 | 6xG12V, 2xG12S, 2xG13D, 1xG12A | 100% |

TABLE 6

Oligonucleotides on samples

| Sample ID | Primers | | Padlock probes | | | | Detection probes | | | |
|---|---|---|---|---|---|---|---|---|---|---|
| 1 | P-KRAS-c12/13 | P-ACTB | PP-KRAS-wt2 | PP-KRAS-G12D | PP-ACTB | | DP-1 | DP-2 | DP-3 | |
| 2 | P-KRAS-c12/13 | P-ACTB | PP-KRAS-wt1 | PP-KRAS-G12C | PP-ACTB | | DP-1 | DP-2 | DP-3 | |
| 3 | P-KRAS-c12/13 | P-ACTB | PP-KRAS-wt3 | PP-KRAS-G13D | PP-ACTB | | DP-1 | DP-2 | DP-3 | |
| 4 | P-KRAS-c12/13 | P-ACTB | PP-KRAS-wt2 | PP-KRAS-G12A | PP-ACTB | | DP-1 | DP-2 | DP-3 | |
| 5 | P-KRAS-c12/13 | P-ACTB | PP-KRAS-wt2 | PP-KRAS-G12A | PP-ACTB | | DP-1 | DP-2 | DP-3 | |
| 6 | P-KRAS-c12/13 | P-ACTB | PP-KRAS-wt2 | PP-KRAS-G12D | PP-ACTB | | DP-1 | DP-2 | DP-3 | |
| 7 | P-KRAS-c12/13 | P-ACTB | PP-KRAS-wt2 | PP-KRAS-G12V | PP-ACTB | | DP-1 | DP-2 | DP-3 | |
| 8 | P-KRAS-c12/13 | P-ACTB | PP-KRAS-wt1 | PP-KRAS-G12C | PP-ACTB | | DP-1 | DP-2 | DP-3 | |
| 9 | P-KRAS-c12/13 | P-ACTB | PP-KRAS-wt1 | PP-KRAS-G12S | PP-ACTB | | DP-1 | DP-2 | DP-3 | |
| 10 | P-KRAS-c12/13 | P-ACTB | PP-KRAS-wt2 | PP-KRAS-G12A | PP-ACTB | | DP-1 | DP-2 | DP-3 | |
| 11-12 | P-KRAS-c12/13 | P-ACTB | PP-KRAS-wt2 | PP-KRAS-G12D | PP-ACTB | | DP-1 | DP-2 | DP-3 | |
| 13-15 | P-KRAS-c12/13 | P-ACTB | PP-KRAS-wt2 | PP-KRAS-G12V | PP-ACTB | | DP-1 | DP-2 | DP-3 | |
| 16-17 | P-KRAS-c12/13 | P-ACTB | PP-KRAS-wt1 | PP-KRAS-G12C | PP-ACTB | | DP-1 | DP-2 | DP-3 | |
| 18-20 | P-KRAS-c12/13 | P-ACTB | PP-KRAS-wt3 | PP-KRAS-G13D | PP-ACTB | | DP-1 | DP-2 | DP-3 | |
| 21-22 | P-KRAS-c12/13 | P-ACTB | PP-KRAS-wt1 | PP-KRAS-G12S | PP-ACTB | | DP-1 | DP-2 | DP-3 | |
| 23-24 | P-KRAS-c12/13 | P-ACTB | PP-KRAS-wt2 | PP-KRAS-G12A | PP-ACTB | | DP-1 | DP-2 | DP-3 | |
| 25-26 | P-KRAS-Q61H | P-ACTB | PP-KRAS-wt4 | PP-KRAS-Q61H | PP-ACTB | | DP-1 | DP-2 | DP-3 | |
| 27-35 | P-EGFR-L858R | P-ACTB | PP-EGFR-wt1 | PP-EGFR-L858R | PP-ACTB-II | | DP-1 | DP-3 | DP-2 | |
| 36 | P-EGFR-S768I | P-EGFR-G719C/A | PP-EGFR-wt2 | PP-EGFR-S768I | PP-EGFR-wt3 | PP-EGFR-G719C | DP-1 | DP-3 | DP-2 | |
| 37 | P-EGFR-G719C/A | P-TP53-S127F | PP-EGFR-wt4 | PP-EGFR-G719A | PP-TP53-wt1 | PP-TP53-S127F | DP-1 | DP-2 | DP-3 | DP-4 |
| 38 | P-KRAS-c12/13 | P-TP53-P190S | PP-KRAS-wt1 | PP-KRAS-G12C | PP-TP53-wt2 | PP-TP53-P190S | DP-1 | DP-2 | DP-3 | DP-4 |
| 39-79 | P-KRAS-c12/13 | P-ACTB | PP-KRAS-wt1 PP-KRAS-wt2 | PP-KRAS-G12S PP-KRAS-G12D | PP-KRAS-G12R PP-KRAS-G12V | PP-KRAS-G12C PP-KRAS-G12A | DP-1 | DP-2 | DP-3 | |

TABLE 6-continued

Oligonucleotides on samples

| Cell lines | Primers | | Padlock probes | | | Detection probes | | |
|---|---|---|---|---|---|---|---|---|
| | | | PP-KRAS-wt3 | PP-KRAS-G13D | PP-ACTB | | | |
| ONCO-DG-1 | P-KRAS-c12/13-II | P-ACTB-II | PP-KRAS-wt2 | PP-KRAS-G12A | PP-ACTB | DP-1 | DP-2 | DP-3 |
| A427 | P-KRAS-c12/13-II | P-ACTB-II | PP-KRAS-wt2 | PP-KRAS-G12D | PP-ACTB | DP-1 | DP-2 | DP-3 |
| SW480 | P-KRAS-c12/13-II | P-ACTB-II | PP-KRAS-wt2 | PP-KRAS-G12V | PP-ACTB | DP-1 | DP-2 | DP-3 |
| HCT-15 | P-KRAS-c12/13-II | P-ACTB-II | PP-KRAS-wt3 | PP-KRAS-G13D | PP-ACTB | DP-1 | DP-2 | DP-3 |
| A549 | P-KRAS-c12/13-II | P-ACTB-II | PP-KRAS-wt1 | PP-KRAS-G12S | PP-ACTB | DP-1 | DP-2 | DP-3 |
| HUPT3 | P-KRAS-c12/13-II | P-ACTB-II | PP-KRAS-wt1 | PP-KRAS-G12R | PP-ACTB | DP-1 | DP-2 | DP-3 |

TABLE 7

EGFR mutations and prevalence based on cases in the COSMIC database.

| # | Mutation | Prevalence | |
|---|---|---|---|
| 1 | L858R | 1258 | 45.48084% |
| 2 | 2335_2349del15 | 560 | 20.24584% |
| 3 | 2336_2350del15 | 314 | 11.35213% |
| 4 | 2340_2357del18 | 110 | 3.97686% |
| 5 | T790M | 104 | 3.75994% |
| 6 | 2339_2348TTAAGAGAAG > C | 71 | 2.56688% |
| 7 | 2337_2355 > T | 43 | 1.55459% |
| 8 | 2340_2354del15 | 41 | 1.48228% |
| 9 | L861Q | 34 | 1.22921% |
| 10 | 2339_2356del18 | 28 | 1.01229% |
| 11 | G719S | 24 | 0.86768% |
| 12 | G719A | 23 | 0.83153% |
| 13 | S768I | 22 | 0.79537% |
| 14 | 2339_2351 > C | 19 | 0.68691% |
| 15 | 2337_2351del15 | 18 | 0.65076% |
| 16 | 2339_2347del9 | 18 | 0.65076% |
| 17 | 2339_2353del15 | 18 | 0.65076% |
| 18 | G719C | 16 | 0.57845% |
| 19 | 2307_2308ins9 | 8 | 0.28923% |
| 20 | 2339_2358 > CA | 7 | 0.25307% |
| 21 | 2340_2351del12 | 7 | 0.25307% |
| 22 | 2310_2311insGGT | 4 | 0.14461% |
| 23 | 2337_2354del18 | 4 | 0.14461% |
| 24 | 2338_2355del18 | 4 | 0.14461% |
| 25 | 2338_2348 > GC | 4 | 0.14461% |
| 26 | 2319_2320insCAC | 2 | 0.07231% |
| 27 | 2335_2352 > AAT | 2 | 0.07231% |
| 28 | 2338_2352 > GCA | 2 | 0.07231% |
| 29 | 2336_2353del18 | 1 | 0.03615% |

J. Examples

The invention will now be further described with reference to the following non-limiting Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All documents referenced herein are incorporated by reference.

Materials and Methods

Cell Culture:

The cell lines GM08402 (Coriell Cell Repositories) and BJhTERT were cultured in MEM without phenol red and l-glutamine (Gibco) supplemented with 10% FBS (Sigma), 1× nonessential amino acids (Gibco), 2 mM l-glutamine (Sigma) and 1× penicillin-streptomycin (PEST, Sigma). Mouse embryonic fibroblasts (MEF) were cultured in DMEM without phenol red and l-glutamine (Gibco) supplemented with 10% FBS, 2 mM l-glutamine and 1×PEST. ONCO-DG-1, SW-480, A-427 and HCT-15 (all four from DSMZ), SKOV3 and SKBR3 were cultured in RPMI culture medium (Sigma) supplemented with 10% FBS, 2 mM l-glutamine and 1×PEST. A-549 (DSMZ) was cultured in DMEM without phenol red and L-Glutamine (Gibco) supplemented with 10% FBS, 2 mM L-Glutamine and 1×PEST. HUP-T3 (DSMZ) was cultured in MEM-Eagle culture medium (Sigma) supplemented with 10% FBS, 2 mM L-glutamine and 1×PEST.

Preparation of Tissue Sections:

Fresh frozen 9-μm sections of E14.5 mouse embryos were placed on Superfrost Plus Gold slides (Thermo Scientific). Fully anonymized fresh frozen human tissue sections from a HER2-positive breast cancer were obtained from the Fresh Tissue Biobank at the Department of Pathology, Uppsala University Hospital, in accordance with the Swedish Biobank Legislation. Breast tissue sections of 4 μm thickness were placed on Starfrost microscope slides (Instrumedics).

Sample Pretreatment for In Situ Experiments:

Cells were seeded on Superfrost Plus slides (Thermo Scientific) and allowed to attach. When the cells reached the desired confluency they were fixed in 3% (w/v) paraformaldehyde (Sigma) in PBS for 30 min at room temperature (20-23° C.). After fixation, slides were washed twice in DEPC-treated PBS (DEPC-PBS) and dehydrated through a series of 70%, 85% and 99.5% ethanol for 3 min each. The molecular reactions were performed in Secure-seals (Grace Bio-Labs, 9 mm in diameter and 0.8 mm deep) attached to the slides. A 50-μl reaction volume was used for each sample. To make the RNA more readily available for cDNA synthesis, 0.1 M HCl was applied to the cells for 10 min at room temperature. This was followed by two brief washes in DEPC-PBS. Tissues were treated similarly to cell lines, with a few exceptions. Tissue fixation was performed in 2% (w/v) paraformaldehyde in PBS. The tissue was then permeabilized with 0.01% pepsin (Sigma) in 0.1 M HCl at 37° C. for 2 mM. Molecular reactions were carried out with a reaction volume of 100 μl in Secure-seals (13 mm in diameter, 0.8 mm deep; Grace Bio-Labs) mounted over the tissue. Reverse transcription was carried out overnight and incubation times for ligation, RCA and detection probe hybridization were doubled. For the mouse tissue, ligation was carried out with T4 DNA ligase.

Oligonucleotide Sequences:

Oligonucleotide sequences (Tables 1-3) were designed using GenBank accession numbers NM_001101.3 (ACTB), NM_007393.3 (Actb), NM_198253.2 (TERT), NM_002467 (MYC), NM_001005862.1 (ERBB2), NM_009606 (Acta1), NM_009609 (Actg1) and NM_033360 (KRAS). All padlock probes were 5'-phosphorylated at a concentration of 2 μM with 0.2 μl$^{-1}$ T4 polynucleotide kinase (Fermentas) in the manufacturer's buffer A plus 1 mM ATP for 30 min at 37° C., followed by 10 min at 65° C. For β-actin transcript detection in cultured cells, primer P-βe1 was used for detection with padlock probe PLP-βe1, primer P-βe6 with padlock probe PLP-βe6, primer P-βhum with padlock probe PLP-βhum and primer P-βmus with padlock probe PLP-βmus unless otherwise indicated. TERT was detected with primer P-TERT and padlock probe PLP-TERT, cMyc with primer P-cMyc and padlock probe PLP-cMyc and HER2 with primer P-HER2 and padlock probe PLP-HER2. For detection of transcripts in mouse tissue, primer P-βmus was used with padlock probe PLP-βmus for β-actin, primer P-α1mus with padlock probe PLP-α1mus for α1-actin and primer P-γ1 mus with padlock probe PLP-γ1mus for γ1-actin. For KRAS genotyping, primer P-KRAS was used in combination with the padlock probes PLP-KRAS-wtGGT, PLP-KRAS-mutGTT and PLP-KRAS-mutGAT.

Sample Preparation for KRAS Genotyping Experiments:

Cell lines ONCO-DG-1, A-427, SW-480, HCT-15, A-549 and HUP-T3 (all DSMZ) were seeded on Collagen 18-well CultureSlides (BD BioCoat), and allowed to attach. When the cells reached the desired confluency they were fixed in 3% (w/v) paraformaldehyde (Sigma) in DEPC-treated PBS (DEPC-PBS) for 30 min at room temperature (20-23° C.). After fixation slides were washed twice in DEPC-PBS and the plastic wells were removed from the slides. The slides were thereafter dehydrated through an ethanol series of 70%, 85% and 99.5% ethanol for 1 min each.

Fresh frozen and FFPE human tumor tissues from colorectal- and lung cancer patients were obtained from the Biobank at the Department of Pathology and Cytology (Botling and Micke, 2011), Uppsala University Hospital, in accordance with the Swedish Biobank Legislation and Ethical Review Act (Uppsala Ethical Review Board approval, reference numbers 2006/325 and 2009/224).

Tape transferred fresh frozen tissue sections (4 μm) on Starfrost microscope slides (Instrumedics) were prepared from fresh frozen tumor samples stored at −80° C. The slides were fixed in 3% (w/v) paraformaldehyde in DEPC-PBS for 45 min at room temperature and then permeabilized with 0.01% pepsin (Sigma, #P0609) in 0.1 M HCl at 37° C. for 2 min followed by a brief wash in DEPC-PBS.

Touch imprints, prepared on Superfrost Plus microscope slides, were obtained from fresh surgical colorectal and lung cancer specimens. After slide preparation the slides were air-dried for 1 min and thereafter stored at −80° C. The slides were fixed in 3% (w/v) paraformaldehyde in DEPC-PBS for 30 min at room temperature followed by a brief wash in DEPC-PBS.

FFPE tissue sections (4 μm) were placed on Superfrost Plus microscope slides (Menzel Glaser and baked for 30 min at 60° C. The slides were then deparaffinized by immersion in xylene for 15+10 min and thereafter gradually rehydrated through an ethanol series (2×2 min in 100%, 2×2 min in 95%, 2×2 min in 70%, and finally for 5 min in DEPC-H$_2$O). The slides were washed in DEPC-PBS for 2 min before fixation with 4% (w/v) paraformaldehyde in DEPC-PBS for 10 min at room temperature which was followed by another DEPC-PBS wash for 2 min. The FFPE tissue slides were then permeabilized in 2 mg ml-1 Pepsin (Sigma #P7012) in 0.1 M HCl at 37° C. for 10 min. The digestion was stopped by a wash in DEPC-treated H$_2$O (DEPC-H$_2$O) for 5 min followed by a wash in DEPC-PBS for 2 min. Finally, the slides were fixed a second time with 4% (w/v) paraformaldehyde in DEPC-PBS for 10 min at room temperature and washed in DEPC-PBS for 2 min. After completed pretreatments of tissues, the slides were dehydrated through an ethanol series of 70%, 85% and 99.5% ethanol for 1 min each.

The KRAS mutation status of the tissues was analyzed by Pyrosequencing (Pyromark Q24 KRAS, Qiagen GmbH, Hilden, Germany) as described previously (Sundstrom et al., 2010).

Figure 5:
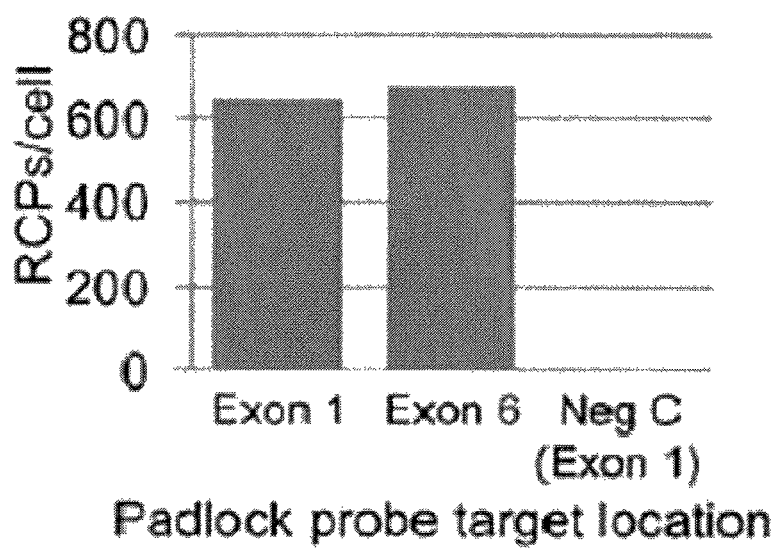
FIG. 5: Detection of individual β-actin transcripts in cultured human fibroblasts. Target sites in exons 1 and 6 on the β-actin transcript were probed in GM08402 cells. A negative control was performed without addition of reverse transcriptase.

In Situ cDNA Detection Procedure:

Samples were preincubated in M-MuLV reaction buffer. Then 1 μM of cDNA primer was added to the slides with 20 U μl$^{-1}$ of RevertAid H minus M-MuLV reverse transcriptase (Fermentas), 500 nM dNTPs (Fermentas), 0.2 μg μl$^{-1}$ BSA (NEB) and 1 U μl$^{-1}$ RiboLock RNase Inhibitor (Fermentas) in the M-MuLV reaction buffer. Slides were incubated for 3 h to overnight at 37° C. After incubation, slides were washed briefly in PBS-T (DEPC-PBS with 0.05% Tween-20 (Sigma)), followed by a postfixation step in 3% (w/v) paraformaldehyde in DEPC-PBS for 30 min at room temperature. After postfixation, the samples were washed twice in PBS-T. To make the target cDNA strands available for padlock probe hybridization, the RNA portion of the created RNA-DNA hybrids was degraded with ribonuclease H. This was performed in the same step as the padlock probe hybridization and ligation. For most reactions, Ampligase (Epicentre) was used for ligation. Samples were first preincubated in Ampligase buffer (20 mM Tris-HCl, pH 8.3, 25 mM KCl, 10 mM MgCl$_2$, 0.5 mM NAD and 0.01% Triton X-100). Ligation was then carried out with 100 nM of each padlock probe in a mix of 0.5 U μl$^{-1}$ Ampligase, 0.4 U μl$^{-1}$ RNase H (Fermentas), 1 U μl$^{-1}$ RiboLock RNase Inhibitor, Ampligase buffer, 50 mM KCl and 20% formamide. Incubation was performed first at 37° C. for 30 min, followed by 45 min at 45° C. For detection of actin transcript isoforms in mouse embryonic tissue sections, ligation was instead carried out using T4 DNA ligase (Fermentas). Samples were then first preincubated in T4 DNA ligase buffer (Fermentas). Then 100 nM of each padlock probe was added with 0.1 U μl$^{-1}$ T4 DNA ligase, 0.4 U μ$^{-1}$ RNase H, 1 U μl$^{-1}$ RiboLock RNase Inhibitor and 0.2 μg μl$^{-1}$ BSA in T4 DNA ligase buffer supplemented with 0.5 mM ATP and 250 mM NaCl. Slides were then incubated at 37° C. for 30 min. After ligation with Ampligase or T4 DNA ligase, slides were washed in DEPC-treated 2×SSC with 0.05% Tween-20 at 37° C. for 5 min and rinsed in PBS-T. Slides were preincubated briefly in Φ29 DNA polymerase buffer (Fermentas). RCA was then performed with 1 U μl$^{-1}$ Φ29 DNA polymerase (Fermentas) in the supplied reaction buffer, 1 U μl$^{-1}$ RiboLock RNase Inhibitor, 250 μM dNTPs, 0.2 μg μl$^{-1}$ BSA and 5% glycerol. Incubation was carried out for 60 min at 37° C. The incubation was followed by a wash in PBS-T. RCPs were visualized using 100 nM of each corresponding detection probe in 2×SSC and 20% formamide at 37° C. for 30 min. Slides were then washed in PBS-T, the Secure-seals were removed and the slides were dehydrated using a series of 70%, 85% and 99.5% ethanol for 3 min each. The dry slides were mounted with Vectashield (Vector), containing 100 ng ml$^{-1}$ DAPI to counterstain the cell nuclei. The protocol for counterstaining of cell membranes in FIG. 5 is described under "WGA Staining" below.

WGA Staining:

For counterstaining of cytoplasms 2.5 µg ml$^{-1}$ WGA 488 (Invitrogen) diluted in 1×PBS was added for 60 min at room temperature. This was followed by two washes in PBS-T and dehydration before mounting and nuclear staining with DAPI as described before.

Figures 6A, 6B:
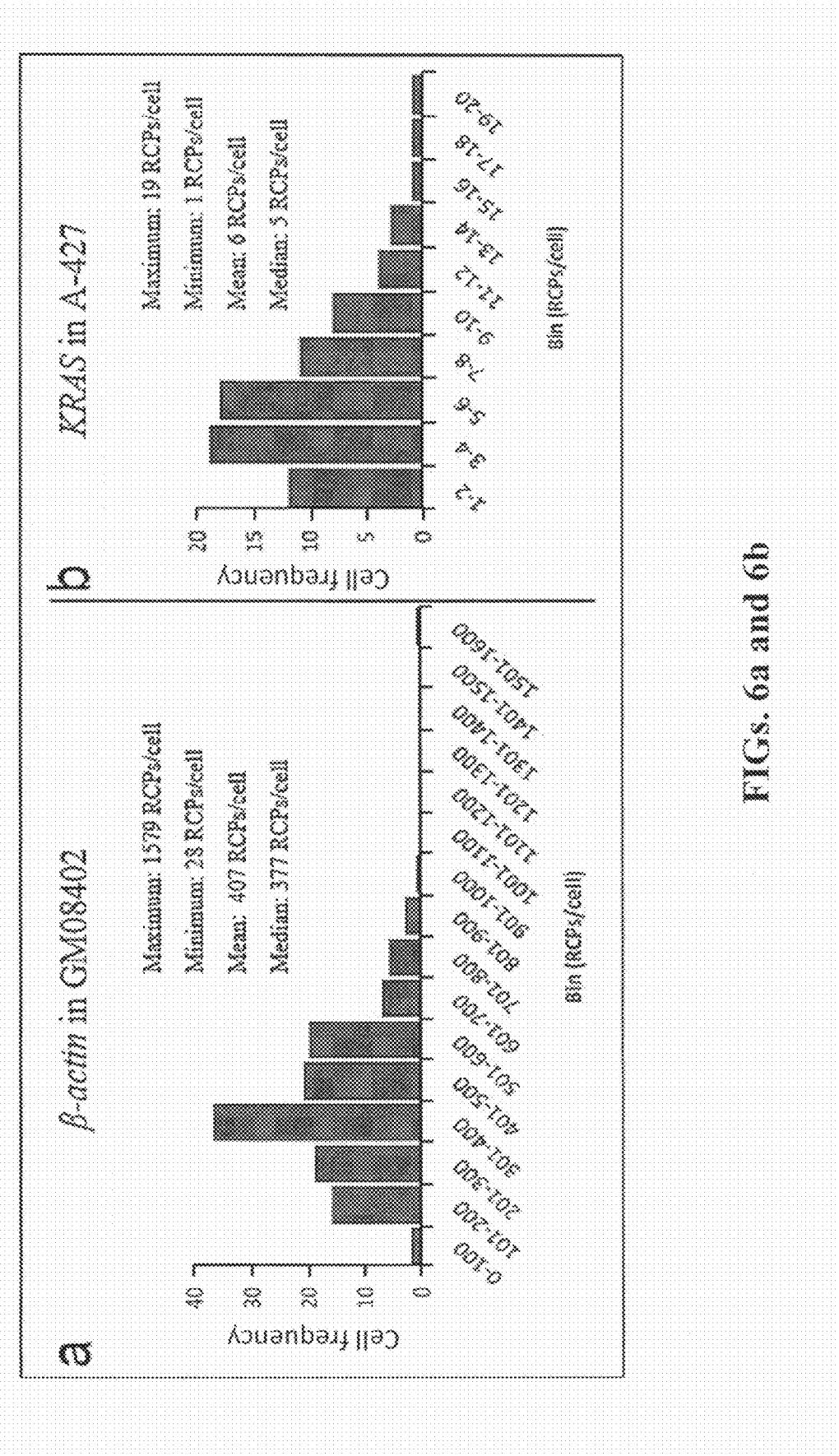
FIG. 6: Quantification of RCPs in single cultured cells. Histogram showing quantification of (a) β-actin RCPs in 134 cells of a GM08402 culture and (b) KRAS RCPs in 77 cells of an A-427 culture.

Single-Cell Quantification:

For single-cell quantification in FIG. 6, a custom made MatLab script was used for marking individual cells and counting RCPs within the marked areas. The quantification of RCPs in MatLab differs in how an RCP is defined compared to the BlobFinder software used for quantification in other Examples herein. As a consequence the results show ~30% fewer RCPs compared to the BlobFinder analysis.

Image Acquisition and Analysis:

Images of cultured cells were acquired using an Axioplan II epifluorescence microscope (Zeiss) equipped with a 100 W mercury lamp, a CCD camera (C4742-95, Hamamatsu), and a computer-controlled filter wheel with excitation and emission filters for visualization of DAPI, FITC, Cy3, Cy3.5 and Cy5. A ×20 (Plan-Apocromat, Zeiss), ×40 (Plan-Neofluar, Zeiss) or ×63 (Plan-Neofluar, Zeiss) objective was used for capturing the images. Images were collected using the Axiovision software (release 4.3, Zeiss). Exposure times for cell images were 260-340 ms (at ×20 magnification), 10-80 ms (×40) or 220 ms (×63) for DAPI; 40 ms (×40) or 220 ms (×63) for FITC; 560-640 ms (×20), 110-160 ms (×40) or 200 ms (×63) for Cy3; 110 ms (×40) or 250 ms (×63) for Texas Red; and 6,350 ms (×20), 180 ms (×40) or 350 ms (×63) for Cy5. For SKBR3 and SKOV3 cells, images were collected as z-stacks to ensure that all RCPs were imaged. The imaging of α1-actin and β-actin in fresh frozen mouse embryonic tissue sections in Example 3 was imaged using a Mirax Midi slide scanner (3D Histech) equipped with a CCD camera (Axio-Cam MRm, Zeiss) and a ×20 Plan-Apochromat objective. Exposure times in the slide scanner were 45 ms for DAPI, 270 ms for Cy3, 340 ms for Texas Red and 3,200 ms for Cy5. For quantification, the numbers of RCPs and cell nuclei in images were counted digitally using BlobFinder software (version 3.0_beta). For cultured cells, the quantification was done on five 20× microscope images (approximately 20-30 cells for each sample). The total number of RCPs was divided by the number of nuclei for each image. The average for each sample was then calculated from the result of the five images and is reported as RCPs per cell. The procedure for single-cell quantification used in FIG. 6 is described "Single cell quantification" above.

qPCR for β-Actin Transcript Quantification in Cells:

Two separate passages of the cell line GM08402 were collected after counting of cells, and total RNA was purified from the cells using the PARIS kit (Ambion) with the protocol for RNA isolation from total cell lysate. Traces of DNA were removed from the purified RNA using the DNA-free kit (Ambion). First-strand cDNA synthesis was carried out with 700 ng of template RNA in a mix containing 20 U RevertAid H minus M-MuLV reverse transcriptase (Fermentas) in the corresponding enzyme buffer, 0.5 µg oligo(dT) primer (20-mer), 1 mM dNTPs and 1 U µl$^{-1}$ RiboLock RNase Inhibitor. Samples were incubated at 37° C. for 5 min, followed by 42° C. for 60 min. The reaction was stopped by heating to 70° C. for 10 min. A preparative PCR was carried out to synthesize template for standard curve creation. For this PCR, 1 µl of cDNA from one of the cell passages was amplified in a mix of 0.02 U µl$^{-1}$ Platinum Taq DNA polymerase (Invitrogen), PCR buffer, 2 mM MgCl$_2$, 200 µM dNTPs, 200 nM ACTBfwd primer and 200 nM ACTBrev primer in a total volume of 50 PCR was carried out with 2 min at 95° C., followed by cycling 45 times (95° C. for 15 s, 50° C. for 15 s, and 72° C. for 1 min) and finishing with 72° C. for 5 min. The PCR product was purified using the Illustra GFX PCR and gel band purification kit (GE Healthcare) according to the protocol for purification of DNA from solution. The concentration of the purified PCR product was measured using a Nanodrop 1000 spectrophotometer (Thermo Scientific) and the number of molecules per microliter was calculated. qPCR was run with 2 µl of template cDNA, or diluted standard curve PCR product, with SYBR Green (Invitrogen), 0.02 U µl$^{-1}$ Platinum Taq DNA polymerase, PCR buffer, 2 mM MgCl$_2$, 200 µM dNTPs, 200 nM ACTBfwd primer and 200 nM ACTBrev primer in a total volume of 30 µl. The qPCR was run using the same program as for the preparative PCR. Standard curve samples were run in duplicates of the same sample and cDNA samples from the two passages of cells were run in triplicates. Calculations of transcript copy numbers for the two cell passages were based on the number of counted cells at harvest. The average β-actin mRNA copy number for the cell line was then determined. The protocol for efficiency estimation by qPCR for the in situ multiplex detection experiment is as follows:

The cell lines GM08402, SKBR3 and BJhTERT were harvested after counting of cells and total RNA was purified from the cells using the RiboPure kit (Ambion). DNA traces were removed from the purified RNA using the DNA-free kit (Ambion). RNA concentration and quality was investigated on an Agilent Bioanalyzer using a RNA 6000 Pico chip (Agilent). First strand cDNA synthesis was carried out using the High capacity cDNA reverse transcription kit (Applied Biosystems). The prepared cDNA was diluted 4× before analysis with TaqMan qPCR. PCR primers and TaqMan probes were purchased as validated 20× TaqMan Gene Expression Assays from Applied Biosystems (assay no Hs99999903_m1 for β-actin, Hs00972650_m1 for TERT, and Hs99999005_mH for HER2). Templates for standard curves for the different genes were created by PCR. For this PCR, 1 µl of cDNA from the BJhTERT cell line was amplified in a mix of 0.02 U µl$^{-1}$ Platinum Taq DNA polymerase (Invitrogen), 1×PCR buffer, 2 mM MgCl2, 200 µM dNTP, and 0.01× of each primer mix (0.2 µM of each primer) in separate reactions for the different genes. The total PCR volume was 50 µl and the PCR was carried out with 2 min at 95° C., followed by cycling 45×(95° C. for 15 s and 60° C. for 1 min), and finished with 60° C. for 5 min. The PCR products were purified using the Illustra GFX PCR and gel band purification kit (GE Healthcare). The concentration of the purified PCR products was measured using a Nanodrop 1000 spectrophotometer (Thermo Scientific) and the number of molecules per µl was calculated. The qPCR was run with 4 µl of template cDNA, or standard curve PCR product in 1× TaqMan Universal PCR Master Mix, No AmpErase UNG (Applied Biosystems) with 1× TaqMan Gene Expression Assay primer and probe mix in a total volume of 20 µl. The qPCR program was run with 10 min at 95° C., followed by cycling 40× with 95° C. for 15 s and 60° C. for 1 min. All samples were run in duplicates and featured serial dilutions of the standard curves, serial diluted cDNA samples, RNA controls from the cell lines, and no template controls. Calculations of transcript copy numbers were based on the number of counted cells at harvest.

In Situ Genotyping of KRAS on Cell Lines and Tissues:

All the molecular in situ reactions were carried out in Secure-seals (Grace Bio-Labs Inc.) and the reaction volumes for tissues or imprints were either 100 μl (size 13 mm diameter, 0.8 mm deep) or 350 μl (size 22 mm diameter, 0.8 mm deep) depending on the size of the sample. The Secure-seals that were used for cells had a total volume of 50 μl (size 9 mm diameter and 0.8 mm deep). The Secure-Seals were mounted over the cells or tissues and the wells were dehydrated by a brief flush with PBS-T (DEPC-PBS with 0.05% Tween-20 (Sigma)).

The samples were thereafter treated in the same way with just the following exceptions. Post-fixation of fresh frozen and FFPE tissues was performed for 45 min compared to 30 min for cell lines imprints. Also, the RCA time on tissues was longer (8 h) compared to cultured cells and tumor imprints (2 h). For all reactions slides were incubated in humid chambers.

Oligonucleotide Sequences for KRAS Genotyping Experiments:

Oligonucleotides sequences (Table 4) were designed using GenBank accession numbers NM_033360 (KRAS), NM_005228 (EGFR), NM_001126114.1 (TP53) and NM_001101.3 (ACTB). All padlock probes were 5' phosphorylated at a concentration of 10 μM with 0.2 U μl$^{-1}$ T4 PNK (Fermentas) in PNK buffer A and 1 mM ATP for 30 min at 37° C., followed by 10 min at 65° C. The primers, padlock probes and detection probes applied on the different tissue samples and cell lines are summarized in Table 6.

One μM of cDNA primer was added to the slides with 20 U μl$^{-1}$ of RevertAid H minus M-MuLV reverse transcriptase (Fermentas), 500 μM dNTP (Fermentas), 0.2 μg μl$^{-1}$ BSA (NEB), and 1 U μl$^{-1}$ RiboLock RNase Inhibitor (Fermentas) in the M-MuLV reaction buffer. Slides were incubated for 3 hours at 37° C.

After incubation slides were washed briefly by flushing the wells in PBS-T, followed by a post-fixation step in 3% paraformaldehyde (w/v) in DEPC-PBS for 45 (fresh frozen and FFPE tissues) or 30 (imprints) minutes at room temperature. After post-fixation the samples were washed by flushing the Secure-seals chambers with PBS-T.

RNase H Digestion, Padlock Probe Hybridization and Ligation for KRAS Genotyping Experiments:

To create single-stranded target cDNA available for padlock probe hybridization, the RNA part of the created RNA-DNA hybrids was degraded with RNase H. This was performed in the same step as hybridization and ligation of the padlock probes. The reaction was carried out with 100 nM of each padlock probe in a mix of 1 U μl$^{-1}$ Ampligase (Epicentre), 0.4 U μl$^{-1}$ RNase H (Fermentas), 1 U μl$^{-1}$ RiboLock RNase Inhibitor, 50 mM KCl, 20% formamide in Ampligase buffer. Incubation was performed first at 37° C. for 30 min, followed by 45 min at 45° C. After ligation, slides were washed flushing the chambers with PBS-T. For prospective KRAS mutation detection of unknown tissue samples a cocktail of all KRAS codon 12 and 13 padlock probes was mixed with a final concentration of 10 nM.

Amplification and Detection of Circularized Padlock Probes for KRAS Genotyping Experiments:

RCA was performed with 1 U μl$^{-1}$ Φ29 DNA polymerase (Fermentas) in the supplied reaction buffer with 1 U μl$^{-1}$ RiboLock RNase Inhibitor, 250 μM dNTP, 0.2 μg μl$^{-1}$ BSA, and 5% glycerol. Incubation was carried out for 2 h for tumor imprints as well as for cell lines and approximately 5 h for fresh frozen and FFPE tissues at 37° C. After RCA the samples were washed flushing the Secure-seals chambers with PBS-T. RCPs were visualized using 100 nM of each corresponding detection probe in 2×SSC and 20% formamide at 37° C. for 15 min. Slides were then washed again by flushing the chambers in PBS-T, the Secure-seals were removed and the slides were dehydrated using a series of 70%, 85%, and 99.5% ethanol for 30 sec each. The dry slides were mounted with Vectashield (Vector), containing 100 ng ml$^{-1}$ DAPI to counterstain the cell nuclei.

Image Acquisition and Analysis for KRAS Genotyping Experiments:

Images were acquired using an AxioplanII epifluorescence microscope (Zeiss), equipped with a 100 W mercury lamp, a CCD camera (C4742-95, Hamamatsu), and a computer-controlled filter wheel with excitation and emission filters for visualization of DAPI, FITC, Cy3 and Cy5. For capturing the images, a ×10 (Plan-Apocromat, Zeiss) objective was used for fresh frozen and FFPE tissues, a ×20 (Plan-Apocromat, Zeiss) objective for tumor imprints and finally a ×63 (Plan-neofluar, Zeiss) objective was used for the cells. Images were collected using the Axiovision software (Release 4.8, Zeiss). Images displayed for illustrations were processed using image editing software for clarity in print. The threshold for different color channels was set using ImageJ 1.42q and for clearer visualization of the KRAS signals in Cy3 and Cy5, a maximum filter was applied.

Example 1

Detection of β-Actin (ACTB) Transcripts in Cultured Human Cells Using Padlock Probes To detect β-actin (ACTB) transcripts in cultured human cells, two different padlock probes were used targeting sequences in the first and last exon, respectively. Many bright, spot-like signals localized to the cytoplasm of cells were visualized, consistent with previous observations of this transcript consistent with previous reports regarding this transcript. The detection efficiency was similar for the two padlock probes, indicating that in this case detection was not highly dependent on target position along the transcript (FIG. 5). In contrast, when reverse transcriptase was omitted from the cDNA synthesis reaction, no signals were detected, verifying that the signals were cDNA dependent (FIG. 5). It was estimated that the overall in situ detection efficiency to be ~30% of available transcripts, on the basis of a comparison to quantitative PCR (qPCR) data for β-actin mRNA in the GM08402 cell line (2,000 copies per cell). There was considerable variation in the number of signals among cells (FIG. 6), consistent with other reports of intercellular variation in β-actin mRNA expression.

Example 2

Detection of Single-Nucleotide Variants of Transcripts in Cultured Cells In Situ To demonstrate high selectivity of detection, an assay was used to detect of single-nucleotide variants of transcripts in situ. Expressed polymorphisms are rare in β-actin, therefore a single-base difference between the human and mouse β-actin sequences was used as genotyping target. Co-cultured human and mouse fibroblast cells were subjected to in situ genotyping of cDNA using padlock probes PLP-βhum (human) and PLP-βmus (*Mus musculus*) and target-primed RCA. There was a clear-cut distinction observed between the two subpopulations of cells in the co-culture. The preference for perfectly matched padlock probes at the circularization step ensures distinction between the two targets by the ligase.

Example 3

Detection of Single-Nucleotide Variants of Transcripts in Fresh Frozen Tissue In Situ To test the method in fixed tissue sections, closely related skeletal muscle α1-actin (Acta1) and cytoplasmic β-actin (Actb) transcripts were targeted in fresh frozen tissue from an E14.5 mouse embryo cross sectioned at the level of the neck. The two actin transcripts were successfully detected in the tissue using padlock probes designed with target sequences differing by a single base. The α1-actin signals were mainly distributed to skeletal muscles, whereas β-actin signals were widely distributed but showed slightly more signals in the non-muscular tissue. The ability to distinguish three transcripts from the same gene family was demonstrated by including a probe specific for the cytoplasmic α1-actin (Acta1) transcript.

Example 4

Detection of Transcripts for Expression Profiling

To test the method's ability for multiplex detection of transcripts for expression profiling, padlock probes were designed for the three cancer-related transcripts HER2 (also known as ERBB2), cMyc (also known as MYC) and TERT. Using β-actin as a reference transcript, these transcripts were assayed in four cell lines (a human ovarian carcinoma cell line, a human breast carcinoma cell line, a TERT-immortalized human foreskin fibroblast cell line and a primary fibroblast cell culture). The levels of expression of the cancer-related genes differed among the cell lines (FIG. 2a-d). The ovarian and breast carcinoma cell lines showed similar patterns of expression of the HER2 and cMyc transcripts, whereas the TERT-immortalized fibroblast was the only cell type with a detectable level of the TERT transcript. All four cell lines expressed β-actin, and in the normal fibroblasts this was the only investigated transcript expressed at a detectable level. These results were compared to qPCR data and to available literature and good correlation with the expected relative expression levels in the different cell lines and a notable consistency in detection efficiency among the different transcripts was found (Example 5). Large cell-to-cell variation in expression for all investigated transcripts was noticed, which is consistent with previous studies of expression in single cells in cultures.

Example 5

Expression of Cancer-Related Transcripts in Human Cell Lines

The three cancer-related transcripts TERT, HER2, and cMyc were assayed in four cell lines as described in Example 4. All cell lines expressed the housekeeping gene β-actin, but differed in the expression of the cancer-related transcripts according to the in situ data. qPCR measurements were then performed to quantify the different transcripts in the GM08402, BJhTERT and SKBR3 cell lines to be able to evaluate the variation in detection efficiency in the in situ experiments. qPCR measurements of TERT expression showed relatively high expression in the BJhTERT cell line (247 molecules/cell), as well as low expression in the SKBR3 breast carcinoma cell line (6 molecules/cell). No TERT expression was detected in the normal primary fibroblasts by qPCR. The qPCR data for TERT correlates well with the mRNA expression level for TERT found in the literature (220 molecules/cell for BJhTERT and 0.57 molecules/cell for SKBR3 (Yi et al., 2001). The in situ result of 39 RCPs detected per cell in BJhTERT thus corresponds to a detection efficiency of 16% based on the qPCR data. The HER2 transcript is known to be overexpressed in the ovarian and breast carcinoma cell lines. In the SKBR3 cell line the number of HER2 mRNAs/cell is reported to be 168-336 molecules, the qPCR measurement described herein ended at 177 molecules/cell. The number of HER2 mRNAs/cell detected in situ was 25. This gives a detection efficiency of 14% for the HER2-transcript in SKBR3 cells. HER2 expression could not be detected by qPCR in the normal primary fibroblasts or in the BJhTERT cell line. The expression level of cMyc in SKOV3 cells is estimated to about one quarter of the number of HER2 transcripts in the same cell line, which correlates well with the in situ measurement described herein. When assayed alone, the detection efficiency for β-actin in cultured fibroblast cells was estimated to be 30% based on qPCR measurements and in situ detection of the transcript. In these multiplex experiments the detection efficiency is slightly lower, about 15%, based on the same qPCR estimation. A similar effect is observed among the cancer transcripts that show detection efficiencies of about 15% in multiplex, while they perform better individually. It is likely that the lower detection efficiency observed for targets in multiplex experiments are due to interactions between different padlock probes and/or cDNA primers, especially since the LNA modified bases of the cDNA primers have the capacity to bind very strongly to each other. The detection protocol for multiplex reactions can be improved by optimizing the concentration of the probes and/or primers. Further qPCR measurements show good correlation with the in situ measurements for the relative β-actin expression level between the cell lines. Taken together these data indicate that the relative levels of RCPs in the different cell types are good estimates of the true relative transcript levels in the cell populations. Thus it is believed that the method is suitable for relative expression profiling in different samples. Although as the reverse transcription reaction is known to introduce variation in mRNA quantification by qPCR, this is likely to be the case also for reverse transcription in situ.

Example 6

Detection of Transcript Distribution in a Fresh Frozen HER2-Positive Human Breast Cancer Tissue The technique of this invention was also used to assess HER2 transcript distribution in a fresh frozen HER2-positive human breast cancer tissue section. Expression varied widely among the cells, consistent with the expected presence of cancer cells and normal stroma in the tumor tissue.

Example 7

Genotyping of a KRAS Point Mutation in KRAS Wild-Type and Mutant Cells

Figure 7:
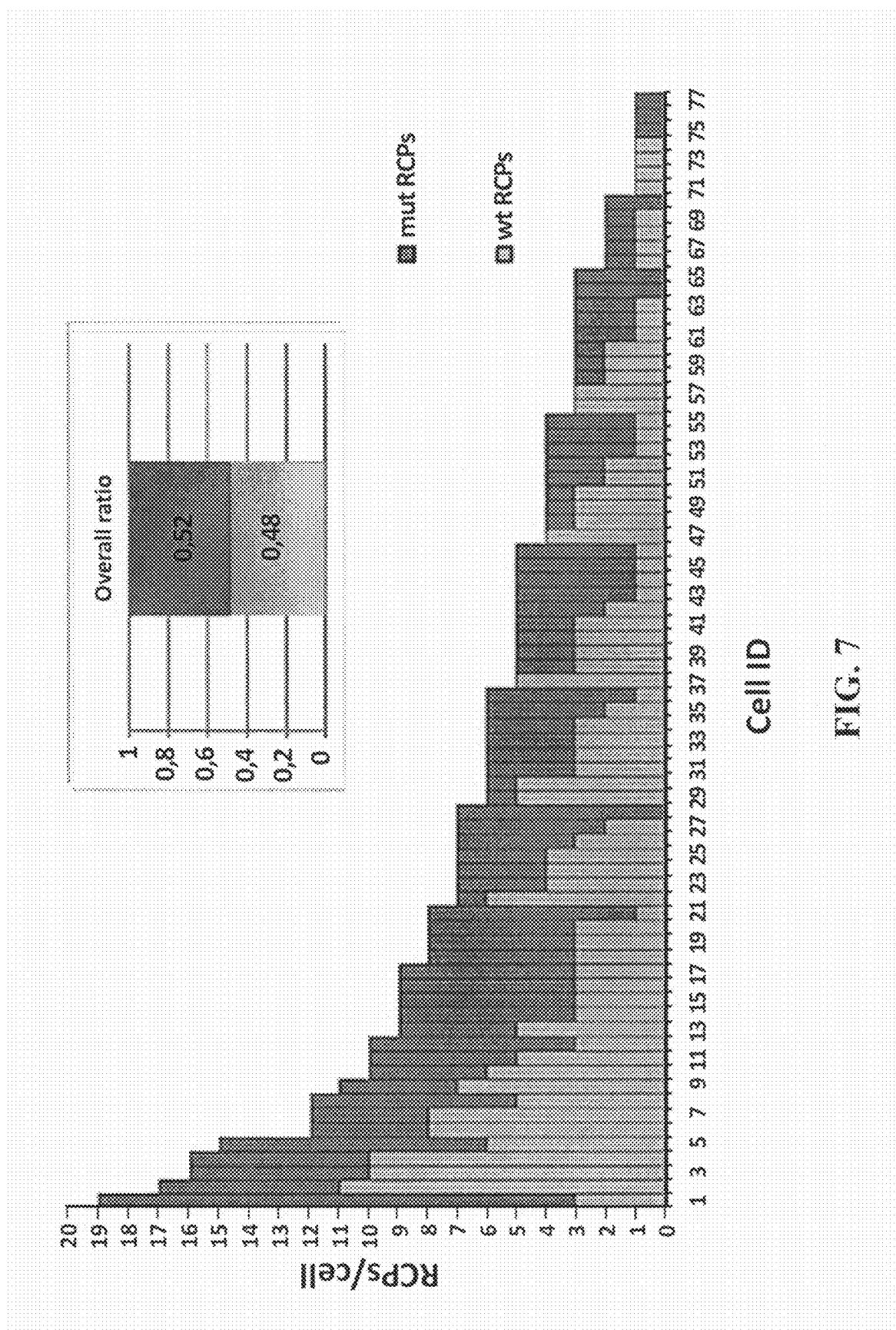
FIG. 7: In situ genotyping of KRAS codon 12 mutations in cell lines with padlock probes and RCA. Quantification of the number of RCPs/cell detected in situ in the heterozygous cell line A-427, showing the allelic expression of wild type (light grey) and mutated (dark grey) KRAS-RCPs in single cells. Inset represents the overall allelic ratio from 77 counted cells.
Figure 8:
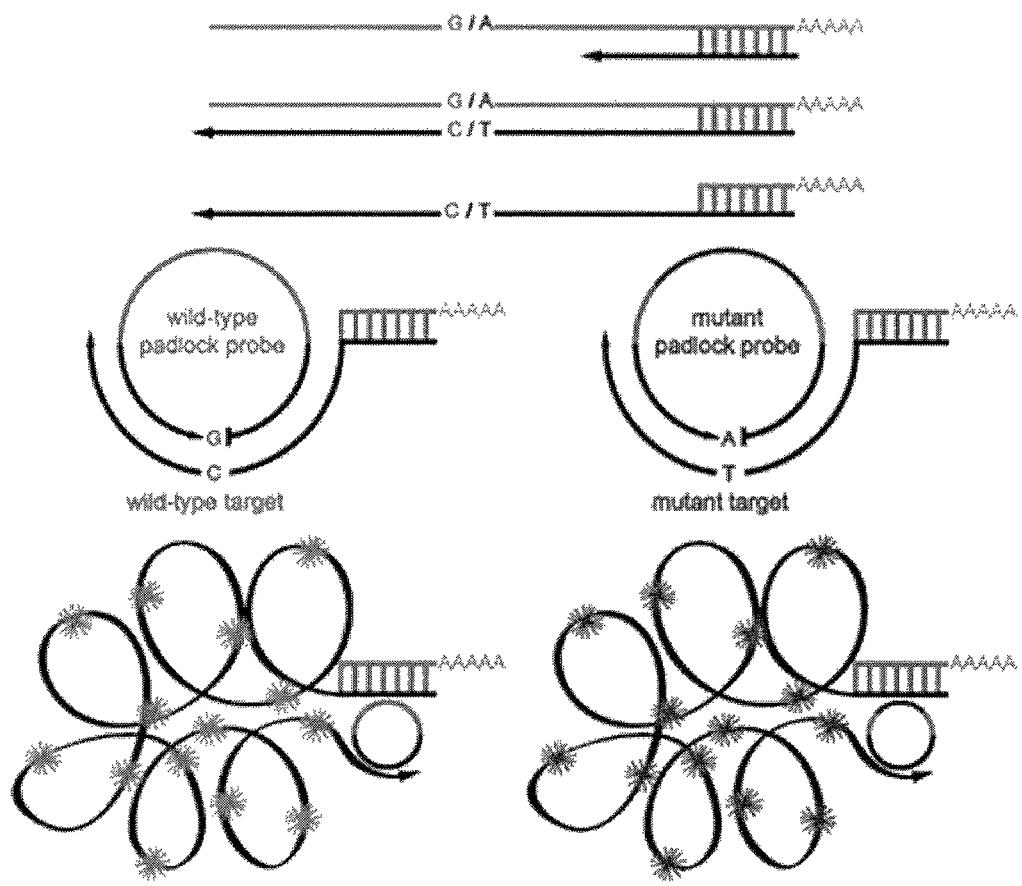
FIG. 8: Schematic overview for in situ genotyping with padlock probes and target-primed RCA. KRAS cDNA (black) is created by reverse transcription with an LNA-primer. Target mRNA (grey) is degraded by RNase H, except for the region that is hybridized to the LNA-part of the primer that is protected from degradation, anchoring the created cDNA to the target. KRAS genotype specific padlock probes, with similar target sites except for the single point mutated base (GGT→AGT), are hybridized to the cDNA and circularized by target-dependent ligation. The targeted KRAS transcripts act as primer for RCA and the resulting RCPs are labeled with fluorescence-labeled detection probes and visualized as bright spots in the cells or tissue.

The method of the invention was also used to genotype a KRAS point mutation in KRAS wild-type and mutant cells (FIG. 7). The different cell types could be clearly distinguished on the basis of the color of their corresponding RCPs. Activating mutations of the KRAS oncogene are found in 17%-25% of all human tumors, and assays to monitor these mutations and other tumor cell-specific markers in tissue specimens in situ could be of great value for clinical pathology investigations. The potential for studies of allelic expression was further investigated by analyzing 77 cells from a cell line heterozygous for a point mutation in KRAS. An average allelic ratio of 48% wild-type transcripts was observed, with considerable cell-to-cell variation (FIGS. 6b and 7), indicating a balanced allelic transcription. In this experiment, all heterozygous cells with more than seven RCPs showed signals from both alleles. For cells showing fewer than seven signals, it will be difficult to determine the potential for biallelic expression and extent of unbalanced allelic expression in single cells.

Example 8

Effect of LNA Base Incorporation in the cDNA Primer

Figure 3:
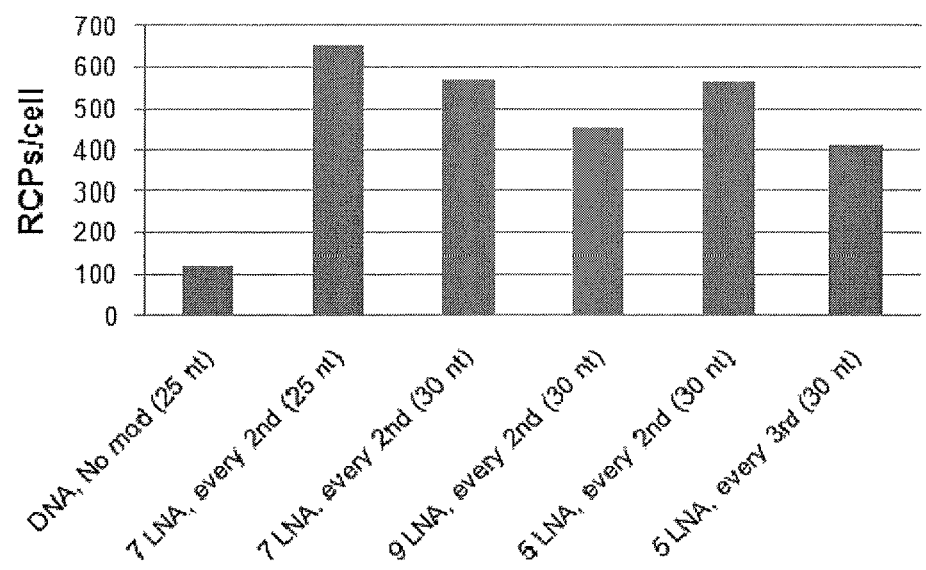
FIG. 3: Effect of LNA base incorporation in the primer for cDNA synthesis in situ. cDNA primers with different LNA substitutions were compared against an unmodified primer consisting of only DNA bases (No mod) for cDNA synthesis in situ. Synthesized cDNA was detected with padlock probes and target-primed RCA and quantified by counting RCPs/cell. The investigated primers had five, seven or nine LNA bases positioned either at every second or every third position in the 5'-end of the primers. Primers had a total length of 25 nt or 30 nt (indicated in parentheses).

To increase the efficiency of the reverse transcription step, a RT primer with incorporated locked nucleic acid (LNA)-bases was used. LNA modified oligonucleotides have previously been used for FISH, with DNA/LNA mixmers with every second or third base substituted for LNA performing the best. In addition to the increased hybridization efficiency to the targets, the LNA content of the primers can be designed to protect the target RNA from breakdown by RNase H. This means that in the present method, the in situ synthesized cDNA can maintain the localization to the detected mRNA molecule in the cell via the hybridization of the cDNA primer (FIG. 1). cDNA primers with different LNA substitutions (Table 2) were tested in situ for subsequent detection of the PLP-βe1 padlock probe target site. It was found that primers with every second base at the 5'-end substituted with LNA performed better than primers with substitutions of every third base (FIG. 3). Primers with five, seven or nine LNA bases in total were also investigated and it was found that adding nine LNA bases resulted in a small decrease in the amount of signals in situ. To ensure that the LNA would not interfere with the ability of the reverse transcriptase to synthesize cDNA from the primer, LNA bases were placed on the 5'-side of the primers, leaving the 3'-end unmodified. It was found that shortening the total length of the primer from 30 to 25 nucleotides did not influence the results, and thus it was concluded that the priming is not disturbed by the presence of LNA bases in the primer.

Example 9 cDNA Synthesis Efficiency

Figure 4:
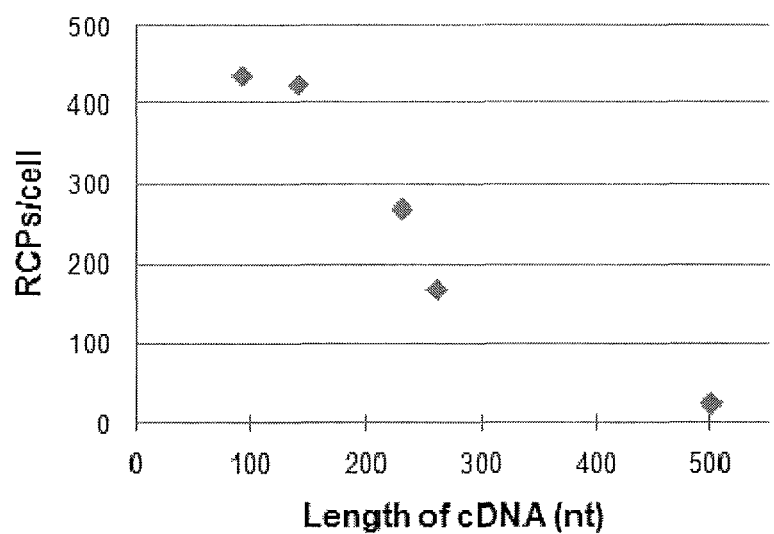
FIG. 4: Investigation of cDNA synthesis length. Primers positioned at different distances from the mRNA 5'-end, where the target site of the PLP-βe1 padlock probe is located, were compared for in situ detection of β-actin transcripts with padlock probes and target-primed RCA to investigate the efficiency of the cDNA synthesis. When reverse transcription was carried out without addition of any primer, an average of seven RCPs were detected per cell (not shown in diagram).

To ensure an optimal distance between hybridizing cDNA primers and target sequences for the padlock probes, the length of the produced cDNA molecules in cells was investigated. An in situ detection experiment was set with cDNA primers located at different distances from the 5'-end of the β-actin mRNA. Reverse transcription was then performed in situ and the resulting cDNA molecules were detected with PLP-βe1, with a target sequence near the 3'-end of the reverse transcribed cDNA. The number of RCPs formed per cell was then quantified for the different primers. The primers tested were to result in cDNA molecules ranging from approximately 90-500 nt in length, measured from the start of the primer site to the end of the transcript (see Table 3 for primer sequences). It was found that predominantly short molecules were formed and that the cDNA primer site should be located close to the padlock probe target site (FIG. 4). As well as providing details on how to design primers for reverse transcription, the knowledge about the limited cDNA synthesis length has a practical relevance for the execution of the RCA reaction. In this protocol a target-priming strategy was used that was originally described for endogenous mitochondrial DNA molecules in situ (Larsson et al., 2004). Target-priming takes advantage of a 3'-5' exonuclease activity of the φ29 DNA polymerase on single stranded DNA to create a primer from a nearby 3'-end of the target molecule. The efficiency of the RCA reaction has been shown to decrease as the length of the protruding 3'-end of mitochondrial DNA is increased from 0 to 130 nucleotides. As very short cDNA molecules were produced in this method, the target-primed RCA approach can efficiently be applied for signal amplification also for cDNA detection without further preparation of the target strand.

Example 10

Different Ligases for Ligation of Padlock Probes

There are mainly two enzymes that have been used for padlock probe ligation previously; the ATP dependent T4 DNA ligase and the NAD+dependent Ampligase™. Both ligases were tested for in situ detection of cDNA with padlock probes, good detection efficiencies were obtained. However, when performing the experiments for detection of sequences with single nucleotide resolution in human and mouse cells, it was found that Ampligase resulted in a lower proportion of signals from the non-matched probe. The proportion of correct signals with T4 DNA ligase was 87% (human RCPs/total RCPs) for human cells and 98% (mouse RCPs/total RCPs) for mouse cells. This is in contrast to Ampligase™, which had a much higher selectivity for the human target sequence (98% correct) whereas the mouse target sequence was unchanged compared to T4 DNA ligase. As the transcripts of the different actin isoforms share a high proportion of similarity and many pseudogenes exist, it is believed that some of these unexpected positive signals originate from sequences similar to the padlock probe target sequence that do not show up when performing simple in silico sequence analysis. In addition to these observations, Ampligase™ is known to be more specific for matched substrates than T4 DNA ligase.

Example 11

Assay Design for In Situ Mutation Detection

Padlock probes were designed for point mutations of KRAS in codon 12 and 13 (G12S, G12R, G12C, G12D, G12A, G12V and G13D) and codon 61 (Q61H), as well as for EGFR (G719A, G719C, S768I and L858R) and TP53 (S127F and P190S). Padlock probes for the wild-type forms of the different targets were designed as well. The mutation-specific padlock probes were designed with identical target sequences except for the last nucleotide in the 3'-end that differ depending on genotype. Mismatches at this position are not accepted by the DNA ligase used and single nucleotide differences, like point mutations, are therefore efficiently discriminated. There are furthermore two different sites for detection probes for wild-type and mutant padlocks to distinguish the RCPs from each other using detection probes labeled with different fluorescence dyes, e.g. green and red. Also detection of the ACTB transcript was included in these assays, detected by an additional fluorophore, as an internal reference having a relative constant expression between cell types. A comparison of the ACTB signals across samples provided an estimation of the detection efficiency in different samples. The ACTB data has been useful during the development phase of this study, but turned out to be dispensable for mutation scoring and tissue classification.

Example 12

Mutation Detection in Fresh Frozen Colon and Lung Tissues with Known KRAS Status The selectivity of the padlock probes was first tested in situ on wild-type- and mutation-specific KRAS cell lines. After confirmation of the quality of the probes, our in situ genotyping method was applied on ten fresh frozen human colon and lung cancer tissues with known KRAS status. In this validation phase, each probe-pair (one probe for a particular mutation and one for the corresponding wild-type variant) was tested individually on a collection of fresh-frozen tissue samples with known KRAS status. Wild-type probes were designed to generate green fluorescence RCPs and mutation-specific probes to generate red fluorescence RCPs. The samples represented all codon 12 and 13 mutations except for the rarest one, G12R. However, the performance of the padlock probe pair for the G12R mutation was still verified for specificity on one of the tested cell lines. Thus, KRAS wild-type tumor tissues could be distinguished from ones having tumors carrying activating KRAS mutations by microscopic visualization in a fashion similar to regular fluorescent in situ hybridization (FISH). The colon and lung sections with KRAS mutations displayed a mixture of signals originating from both of the probes in the padlock probe pair, whereas the normal tissues showed signals exclusively from the wild-type padlock probe. By visually examining the ten samples variations can clearly be seen in KRAS expression levels both within and between the tissues. Overall, a slightly higher expression level of KRAS was noticed in lung compared to colon. The results showed that most cases displayed both wild-type and mutant KRAS signals in the tumor cell areas indicating heterozygous expression. In contrast, one lung sample almost exclusively displayed mutant signals in the tumor regions while the few existing wild-type signals belonged to the normal surrounding stroma. This could reflect a KRAS homozygous mutation or loss-of-heterozygosity (LOH).

Example 13

Mutation Detection in FFPE Tissue

The in situ padlock probe technique was tested to evaluate whether it could be applicable on FFPE tissue. The protocol applied on this type of tissue material was essentially the same as for fresh frozen tissues, except for the pretreatment procedure. KRAS mutation analysis was performed on a collection of 14 colorectal FFPE cancer tissues with known KRAS mutations in codon 12 and 13 applying the respective padlock probe-pair. All tissues displayed a mixture of signals originating from both the wild-type and mutant padlock probe, however variation in the number of signals (for both KRAS and ACTB) were significant between tissues, which probably reflects the expected difference in tissue quality among FFPE samples. Moreover, the ratio between wild-type and mutant signals was also observed to differ between tissues carrying the same KRAS mutation which probably reflects tumor-specific characteristics. Probes were also designed for the most common mutation in codon 61 (Q61H) and tested in two colon tumor FFPE samples that successfully were scored as mutants.

Example 14

In Situ Detection of KRAS Mutations on Prospective Clinical Samples with Unknown Mutation Status After the initial verification that the padlock probes are selective, all probes were combined into single reactions that could answer the primary diagnostic question whether a case is KRAS positive or not. This was tested by comparing in situ mutation detection using single pairs of KRAS mutation-specific padlock probes with a multiplex detection approach using a padlock probe cocktail containing all probes for KRAS codon 12 and 13 mutations. The results, based on visual examinations of the tissues, indicated that neither efficiency nor selectivity were lost when multiple probes were in competition for the two-codon target site. The analysis thus provides a rapid answer if the tumor harbors an activating KRAS mutation or not. Nevertheless, if requested there is still a possibility with this technique to reveal the exact sequence alteration by simply testing for all mutations individually on consecutive sections.

Multiplex mutation detection was thereafter demonstrated on eight prospective lung FFPE tissues with unknown KRAS mutations status. Approximately 15-30% of all lung cancer cases have activating KRAS mutations. After performing mutation analysis with padlock probes and RCA, three of the eight cases were concluded to be mutated. The results were compared with pyrosequencing on the same tissues and the suggested genotypes were confirmed to be correct for every case.

To test the method in a diagnostic setting involving cytology preparation tumor imprint slides were prepared from eight prospective fresh colon cancer specimens with unknown KRAS mutation status. Multiplex KRAS mutation detection using padlock probes and target-primed RCA were prepared using the protocol for unfixed tissue. By microscopic examination of the imprints, two cases were found to be positive in the in situ mutation assay, while the other six tumor imprints only showed wild-type signals. DNA from corresponding FFPE tumor sections from the same cases were thereafter tested for KRAS mutations by pyrosequencing. The pyrosequencing results were completely concordant with the in situ assay.

Example 15

High-Throughput Mutation Screening on Tissue Microarrays

Tissue microarrays (TMA) can be used to analyze hundreds of patient FFPE tumor samples on one slide, and have been used to characterize protein expression (by immunohistochemistry (IHC)) and gene copy number variations (by FISH) in large patient cohorts. Here a TMA containing 25 FFPE colon samples (in duplicates) was assayed for possible KRAS codon 12 and 13 mutations. The array consisted of samples from normal colon mucosa, tubular adenomas, serrated adenomas, primary tumors and matched metastasis, all with unknown mutation status for KRAS. Of all samples eleven were found to be KRAS positive—two adenomas, one serrated adenoma, four primary tumors and their matched metastasis. Mutation analysis by pyrosequencing on the corresponding FFPE blocks was completely concordant with the in situ data (Supplementary FIG. 12).

Example 16

Differential Expression of Mutated Oncogene Alleles Related to Tumor Progression and Histological Heterogeneity Variable expression of a mutated oncogene across a tumor could potentially result in a variable response to targeted therapy in different areas of a single cancer lesion. Therefore, cases were screened with the in situ assay for distinct patterns of expressed mutations. In one colon cancer case with a codon 61 mutation, the histological progression from normal colon mucosa to low-grade and high-grade dysplasia and invasive carcinoma could be visualized on a single slide. There was a clear increase in the expression of the mutation along with tumor progression. Thus, one can speculate if the level of resistance to EGFR inhibitors would follow the expression levels in the different neoplastic compartments.

Also, the EGFR L858R mutation was targeted in a set of nine FFPE lung tissues in which eight were known to be positive. The results from the in situ mutation assay were completely concordant with the DNA sequencing data. Even though some of the lung samples were collected more than a decade ago high detection efficiency was observed with high numbers of signals, especially mutant signals, which might reflect high mRNA expression from amplified EGFR in the tumor. In one lung sample a great histological heterogeneity was observed with regard to tumor growth patterns. Wild-type EGFR was only expressed in normal bronchial epithelium. In areas with bronchioalveolar/lepidic growth pattern the expression of mutated EGFR was low, and equaled the expression of the wild-type allele. The expression of the mutant allele increased in more poorly differentiated glandular areas, both in absolute numbers and relative to the wild-type allele. The expression of mutant EGFR peaked in areas with solid growth pattern. Thus, if the expression level of L858R affects the sensitivity of a tumor clone for EGFR-TKI therapy, the poorly differentiated areas of the tumor would be expected to respond better than the well differentiated areas in this individual tumor.

Example 17

Expression Patterns in Tumors with Multiple Mutations

To further study intra-tumor heterogeneity, probes were designed for tumors that were known to harbor multiple point mutations. Personalized medicine implies therapy tailored to the individual characteristics of a patient. The advent of next-generation sequencing technology is now increasingly providing researchers, and soon probably clinicians, with mutational profiles of individual tumors that taken together may provide improved opportunities for individualized therapy. Sequencing DNA prepared from a part of a tumor will reveal all mutations in that sample but not if they reside in different sub-clones of the tumor. As a proof-of-concept that intergenic tumor heterogeneity can be studied with our technology, individualized in situ mutation assays were set up for screening of FFPE cases carrying unique combinations of mutations in EGFR, KRAS, and TP53.

One lung cancer case was positive for the activating EGFR mutation G719C as well as the EGFR S768I mutation that is associated with resistance to anti-EGFR therapy. Both mutation variants were successfully detected with the padlock probe-based in situ technique and their individual expression patterns were identified. The expression of the G719C mutation was high compared to the S768I mutation throughout the tumor section. This balance between the expressed mutated alleles might be expected as that this case represents a patient that had not received anti-EGFR therapy so no selection pressure for increased expression of the resistance mutation was present.

Another lung FFPE sample was assayed for a G719A EGFR mutation in combination with a S127F mutation of the tumor suppressor gene TP53. The in situ analysis of this tissue showed cells in stromal regions that only expressed the wild-type form of TP53 while no expression of any of the EGFR alleles could be detected. Hematoxylin and eosin (HE) staining of this tissue sample confirmed that the cell populations with wild-type TP53 were lymphocytes. The TP53 S127F mutation-positive tumor regions displayed signals from both the wild-type EGFR and G719A padlock probes but none from wild-type TP53 padlock probe, indicating TP53 LOH.

A set of padlock probes was applied on a FFPE lung tissue sample with reported KRAS G12C and TP53 P190S mutations. In contrast to the previous case, in which the wild-type and mutant TP53 signals were located in different compartments (stroma and tumor respectively), here the mutant and wild-type TP53 transcripts were expressed in a heterozygous fashion in the tumor compartment. Similarly the wild-type and mutant KRAS signals were evenly distributed across the tumor areas with a higher expression of mutant compared to wild-type KRAS alleles. This difference in expression pattern of the wild-type and mutant alleles in the two cases would not have been identified unless an in situ technique was included as a complement to DNA sequencing. Moreover, since this in situ assay reveals information on a single cell level, unique information (e.g. expression of more than one mutation in the same cell, can be identified and studied in detail. Co-localization of different alleles in the same cell provides strong evidence of their co-existence in cells in the tumor while absence of co-localization does not prove that they are not co-expressed in a certain cell-lineage. Even though all four alleles were not detected in any of these cells, the most likely interpretation of the staining pattern in is that the KRAS mutation is carried by all TP53 mutation-positive cells.

Discussion of Examples 11 to 17

Examples 11 to 17 document the establishment of a multiplex in situ assay that specifically targets point mutations on tumor tissue sections and on cytological preparations. Transcripts, synthesized by reverse transcription of mRNA in situ, are targeted with mutant- or wild-type specific padlock probes and amplified to a detectable level with RCA. The resulting wild-type and mutated products are thereafter labeled with fluorophores of different colors. This padlock probe-based assay demonstrates for the first time that mutation analysis for molecular cancer diagnostics can be performed directly on tumor tissue sections. A multiplexed in situ assay was developed and validated as a proof-of-concept for the activating point mutations in KRAS codon 12 and 13 that are associated with resistance to anti-EGFR therapy in colorectal cancer. The selectivity of the probes was first tested individually. There was a clear-cut distinction between the KRAS mutant and wild-type samples and the genotypes were easily determined by simple microscopic visualization of the corresponding fluorescent signals. For multiplex detection, a side-by-side comparison between single corresponding padlock pairs and a cocktail of all codon 12 and 13 KRAS padlock probes showed that the two approaches were similar in efficiency and specificity. The padlock strategy was developed on unfixed tissue preparations as fresh frozen tissue contains high quality DNA and RNA and serves as the golden standard for molecular studies. However, implementation of diagnostics on fresh frozen tissue requires substantial and expensive biobanking efforts. As an alternative, unfixed tumor cells were used on touch imprints from the fresh cut tumor surface. The KRAS mutation status could thus be determined on the day of sample arrival and was concordant with our routine pyrosequencing assay.

FFPE tissue blocks are used globally in routine surgical pathology and can be preserved for years in tissue archives. However, crosslinking of biomolecules induced by formalin results in fragmentation of DNA and RNA. Nevertheless, the short length of the padlock probe, in combination with the requirement of dual recognition sites and ligation makes this assay ideal for fixed histopathology specimens. Using a protocol optimized for formalin-fixed tissues in situ detection in routine FFPE sections was achieved and prospective surgical cancer specimens with unknown KRAS status were successfully characterized. A promising prospect for this assay is that hundreds of FFPE cancer samples can be screened simultaneously in TMAs for presence of mutations. Thus, for biomarker discovery in retrospective patient cohorts with available TMAs, high-throughput screening for point mutations could be performed along with IHC for protein expression and FISH-analysis for chromosomal aberration. The in situ protocol can be adapted for automation as any conventional FISH-assay, facilitating implementation of the assay for routine use. Moreover, the fluorescence readout can be changed to a histochemical staining for brightfield imaging if desired.

Tumor heterogeneity is a complex concept. One aspect is the variable mixture of cancer cells with acquired somatic mutations and genetically normal stromal and inflammatory cells. A second aspect is the morphological, and possibly genetic, variation within the tumor compartment with regard to pre-neoplastic versus invasive components, high-grade versus low-grade areas, invasion front versus central tumor area, and variable differentiation patterns, e.g. sarcomatoid, glandular, squamous or neuroendocrine etc. A third aspect is that the expression of a mutated allele can be influenced by promoter and splicing mutations, epigenetic alteration, or gene copy number aberrations, e.g. amplifications, deletions and LOH, in different parts of the tumor. These may be challenging to analyze on a genomic level. The described in situ technique allows studies of all these challenging features of tumor heterogeneity. Heterozygous and homozygous expression of mutated and wild-type alleles can be appreciated in tumor cells and demonstrate one form of fundamental information about a particular tissue specimen that probably would have gone undetected with PCR-based techniques resulting in an average value of the extracted mixture of mutant tumor and wild-type cells. This assay shows increased expression of a mutated KRAS codon 61 allele along with tumor progression in a colon cancer sample. In a case of lung adenocarcinoma, the expression of an activating EGFR mutation was demonstrated to be different in areas with distinctive histological architecture. Moreover, the technique allows dissection of how multiple different mutations are distributed and associated across a tumor lesion, as illustrated by two lung cancer cases where mutated TP53 alleles could be visualized together with activating mutations in EGFR and KRAS respectively. Thus, mutation analysis in situ can help to dissect processes such as cancer initiation, tumor progression and metastasis. For future studies an intriguing application will be studies of the emergence of resistance mutations in response to targeted therapy. One case with a double mutation in EGFR was presented where low expression of the resistance mutation was seen in parallel with expression of the mutation associated with treatment response, as might be expected in a patient with a de novo resistance mutation. Analysis of a follow-up sample after EGFR treatment could reveal a patient-specific response on a histological level regarding the expression of the two mutations.

Despite the fact that the 79 patient samples assayed in this study had been collected at different time points during the last two decades, as well as treated under various conditions, they all qualified as suitable tissue material for this presented method. Furthermore, specifically designed padlock probes were successfully applied for in situ detection of totally 14 different point mutations which give confidence that this mutation assay offers robustness and can easily be adapted for detection of other mutations on tissue material from various sources. In conclusion, the presented padlock probe and RCA technology is believed to be an important assay for studies of histologic-genotypic correlations in complex tumor tissues for diagnostic molecular pathology and translational cancer research.

Example 18

Detection of Braf Mutations

BRAF presents somatic mutations in different sort of tumors, predominantly in malignant melanoma, sporadic colorectal tumors showing mismatch repair defects in microsatellites (MSI), low-grade ovarian serous carcinoma and thyroid papillary cancer. 80% of these mutations correspond to the hotspot transversion mutation T1799A that causes the amino acidic substitution V600E.

Most common mutation is the V600E mutation (Substitution—Missense)
Target cDNA Region (Mutated Base):

```
                                            (SEQ ID NO: 100)
5'-GCATATACATCTGACTGAAAGCTGTATGGATTTTTATCTTGCATTCT

GATGACTTCTGGTGCCATCCACAAAATGGATCCAGACAACTGTTCAAACT

GATGGGACCCACTCCATCGAGATTTCACTGTAGCTAGACCAAAATCACCT

A-3'
```

BRAF Padlock Probe Target Region (arms: 15+15 nt):

```
                            (SEQ ID NO: 101)
    5'-CTCCATCGAGATTTCACTGTAGCTAGACCA-3'
```

REFERENCES

The following references, to the extent that they provide exemplary procedural or other details supplementary to those set forth herein, are specifically incorporated herein by reference.

Botling and Micke, *Methods Mol. Biol.*, 675:299-306, 2011.
Lagunavicius et al., *RNA*, 15:765-771, 2009.
Larsson et al., *Nat. Methods*, 1:227-232, 2004.
Lizardi et al., *Nat. Genet.*, 19:225-232, 1998.
Mitra and Church, *Nucleic Acids Res.*, 27(24), 1999.
Nilsson et al., *Nat. Biotechnol.*, 18:791-793, 2000.
Nilsson et al., *Nucleic Acid Res.*, 29:578-581, 2001.
Nilsson et al., *Science*, 265:2085-2088, 1994.
Owczarzy et al., *Biochemistry*, 47:5336-5353, 2008.

PCT Appln. WO 99/49079
Pena et al., *Nat. Methods,* 6(2):139-141, 2009.
Sambrook et al., Molecular Cloning—A Laboratory Manual, Cold Spring Harbor Laboratory, NY, 1989.
Stougaard et al., *BMC Biotech.,* 7:69, 2007.
Sundstrom et al., *BMC Cancer,* 10:660, 2010.
Wetmur, *Critical Rev. Biochem. Mol. Biol.,* 26(3/4):227-259, 1991.
Yi et al., *Nucleic Acid Res.,* 29:4818-4825, 2001.

What is claimed is:

1. A method for localized in situ detection of at least one target RNA in a sample of one or more cells that was formalin-fixed paraffin-embedded (FFPE), comprising:
   generating a cDNA complementary to an RNA in the sample;
   adding a ribonuclease to said sample to digest the RNA hybridized to said cDNA;
   contacting said sample with one or more padlock probes wherein said padlock probe(s) comprise terminal regions complementary to said cDNA and hybridizing said padlock probe to the cDNA at said complementary terminal regions;
   circularising said padlock probe(s) by ligating, directly or indirectly, the ends of said padlock probe(s);
   subjecting said circularized padlock probe(s) to rolling circle amplification (RCA);
   detecting the rolling circle amplification product(s).

2. The method of claim 1 wherein the RNA is mRNA.

3. The method of claim 1, wherein generating the cDNA complementary to the RNA in the sample comprises contacting said sample with a reverse transcriptase and a reverse transcription primer.

4. The method of claim 3, wherein the reverse transcription primer is ribonuclease resistant.

5. The method of claim 4, wherein the reverse transcription primer comprises 2'O-Me RNA, methylphosphonates or 2' Fluor RNA bases, locked nucleic acid residues, or peptide nucleic acid residues.

6. The method of claim 5, wherein the reverse transcription primer comprises one or more locked nucleic acid residues.

7. The method of claim 1, further comprising contacting the sample with an exonuclease to digest the cDNA to generate a free 3' end which acts as a primer for said RCA.

8. The method claim 1, wherein in said contacting step, said sample is contacted with at least a first and a second padlock probe, wherein said first padlock probe comprises terminal regions complementary to immediately adjacent regions on said cDNA, and wherein said second padlock probe comprises terminal regions that differ from the terminal regions of said first padlock probe only by a single nucleotide at the 5' or 3' terminus of said second padlock probe.

9. The method of claim 8, wherein said first padlock probe comprises a first detection probe binding region, and said second padlock probe comprises a second detection probe binding region.

10. The method of claim 9, further comprising contacting said sample with at least a first labeled detection probe comprising a sequence identical to the first detection probe binding region of the first padlock probe, and a second labeled detection probe comprising a sequence identical to the second detection probe binding region of the second padlock probe, and hybridizing said first and second labeled detection probes to the rolling circle amplification products.

11. The method of claim 10, further comprising detecting a signal from said first labeled detection probe hybridized to the rolling circle amplification product, or detecting a signal from said second labeled detection probe hybridized to the rolling circle amplification product, or detecting a signal from both said first and second labeled detection probes hybridized to the rolling circle amplification products, wherein the detection of said first labeled detection probe indicates the presence of wild-type mRNA in the cell and the detection of said second labeled detection probe indicates the presence of variant mRNA in the cell.

12. The method of claim 1, wherein multiple different RNAs are detected using multiple different padlock probes.

13. The method of claim 1, wherein the sample is suspected to comprise an RNA found in a cancer cell.

14. A method for localized in situ detection of mRNA which codes for one or more mutations of the KRAS gene in a sample of cells that was formalin-fixed paraffin-embedded (FFPE) on a slide surface, comprising:
   (a) generating cDNA from mRNA in the sample using a primer,
   (b) digesting the mRNA hybridized to said cDNA;
   (c) contacting said sample with one or more padlock probes specific for mutations to the KRAS gene.

15. The method of claim 14 further comprising:
   (d) joining, directly or indirectly, the ends of said padlock probe(s);
   (e) subjecting said circularized padlock probe(s) to rolling circle amplification (RCA) to generate rolling circle amplification product(s); and
   (f) detecting the rolling circle amplification product(s).

16. The method of claim 14, wherein the primer comprises 2'O-Me RNA, methylphosphonates or 2' Fluor RNA bases, peptidyl nucleic acid residues, or locked nucleic acid residues.

17. The method of claim 14, wherein multiple different KRAS mutations are detected using multiple different padlock probes.

18. A method for determining the presence and/or location of a genetic sequence in a cell in a biological sample that was formalin-fixed paraffin-embedded (FFPE) comprising:
   a) hybridizing a DNA complement having the genetic sequence to RNA in the biological sample;
   b) digesting RNA hybridized to the DNA complement;
   c) hybridizing a first padlock probe to at least a portion of the DNA complement, wherein the padlock probe comprises the genetic sequence on one of two terminal ends that are complementary to different but immediately adjacent regions of the DNA complement;
   d) joining the two terminal ends of the padlock probe to form a circularized probe;
   e) replicating the circularized probe to yield a nucleic acid molecule comprising multiple copies of the replicated probe; and
   f) detecting presence, absence, and/or location of the genetic sequence in the cell using a probe that hybridizes to the nucleic acid molecule.

19. The method of claim 18, further comprising generating the DNA complement.

20. The method of claim 19, wherein the DNA complement is generated using a primer that is ribonuclease resistant.

21. The method of claim 18, wherein the circularized probe is replicated using a polymerase having 3'-5' exonuclease activity.

22. The method of claim 21, wherein the circularized probe is incubated under conditions to generate a free 3' end on the DNA complement that acts as a primer for replication of the circularized probe.

23. The method of claim 18, further comprising adding a second padlock probe that is complementary to a second genetic sequence.

24. A method for in situ detection and/or localization of a specific RNA in a cell from a formalin-fixed paraffin-embedded (FFPE) biological sample on a solid support comprising:
   a) incubating an immobilized FFPE biological sample on solid support with reverse trancriptase and a ribonuclease-resistant primer under conditions to generate a DNA molecule complementary to the specific RNA to form an RNA-DNA hybrid;

b) adding a ribonuclease and incubating the ribonuclease under conditions to digest RNA in the RNA-DNA hybrid;
c) incubating the digested RNA-DNA hybrid under conditions to hybridize a complementary padlock probe to the DNA portion of the digested RNA-DNA hybrid, wherein the padlock probe comprises two terminal ends that are complementary to different but immediately adjacent regions of the DNA molecule;
d) incubating the padlock probe hybridized to the DNA portion of the RNA-DNA hybrid with a ligase under conditions to ligate the terminal ends of the padlock probe;
e) incubating the ligated padlock probe with a polymerase and nucleotides under conditions to create a primer from the DNA that is used to replicate the padlock probe and generate a nucleic acid comprising multiple copies of the replicated padlock probe; and,
f) incubating the nucleic acid with one or more complementary nucleic acid probes to detect the presence, absence, or location of the specific RNA in the cell.

25. The method of claim 24, further comprising adding a second padlock probe that is complementary to a second specific RNA.

* * * * *

UNITED STATES PATENT AND TRADEMARK OFFICE
CERTIFICATE OF CORRECTION

PATENT NO. : 8,551,710 B2
APPLICATION NO. : 13/542378
DATED : October 8, 2013
INVENTOR(S) : Mats Nilsson Bernitz et al.

Page 1 of 1

It is certified that error appears in the above-identified patent and that said Letters Patent is hereby corrected as shown below:

On the Title page, Item (73) Assignee, line 2, delete "NewCastle" and insert --Newcastle-- therefor.

Signed and Sealed this
Twenty-sixth Day of November, 2013

Margaret A. Focarino
*Commissioner for Patents of the United States Patent and Trademark Office*

SEQUENCE LISTING

```
<160> NUMBER OF SEQ ID NOS: 112

<210> SEQ ID NO 1
<211> LENGTH: 15
<212> TYPE: DNA
<213> ORGANISM: Artificial Sequence
<220> FEATURE:
<223> OTHER INFORMATION: Synthetic primer

<400> SEQUENCE: 1
gtggcgtagg caaga                                                    15

<210> SEQ ID NO 2
<211> LENGTH: 14
<212> TYPE: DNA
<213> ORGANISM: Artificial Sequence
<220> FEATURE:
<223> OTHER INFORMATION: Synthetic primer

<400> SEQUENCE: 2
gtggcgtagg caag                                                     14

<210> SEQ ID NO 3
<211> LENGTH: 13
<212> TYPE: DNA
<213> ORGANISM: Artificial Sequence
<220> FEATURE:
<223> OTHER INFORMATION: Synthetic primer

<400> SEQUENCE: 3
gtggcgtagg caa                                                      13

<210> SEQ ID NO 4
<211> LENGTH: 12
<212> TYPE: DNA
<213> ORGANISM: Artificial Sequence
<220> FEATURE:
<223> OTHER INFORMATION: Synthetic primer

<400> SEQUENCE: 4
gtggcgtagg ca                                                       12

<210> SEQ ID NO 5
<211> LENGTH: 11
<212> TYPE: DNA
<213> ORGANISM: Artificial Sequence
<220> FEATURE:
<223> OTHER INFORMATION: Synthetic primer

<400> SEQUENCE: 5
gtggcgtagg c                                                        11

<210> SEQ ID NO 6
<211> LENGTH: 10
<212> TYPE: DNA
<213> ORGANISM: Artificial Sequence
<220> FEATURE:
<223> OTHER INFORMATION: Synthetic primer

<400> SEQUENCE: 6
```

```
gtggcgtagg                                                          10

<210> SEQ ID NO 7
<211> LENGTH: 15
<212> TYPE: DNA
<213> ORGANISM: Artificial Sequence
<220> FEATURE:
<223> OTHER INFORMATION: Synthetic primer

<400> SEQUENCE: 7
tggcgtaggc aagag                                                    15

<210> SEQ ID NO 8
<211> LENGTH: 14
<212> TYPE: DNA
<213> ORGANISM: Artificial Sequence
<220> FEATURE:
<223> OTHER INFORMATION: Synthetic primer

<400> SEQUENCE: 8
tggcgtaggc aaga                                                     14

<210> SEQ ID NO 9
<211> LENGTH: 13
<212> TYPE: DNA
<213> ORGANISM: Artificial Sequence
<220> FEATURE:
<223> OTHER INFORMATION: Synthetic primer

<400> SEQUENCE: 9
tggcgtaggc aag                                                      13

<210> SEQ ID NO 10
<211> LENGTH: 12
<212> TYPE: DNA
<213> ORGANISM: Artificial Sequence
<220> FEATURE:
<223> OTHER INFORMATION: Synthetic primer

<400> SEQUENCE: 10
tggcgtaggc aa                                                       12

<210> SEQ ID NO 11
<211> LENGTH: 11
<212> TYPE: DNA
<213> ORGANISM: Artificial Sequence
<220> FEATURE:
<223> OTHER INFORMATION: Synthetic primer

<400> SEQUENCE: 11
tggcgtaggc a                                                        11

<210> SEQ ID NO 12
<211> LENGTH: 10
<212> TYPE: DNA
<213> ORGANISM: Artificial Sequence
<220> FEATURE:
<223> OTHER INFORMATION: Synthetic primer

<400> SEQUENCE: 12
tggcgtaggc                                                          10

<210> SEQ ID NO 13
<211> LENGTH: 18
<212> TYPE: DNA
<213> ORGANISM: Artificial Sequence
```

-continued

```
<220> FEATURE:
<223> OTHER INFORMATION: Synthetic primer

<400> SEQUENCE: 13
tggcgtaggc aagagtgc                                                 18

<210> SEQ ID NO 14
<211> LENGTH: 17
<212> TYPE: DNA
<213> ORGANISM: Artificial Sequence
<220> FEATURE:
<223> OTHER INFORMATION: Synthetic primer

<400> SEQUENCE: 14
tggcgtaggc aagagtg                                                  17

<210> SEQ ID NO 15
<211> LENGTH: 16
<212> TYPE: DNA
<213> ORGANISM: Artificial Sequence
<220> FEATURE:
<223> OTHER INFORMATION: Synthetic primer

<400> SEQUENCE: 15
tggcgtaggc aagagt                                                   16

<210> SEQ ID NO 16
<211> LENGTH: 14
<212> TYPE: DNA
<213> ORGANISM: Artificial Sequence
<220> FEATURE:
<223> OTHER INFORMATION: Synthetic primer

<400> SEQUENCE: 16
ggtagttgga gctg                                                     14

<210> SEQ ID NO 17
<211> LENGTH: 13
<212> TYPE: DNA
<213> ORGANISM: Artificial Sequence
<220> FEATURE:
<223> OTHER INFORMATION: Synthetic primer

<400> SEQUENCE: 17
gtagttggag ctg                                                      13

<210> SEQ ID NO 18
<211> LENGTH: 12
<212> TYPE: DNA
<213> ORGANISM: Artificial Sequence
<220> FEATURE:
<223> OTHER INFORMATION: Synthetic primer

<400> SEQUENCE: 18
tagttggagc tg                                                       12

<210> SEQ ID NO 19
<211> LENGTH: 11
<212> TYPE: DNA
<213> ORGANISM: Artificial Sequence
<220> FEATURE:
<223> OTHER INFORMATION: Synthetic primer

<400> SEQUENCE: 19
agttggagct g                                                        11
```

```
<210> SEQ ID NO 20
<211> LENGTH: 10
<212> TYPE: DNA
<213> ORGANISM: Artificial Sequence
<220> FEATURE:
<223> OTHER INFORMATION: Synthetic primer

<400> SEQUENCE: 20
gttggagctg                                                              10

<210> SEQ ID NO 21
<211> LENGTH: 15
<212> TYPE: DNA
<213> ORGANISM: Artificial Sequence
<220> FEATURE:
<223> OTHER INFORMATION: Synthetic primer

<400> SEQUENCE: 21
agttggagct gggtg                                                        15

<210> SEQ ID NO 22
<211> LENGTH: 14
<212> TYPE: DNA
<213> ORGANISM: Artificial Sequence
<220> FEATURE:
<223> OTHER INFORMATION: Synthetic primer

<400> SEQUENCE: 22
gttggagctg ggtg                                                         14

<210> SEQ ID NO 23
<211> LENGTH: 13
<212> TYPE: DNA
<213> ORGANISM: Artificial Sequence
<220> FEATURE:
<223> OTHER INFORMATION: Synthetic primer

<400> SEQUENCE: 23
ttggagctgg gtg                                                          13

<210> SEQ ID NO 24
<211> LENGTH: 12
<212> TYPE: DNA
<213> ORGANISM: Artificial Sequence
<220> FEATURE:
<223> OTHER INFORMATION: Synthetic primer

<400> SEQUENCE: 24
tggagctggg tg                                                           12

<210> SEQ ID NO 25
<211> LENGTH: 11
<212> TYPE: DNA
<213> ORGANISM: Artificial Sequence
<220> FEATURE:
<223> OTHER INFORMATION: Synthetic primer

<400> SEQUENCE: 25
ggagctgggt g                                                            11

<210> SEQ ID NO 26
<211> LENGTH: 10
<212> TYPE: DNA
<213> ORGANISM: Artificial Sequence
<220> FEATURE:
<223> OTHER INFORMATION: Synthetic primer

<400> SEQUENCE: 26
```

```
gagctgggtg                                                          10

<210> SEQ ID NO 27
<211> LENGTH: 14
<212> TYPE: DNA
<213> ORGANISM: Artificial Sequence
<220> FEATURE:
<223> OTHER INFORMATION: Synthetic primer

<400> SEQUENCE: 27
tggtagttgg agct                                                     14

<210> SEQ ID NO 28
<211> LENGTH: 13
<212> TYPE: DNA
<213> ORGANISM: Artificial Sequence
<220> FEATURE:
<223> OTHER INFORMATION: Synthetic primer

<400> SEQUENCE: 28
ggtagttgga gct                                                      13

<210> SEQ ID NO 29
<211> LENGTH: 12
<212> TYPE: DNA
<213> ORGANISM: Artificial Sequence
<220> FEATURE:
<223> OTHER INFORMATION: Synthetic primer

<400> SEQUENCE: 29
gtagttggag ct                                                       12

<210> SEQ ID NO 30
<211> LENGTH: 11
<212> TYPE: DNA
<213> ORGANISM: Artificial Sequence
<220> FEATURE:
<223> OTHER INFORMATION: Synthetic primer

<400> SEQUENCE: 30
tagttggagc t                                                        11

<210> SEQ ID NO 31
<211> LENGTH: 10
<212> TYPE: DNA
<213> ORGANISM: Artificial Sequence
<220> FEATURE:
<223> OTHER INFORMATION: Synthetic primer

<400> SEQUENCE: 31
agttggagct                                                          10

<210> SEQ ID NO 32
<211> LENGTH: 25
<212> TYPE: DNA
<213> ORGANISM: Artificial Sequence
<220> FEATURE:
<223> OTHER INFORMATION: Synthetic primer

<400> SEQUENCE: 32
atcatccatg gtgagctggc ggcgg                                         25

<210> SEQ ID NO 33
<211> LENGTH: 25
<212> TYPE: DNA
<213> ORGANISM: Artificial Sequence
```

```
<220> FEATURE:
<223> OTHER INFORMATION: Synthetic primer

<400> SEQUENCE: 33
ctgacccatg cccaccatca cgccc                                           25

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
ctgacccatt cccaccatca caccc                                           25

<210> SEQ ID NO 35
<211> LENGTH: 25
<212> TYPE: DNA
<213> ORGANISM: Artificial Sequence
<220> FEATURE:
<223> OTHER INFORMATION: Synthetic primer

<400> SEQUENCE: 35
ttagagagaa gtggggtggc tttta                                           25

<210> SEQ ID NO 36
<211> LENGTH: 30
<212> TYPE: DNA
<213> ORGANISM: Artificial Sequence
<220> FEATURE:
<223> OTHER INFORMATION: Synthetic primer

<400> SEQUENCE: 36
gcgtccttgc tcgggtgttg taagttccag                                      30

<210> SEQ ID NO 37
<211> LENGTH: 30
<212> TYPE: DNA
<213> ORGANISM: Artificial Sequence
<220> FEATURE:
<223> OTHER INFORMATION: Synthetic primer

<400> SEQUENCE: 37
gagctgggtg cctcgcacaa tccgcagcct                                      30

<210> SEQ ID NO 38
<211> LENGTH: 30
<212> TYPE: DNA
<213> ORGANISM: Artificial Sequence
<220> FEATURE:
<223> OTHER INFORMATION: Synthetic primer

<400> SEQUENCE: 38
aggacacctg gcggaaggag ggggcggcgg                                      30

<210> SEQ ID NO 39
<211> LENGTH: 30
<212> TYPE: DNA
<213> ORGANISM: Artificial Sequence
<220> FEATURE:
<223> OTHER INFORMATION: Synthetic primer

<400> SEQUENCE: 39
actcgtcata ctcctgcttg ctgatccaca                                      30
```

```
<210> SEQ ID NO 40
<211> LENGTH: 25
<212> TYPE: DNA
<213> ORGANISM: Artificial Sequence
<220> FEATURE:
<223> OTHER INFORMATION: Synthetic primer

<400> SEQUENCE: 40
gcctcaggaa atcctggaag tctgc                                            25

<210> SEQ ID NO 41
<211> LENGTH: 70
<212> TYPE: DNA
<213> ORGANISM: Artificial Sequence
<220> FEATURE:
<223> OTHER INFORMATION: Synthetic primer

<400> SEQUENCE: 41
agcctcgcct ttgccttcct tttacgacct caatgctgct gctgtactac tcttcgcccc     60
gcgagcacag                                                             70

<210> SEQ ID NO 42
<211> LENGTH: 90
<212> TYPE: DNA
<213> ORGANISM: Artificial Sequence
<220> FEATURE:
<223> OTHER INFORMATION: Synthetic primer

<400> SEQUENCE: 42
gccggcttcg cgggcgacga ttcctctatg attactgacc tatgcgtcta tttagtggag     60
cctcttcttt acggcgccgg catgtgcaag                                       90

<210> SEQ ID NO 43
<211> LENGTH: 90
<212> TYPE: DNA
<213> ORGANISM: Artificial Sequence
<220> FEATURE:
<223> OTHER INFORMATION: Synthetic primer

<400> SEQUENCE: 43
gccggcttcg cgggcgacga ttcctctatg attactgacc taagtcggaa gtactactct     60
cttcttcttt acggcgccgg catgtgcaaa                                       90

<210> SEQ ID NO 44
<211> LENGTH: 90
<212> TYPE: DNA
<213> ORGANISM: Artificial Sequence
<220> FEATURE:
<223> OTHER INFORMATION: Synthetic primer

<400> SEQUENCE: 44
tacaggaagt cccttgccat ttcctctatg attactgacc tacctcaatg ctgctgctgt     60
actactcttc ccaaagatga gatgcgttgt                                       90

<210> SEQ ID NO 45
<211> LENGTH: 70
<212> TYPE: DNA
<213> ORGANISM: Artificial Sequence
<220> FEATURE:
<223> OTHER INFORMATION: Synthetic primer

<400> SEQUENCE: 45
ctgtccacct tccagagagt gtaccgacct cagtaagtag ccgtgactat cgacttccag     60
cctggcctca                                                             70
```

<210> SEQ ID NO 46
<211> LENGTH: 70
<212> TYPE: DNA
<213> ORGANISM: Artificial Sequence
<220> FEATURE:
<223> OTHER INFORMATION: Synthetic primer

<400> SEQUENCE: 46
ctgtccacct tccagccttt cctacgacct caatgcacat gtttggctcc tcttctccag        60
cctggcctcg                                                               70

<210> SEQ ID NO 47
<211> LENGTH: 70
<212> TYPE: DNA
<213> ORGANISM: Artificial Sequence
<220> FEATURE:
<223> OTHER INFORMATION: Synthetic primer

<400> SEQUENCE: 47
ccccagcctg gtggaagcta gctacctcaa tgctgctgct gtactactat gactgctgga        60
gatgagaaag                                                               70

<210> SEQ ID NO 48
<211> LENGTH: 90
<212> TYPE: DNA
<213> ORGANISM: Artificial Sequence
<220> FEATURE:
<223> OTHER INFORMATION: Synthetic primer

<400> SEQUENCE: 48
cgaaactttg cccatagcag attggaacgt ttaaatgcgt ctatttagtg gagccgagac        60
aatcttacat cgcaacccett gccgcatcca                                        90

<210> SEQ ID NO 49
<211> LENGTH: 90
<212> TYPE: DNA
<213> ORGANISM: Artificial Sequence
<220> FEATURE:
<223> OTHER INFORMATION: Synthetic primer

<400> SEQUENCE: 49
tgccagcctg tccttcctgc atcgtcttaa tcactagtcg gaagtactac tctcttacgc        60
ttacaactag ctcacctacc tgcccaccaa                                         90

<210> SEQ ID NO 50
<211> LENGTH: 90
<212> TYPE: DNA
<213> ORGANISM: Artificial Sequence
<220> FEATURE:
<223> OTHER INFORMATION: Synthetic primer

<400> SEQUENCE: 50
ggtgtgcgtg ccctgggacg actttctatg attactgacc tacctcaatg cacatgtttg        60
gctcctcttc gcgctggtgg cccagtgcct                                         90

<210> SEQ ID NO 51
<211> LENGTH: 70
<212> TYPE: DNA
<213> ORGANISM: Artificial Sequence
<220> FEATURE:
<223> OTHER INFORMATION: Synthetic primer

<400> SEQUENCE: 51
ggcgtaggca agagttcctg tagtaaagta gccgtgacta tcgactgaat ctaaggtagt    60
tggagctggt                                                           70

<210> SEQ ID NO 52
<211> LENGTH: 70
<212> TYPE: DNA
<213> ORGANISM: Artificial Sequence
<220> FEATURE:
<223> OTHER INFORMATION: Synthetic primer

<400> SEQUENCE: 52
ggcgtaggca agagtgtaag tcatcaagtc ggaagtacta ctctctgaat ctaaggtagt    60
tggagctgtt                                                           70

<210> SEQ ID NO 53
<211> LENGTH: 23
<212> TYPE: DNA
<213> ORGANISM: Artificial Sequence
<220> FEATURE:
<223> OTHER INFORMATION: Synthetic primer

<400> SEQUENCE: 53
cctcaatgct gctgctgtac tac                                            23

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
cctcaatgca catgtttggc tcc                                            23

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
agtagccgtg actatcgact                                                20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
tgcgtctatt tagtggagcc                                                20

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
agtcggaagt actactctct                                                20

-continued

```
<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
ctggaacggt gaaggtgaca                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
cggccacatt gtgaactttg                                               20

<210> SEQ ID NO 60
<211> LENGTH: 30
<212> TYPE: DNA
<213> ORGANISM: Artificial Sequence
<220> FEATURE:
<223> OTHER INFORMATION: Synthetic primer

<400> SEQUENCE: 60
atcatccatg gtgagctggc ggcgggtgtg                                    30

<210> SEQ ID NO 61
<211> LENGTH: 30
<212> TYPE: DNA
<213> ORGANISM: Artificial Sequence
<220> FEATURE:
<223> OTHER INFORMATION: Synthetic primer

<400> SEQUENCE: 61 ggcctttgcac atgccggagc cgttgtcgac                                   30

<210> SEQ ID NO 62
<211> LENGTH: 30
<212> TYPE: DNA
<213> ORGANISM: Artificial Sequence
<220> FEATURE:
<223> OTHER INFORMATION: Synthetic primer

<400> SEQUENCE: 62
ctgggcctcg tcgcccacat aggaatcctt                                    30

<210> SEQ ID NO 63
<211> LENGTH: 30
<212> TYPE: DNA
<213> ORGANISM: Artificial Sequence
<220> FEATURE:
<223> OTHER INFORMATION: Synthetic primer

<400> SEQUENCE: 63
cacagcctgg atagcaacgt acatggctgg                                    30

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
```
tgtatcgtca aggcactctt          20

<210> SEQ ID NO 65
<211> LENGTH: 25
<212> TYPE: DNA
<213> ORGANISM: Artificial Sequence
<220> FEATURE:
<223> OTHER INFORMATION: Synthetic primer

<400> SEQUENCE: 65
cctctattgt tggatcatat tcgtc          25

<210> SEQ ID NO 66
<211> LENGTH: 25
<212> TYPE: DNA
<213> ORGANISM: Artificial Sequence
<220> FEATURE:
<223> OTHER INFORMATION: Synthetic primer

<400> SEQUENCE: 66
tattcgtcca caaaatgatt ctgaa          25

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
tctttctctt ccgcacccag          20

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
ggcggcacac gtgggggttg          20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
ccttatacac cgtgccgaac          20

<210> SEQ ID NO 70
<211> LENGTH: 25
<212> TYPE: DNA
<213> ORGANISM: Artificial Sequence
<220> FEATURE:
<223> OTHER INFORMATION: Synthetic primer

<400> SEQUENCE: 70
agttggcaaa acatcttgtt gaggg          25

<210> SEQ ID NO 71
<211> LENGTH: 25
<212> TYPE: DNA
<213> ORGANISM: Artificial Sequence

```
<220> FEATURE:
<223> OTHER INFORMATION: Synthetic primer

<400> SEQUENCE: 71
ttccttccac tcggataaga tgctg                                              25

<210> SEQ ID NO 72
<211> LENGTH: 25
<212> TYPE: DNA
<213> ORGANISM: Artificial Sequence
<220> FEATURE:
<223> OTHER INFORMATION: Synthetic primer

<400> SEQUENCE: 72
gtggacgggc ggcggatcgg caaag                                              25

<210> SEQ ID NO 73
<211> LENGTH: 25
<212> TYPE: DNA
<213> ORGANISM: Artificial Sequence
<220> FEATURE:
<223> OTHER INFORMATION: Synthetic primer

<400> SEQUENCE: 73
atcatccatg gtgagctggc ggcgg                                              25

<210> SEQ ID NO 74
<211> LENGTH: 70
<212> TYPE: DNA
<213> ORGANISM: Artificial Sequence
<220> FEATURE:
<223> OTHER INFORMATION: Synthetic primer

<400> SEQUENCE: 74
gtggcgtagg caagatccta gtaatcagta gccgtgacta tcgactggtt caaagtggta        60
gttggagctg                                                               70

<210> SEQ ID NO 75
<211> LENGTH: 70
<212> TYPE: DNA
<213> ORGANISM: Artificial Sequence
<220> FEATURE:
<223> OTHER INFORMATION: Synthetic primer

<400> SEQUENCE: 75
gtggcgtagg caagattcta gatccctcaa tgcacatgtt tggctccggt tcaagtggta        60
gttggagcta                                                               70

<210> SEQ ID NO 76
<211> LENGTH: 70
<212> TYPE: DNA
<213> ORGANISM: Artificial Sequence
<220> FEATURE:
<223> OTHER INFORMATION: Synthetic primer

<400> SEQUENCE: 76
gtggcgtagg caagattcta gatccctcaa tgcacatgtt tggctccggt tcaagtggta        60
gttggagctc                                                               70

<210> SEQ ID NO 77
<211> LENGTH: 70
<212> TYPE: DNA
<213> ORGANISM: Artificial Sequence
<220> FEATURE:
<223> OTHER INFORMATION: Synthetic primer
```

<400> SEQUENCE: 77
gtggcgtagg caagattcta gatccctcaa tgcacatgtt tggctccggt tcaagtggta    60
gttggagctt    70

<210> SEQ ID NO 78
<211> LENGTH: 70
<212> TYPE: DNA
<213> ORGANISM: Artificial Sequence
<220> FEATURE:
<223> OTHER INFORMATION: Synthetic primer

<400> SEQUENCE: 78
tggcgtaggc aagagtccta gtaatcagta gccgtgacta tcgactggtt caaagggtag    60
ttggagctgg    70

<210> SEQ ID NO 79
<211> LENGTH: 70
<212> TYPE: DNA
<213> ORGANISM: Artificial Sequence
<220> FEATURE:
<223> OTHER INFORMATION: Synthetic primer

<400> SEQUENCE: 79
tggcgtaggc aagagttcta gatccctcaa tgcacatgtt tggctccggt tcaagggtag    60
ttggagctga    70

<210> SEQ ID NO 80
<211> LENGTH: 70
<212> TYPE: DNA
<213> ORGANISM: Artificial Sequence
<220> FEATURE:
<223> OTHER INFORMATION: Synthetic primer

<400> SEQUENCE: 80
tggcgtaggc aagagttcta gatccctcaa tgcacatgtt tggctccggt tcaagggtag    60
ttggagctgt    70

<210> SEQ ID NO 81
<211> LENGTH: 70
<212> TYPE: DNA
<213> ORGANISM: Artificial Sequence
<220> FEATURE:
<223> OTHER INFORMATION: Synthetic primer

<400> SEQUENCE: 81
tggcgtaggc aagagttcta gatccctcaa tgcacatgtt tggctccggt tcaagggtag    60
ttggagctgc    70

<210> SEQ ID NO 82
<211> LENGTH: 70
<212> TYPE: DNA
<213> ORGANISM: Artificial Sequence
<220> FEATURE:
<223> OTHER INFORMATION: Synthetic primer

<400> SEQUENCE: 82
cgtaggcaag agtgctccta gtaatcagta gccgtgacta tcgactggtt caaagagttg    60
gagctggtgg    70

<210> SEQ ID NO 83
<211> LENGTH: 70

```
<212> TYPE: DNA
<213> ORGANISM: Artificial Sequence
<220> FEATURE:
<223> OTHER INFORMATION: Synthetic primer

<400> SEQUENCE: 83
cgtaggcaag agtgcttcta gatccctcaa tgcacatgtt tggctccggt tcaagagttg      60
gagctggtga                                                             70

<210> SEQ ID NO 84
<211> LENGTH: 70
<212> TYPE: DNA
<213> ORGANISM: Artificial Sequence
<220> FEATURE:
<223> OTHER INFORMATION: Synthetic primer

<400> SEQUENCE: 84
gaggagtaca gtgcatccta gtaatcagta gccgtgacta tcgactggtt caaaggacac      60
agcaggtcaa                                                             70

<210> SEQ ID NO 85
<211> LENGTH: 70
<212> TYPE: DNA
<213> ORGANISM: Artificial Sequence
<220> FEATURE:
<223> OTHER INFORMATION: Synthetic primer

<400> SEQUENCE: 85
gaggagtaca gtgcacgcta gatccctcaa tgcacatgtt tggctccggt tcaaggacac      60
agcaggtcat                                                             70

<210> SEQ ID NO 86
<211> LENGTH: 70
<212> TYPE: DNA
<213> ORGANISM: Artificial Sequence
<220> FEATURE:
<223> OTHER INFORMATION: Synthetic primer

<400> SEQUENCE: 86
ggccaaactg ctgggtccta gtaatcagta gccgtgacta tcgactggtt caaagcacag      60
attttgggct                                                             70

<210> SEQ ID NO 87
<211> LENGTH: 70
<212> TYPE: DNA
<213> ORGANISM: Artificial Sequence
<220> FEATURE:
<223> OTHER INFORMATION: Synthetic primer

<400> SEQUENCE: 87
ggccaaactg ctgggttcta gatacctcaa tgctgctgct gtactacggt tcaagcacag      60
attttgggcg                                                             70

<210> SEQ ID NO 88
<211> LENGTH: 70
<212> TYPE: DNA
<213> ORGANISM: Artificial Sequence
<220> FEATURE:
<223> OTHER INFORMATION: Synthetic primer

<400> SEQUENCE: 88
cgtggacaac ccccatccta gtaatcagta gccgtgacta tcgactggtt caaagctacg      60
tgatggccag                                                             70
```

```
<210> SEQ ID NO 89
<211> LENGTH: 70
<212> TYPE: DNA
<213> ORGANISM: Artificial Sequence
<220> FEATURE:
<223> OTHER INFORMATION: Synthetic primer

<400> SEQUENCE: 89
cgtggacaac ccccattcta gatacctcaa tgctgctgct gtactacggt tcaagctacg      60
tgatggccat                                                             70

<210> SEQ ID NO 90
<211> LENGTH: 70
<212> TYPE: DNA
<213> ORGANISM: Artificial Sequence
<220> FEATURE:
<223> OTHER INFORMATION: Synthetic primer

<400> SEQUENCE: 90
gctccggtgc gttcgtccta gtaatcagta gccgtgacta tcgactggtt caaagagatc      60
aaagtgctgg                                                             70

<210> SEQ ID NO 91
<211> LENGTH: 70
<212> TYPE: DNA
<213> ORGANISM: Artificial Sequence
<220> FEATURE:
<223> OTHER INFORMATION: Synthetic primer

<400> SEQUENCE: 91
gctccggtgc gttcgttcta gatccctcaa tgcacatgtt tggctccggt tcaagagatc      60
aaagtgctgt                                                             70

<210> SEQ ID NO 92
<211> LENGTH: 70
<212> TYPE: DNA
<213> ORGANISM: Artificial Sequence
<220> FEATURE:
<223> OTHER INFORMATION: Synthetic primer

<400> SEQUENCE: 92
ctccggtgcg ttcggtccta gtaatcagta gccgtgacta tcgactggtt caaaggatca      60
aagtgctggc                                                             70

<210> SEQ ID NO 93
<211> LENGTH: 70
<212> TYPE: DNA
<213> ORGANISM: Artificial Sequence
<220> FEATURE:
<223> OTHER INFORMATION: Synthetic primer

<400> SEQUENCE: 93
ctccggtgcg ttcggttcta gatccctcaa tgcacatgtt tggctccggt tcaatgatca      60
aagtgctggg                                                             70

<210> SEQ ID NO 94
<211> LENGTH: 70
<212> TYPE: DNA
<213> ORGANISM: Artificial Sequence
<220> FEATURE:
<223> OTHER INFORMATION: Synthetic primer

<400> SEQUENCE: 94
```

```
ccctgccctc aacaattcct tttacgacct caatgctgct gctgtactac tcttcgactt    60
gcacgtactc                                                           70

<210> SEQ ID NO 95
<211> LENGTH: 70
<212> TYPE: DNA
<213> ORGANISM: Artificial Sequence
<220> FEATURE:
<223> OTHER INFORMATION: Synthetic primer

<400> SEQUENCE: 95
ccctgccctc aacaactagt atctgagtcg gaagtactac tctcttgtgc cataagactt    60
gcacgtactt                                                           70

<210> SEQ ID NO 96
<211> LENGTH: 70
<212> TYPE: DNA
<213> ORGANISM: Artificial Sequence
<220> FEATURE:
<223> OTHER INFORMATION: Synthetic primer

<400> SEQUENCE: 96
ctcctcagca tcttattcct tttacgacct caatgctgct gctgtactac tcttcgcgat    60
ggtctggccc                                                           70

<210> SEQ ID NO 97
<211> LENGTH: 70
<212> TYPE: DNA
<213> ORGANISM: Artificial Sequence
<220> FEATURE:
<223> OTHER INFORMATION: Synthetic primer

<400> SEQUENCE: 97
ctcctcagca tcttactagt atctgagtcg gaagtactac tctcttgtgc cataagcgat    60
ggtctggcct                                                           70

<210> SEQ ID NO 98
<211> LENGTH: 70
<212> TYPE: DNA
<213> ORGANISM: Artificial Sequence
<220> FEATURE:
<223> OTHER INFORMATION: Synthetic primer

<400> SEQUENCE: 98
agcctcgcct ttgccttcct tttacgacct caatgctgct gctgtactac tcttcgcccc    60
gcgagcacag                                                           70

<210> SEQ ID NO 99
<211> LENGTH: 70
<212> TYPE: DNA
<213> ORGANISM: Artificial Sequence
<220> FEATURE:
<223> OTHER INFORMATION: Synthetic primer

<400> SEQUENCE: 99
agcctcgcct ttgccttcct tttacgacct caatgcacat gtttggctcc tcttcgcccc    60
gcgagcacag                                                           70

<210> SEQ ID NO 100
<211> LENGTH: 148
<212> TYPE: DNA
<213> ORGANISM: Artificial Sequence
```

```
<220> FEATURE:
<223> OTHER INFORMATION: Synthetic primer

<400> SEQUENCE: 100
gcatatacat ctgactgaaa gctgtatgga tttttatctt gcattctgat gacttctggt    60
gccatccaca aaatggatcc agacaactgt tcaaactgat gggacccact ccatcgagat   120
ttcactgtag ctagaccaaa atcaccta                                      148

<210> SEQ ID NO 101
<211> LENGTH: 30
<212> TYPE: DNA
<213> ORGANISM: Artificial Sequence
<220> FEATURE:
<223> OTHER INFORMATION: Synthetic primer

<400> SEQUENCE: 101
ctccatcgag atttcactgt agctagacca                                     30

<210> SEQ ID NO 102
<211> LENGTH: 15
<212> TYPE: DNA
<213> ORGANISM: Artificial Sequence
<220> FEATURE:
<223> OTHER INFORMATION: Synthetic primer

<400> SEQUENCE: 102
gaaatctcga tggag                                                     15

<210> SEQ ID NO 103
<211> LENGTH: 14
<212> TYPE: DNA
<213> ORGANISM: Artificial Sequence
<220> FEATURE:
<223> OTHER INFORMATION: Synthetic primer

<400> SEQUENCE: 103
aaatctcgat ggag                                                      14

<210> SEQ ID NO 104
<211> LENGTH: 13
<212> TYPE: DNA
<213> ORGANISM: Artificial Sequence
<220> FEATURE:
<223> OTHER INFORMATION: Synthetic primer

<400> SEQUENCE: 104
aatctcgatg gag                                                       13

<210> SEQ ID NO 105
<211> LENGTH: 12
<212> TYPE: DNA
<213> ORGANISM: Artificial Sequence
<220> FEATURE:
<223> OTHER INFORMATION: Synthetic primer

<400> SEQUENCE: 105
atctcgatgg ag                                                        12

<210> SEQ ID NO 106
<211> LENGTH: 11
<212> TYPE: DNA
<213> ORGANISM: Artificial Sequence
<220> FEATURE:
<223> OTHER INFORMATION: Synthetic primer

<400> SEQUENCE: 106
```

```
tctcgatgga g                                                           11

<210> SEQ ID NO 107
<211> LENGTH: 10
<212> TYPE: DNA
<213> ORGANISM: Artificial Sequence
<220> FEATURE:
<223> OTHER INFORMATION: Synthetic primer

<400> SEQUENCE: 107
ctcgatggag                                                             10

<210> SEQ ID NO 108
<211> LENGTH: 14
<212> TYPE: DNA
<213> ORGANISM: Artificial Sequence
<220> FEATURE:
<223> OTHER INFORMATION: Synthetic primer

<400> SEQUENCE: 108
tggtctagct acag                                                        14

<210> SEQ ID NO 109
<211> LENGTH: 13
<212> TYPE: DNA
<213> ORGANISM: Artificial Sequence
<220> FEATURE:
<223> OTHER INFORMATION: Synthetic primer

<400> SEQUENCE: 109
ggtctagcta cag                                                         13

<210> SEQ ID NO 110
<211> LENGTH: 12
<212> TYPE: DNA
<213> ORGANISM: Artificial Sequence
<220> FEATURE:
<223> OTHER INFORMATION: Synthetic primer

<400> SEQUENCE: 110
gtctagctac ag                                                          12

<210> SEQ ID NO 111
<211> LENGTH: 11
<212> TYPE: DNA
<213> ORGANISM: Artificial Sequence
<220> FEATURE:
<223> OTHER INFORMATION: Synthetic primer

<400> SEQUENCE: 111
tctagctaca g                                                           11

<210> SEQ ID NO 112
<211> LENGTH: 10
<212> TYPE: DNA
<213> ORGANISM: Artificial Sequence
<220> FEATURE:
<223> OTHER INFORMATION: Synthetic primer

<400> SEQUENCE: 112
ctagctacag                                                             10
```